(12) United States Patent
Protzer et al.

(10) Patent No.: US 10,912,827 B2
(45) Date of Patent: Feb. 9, 2021

(54) MEANS AND METHODS FOR TREATING HBV

(71) Applicant: HELMHOLTZ ZENTRUM MÜNCHEN—DEUTSCHES FORSCHUNGSZENTRUM FÜR GESUNDHEIT UND UMWELT (GMBH), Neuherberg (DE)

(72) Inventors: Ulrike Protzer, Munich (DE); Tanja Bauer, Ottenhofen (DE); Anna Kosinska, Munich (DE); Martin Mueck-Haeusl, Munich (DE)

(73) Assignee: HELMHOLTZ ZENTRUM MÜNCHEN—DEUTSCHES FORSCHUNGSZENTRUM FÜR GESUNDHEIT UND UMWELT (GMBH), Neuherberg (DE)

( * ) Notice: Subject to any disclaimer, the term of this patent is extended or adjusted under 35 U.S.C. 154(b) by 164 days.

(21) Appl. No.: 16/069,268

(22) PCT Filed: Jan. 12, 2017

(86) PCT No.: PCT/EP2017/050553
§ 371 (c)(1),
(2) Date: Jul. 11, 2018

(87) PCT Pub. No.: WO2017/121791
PCT Pub. Date: Jul. 20, 2017

(65) Prior Publication Data
US 2019/0030158 A1 Jan. 31, 2019

(30) Foreign Application Priority Data

Jan. 12, 2016 (LU) .......................... 92942

(51) Int. Cl.
*A61K 39/12* (2006.01)
*A61K 39/29* (2006.01)
(Continued)

(52) U.S. Cl.
CPC ............ *A61K 39/292* (2013.01); *A61K 39/12* (2013.01); *A61P 31/20* (2018.01);
(Continued)

(58) Field of Classification Search
None
See application file for complete search history.

(56) References Cited

U.S. PATENT DOCUMENTS 6,235,288 B1 5/2001 Chisari
2008/0267996 A1 10/2008 Schneider et al.

FOREIGN PATENT DOCUMENTS

WO 2009056535 A2 5/2009

OTHER PUBLICATIONS

Kunke David et al., "Vaccinia Virus Recombinants Coexpressing Hepatitis B Virus Surface and Core Antigens". 1993, Virology. 195: 132-139.
(Continued)

*Primary Examiner* — Michelle S Horning
(74) *Attorney, Agent, or Firm* — Riverside Law LLP

(57) ABSTRACT

The present invention relates to an improved recombinant vaccination vector for the treatment or vaccination against hepatitis B virus (HBV) as well as pharmaceutical compositions or vaccines comprising said recombinant vaccination vector. The present invention also relates to a recombinant vaccination vector for use in a method of vaccination against HBV, as well as kits comprising a vaccine comprising the recombinant vaccination vector.

21 Claims, 36 Drawing Sheets

Specification includes a Sequence Listing.

(51) Int. Cl.
   *C12N 15/86* (2006.01)
   *C12N 15/113* (2010.01)
   *A61P 31/20* (2006.01)
   *A61K 39/00* (2006.01)

(52) U.S. Cl.
   CPC .......... *C12N 15/1131* (2013.01); *C12N 15/86* (2013.01); *A61K 2039/52* (2013.01); *A61K 2039/525* (2013.01); *A61K 2039/5256* (2013.01); *A61K 2039/545* (2013.01); *A61K 2039/55505* (2013.01); *A61K 2039/55555* (2013.01); *A61K 2039/55561* (2013.01); *A61K 2039/58* (2013.01); *C12N 2310/14* (2013.01); *C12N 2320/31* (2013.01); *C12N 2710/24143* (2013.01); *C12N 2730/10134* (2013.01); *C12N 2799/023* (2013.01)

(56) References Cited

OTHER PUBLICATIONS

Shata M. T. M. et al., "Attempted Therapeutic Immunization in a Chimpanzee Chronic HBV Carrier with a High Viral Load". 2006, J. Medical Primatology, 35: 165-171.

Buchmann P. et al., "A Novel Therapeutic Hepatitis B Vaccine Induces Cellular and Humoral Immune Responses and Breaks Tolerance in Hepatitis B Virus (HBV) Transgenic Mice" 2013, Vaccine, 31: 1197-1203.

Du X. et al., "The Adjuvant Effects of Co-Stimulatory Molecules on Cellular and Memory Responses to HBsAg DNA Vaccination". 2007, J. Gene Medicine., 9: 136-146.

Backes S. et al., "Protein-Prime/Modified Vaccinia Virus Ankara Vector-Boost Vaccination Overcomes Tolerance in High-Antigenemic HBV-Transgenic Mice". 2016, Vaccine 34: 923-932.

Li J. et al., "Immunogenicity and Protection Efficacy of Monomeric and Trimeric Recombinant SARS Coronavirus Spike Protein Subunit Vaccine Candidates", 2013, Viral Immunology, 26, 126-132.

Yarilin A.A. "Immunologiya" (published on https://studfile.net/preview/1823558/ 14.02.2015), pp. 271-276; machine generated translation.

Yarilin A.A. "Immunologiya" (published on https://studfile.net/preview/1823558/ 14.02.2015), pp. 715-716; machine generated translation.

Figure 2
A
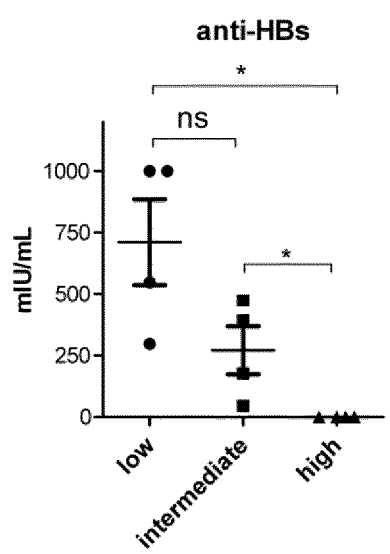
B
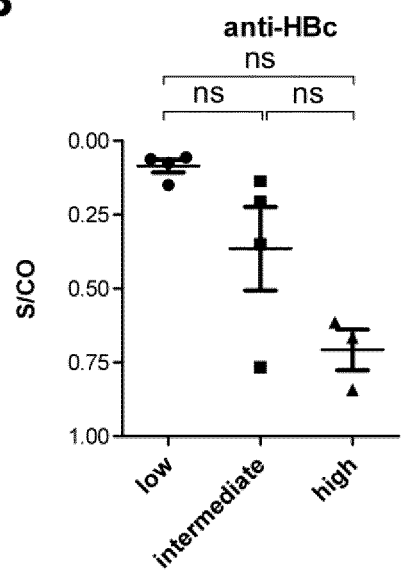
C
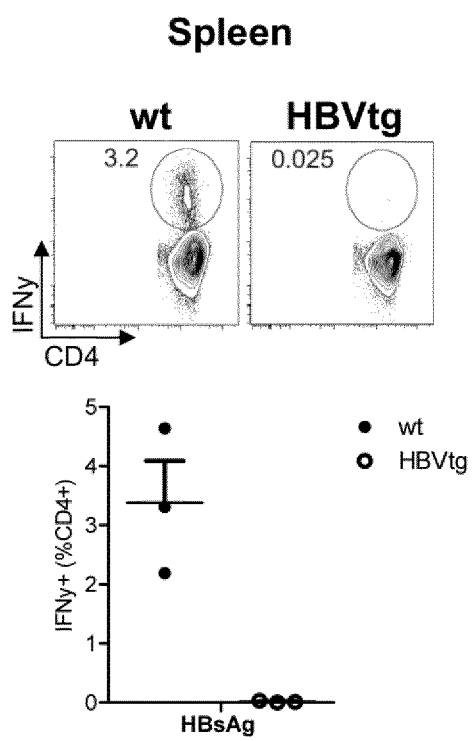
D
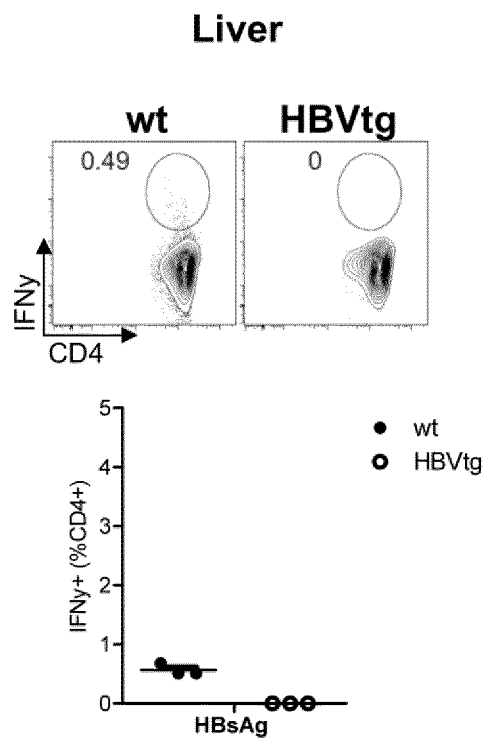

Figure 3
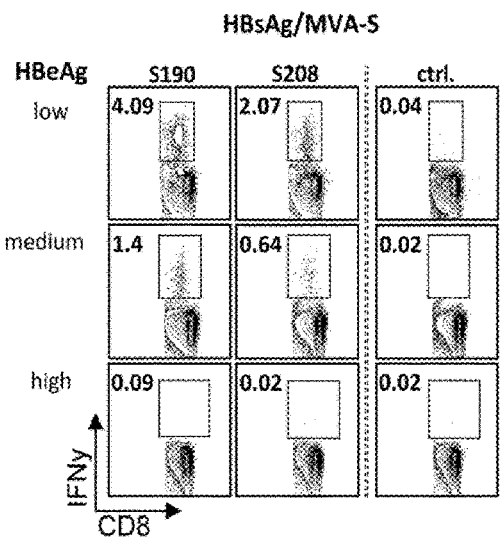
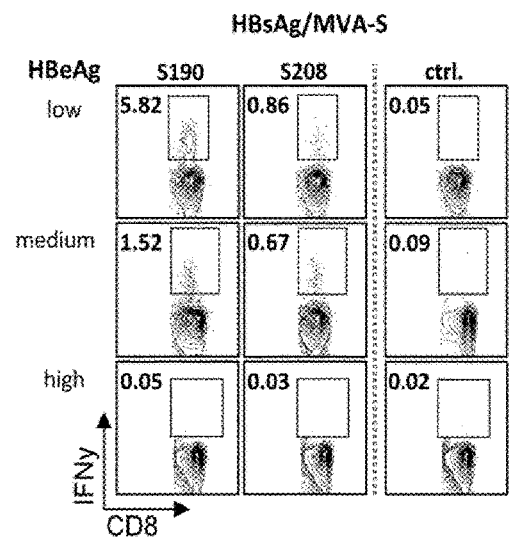
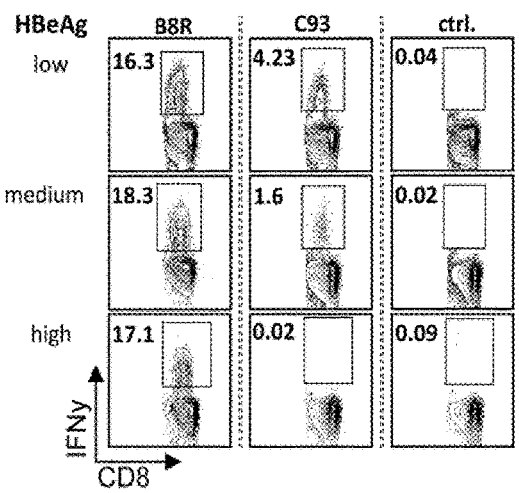
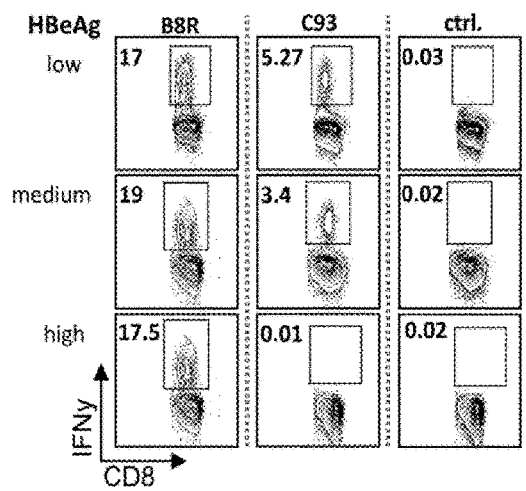
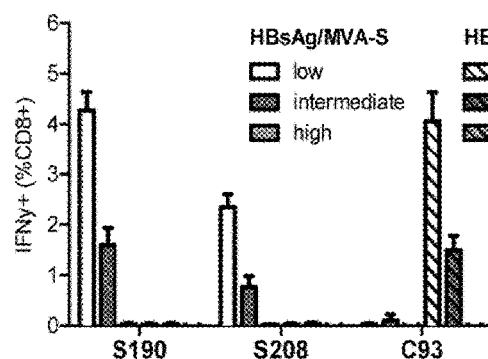
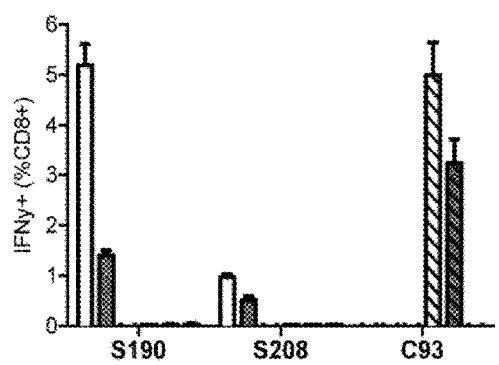

Figure 10

| Antigenemia | HBeAg (S/CO) | HBsAg (S/CO) | Serum HBV DNA copies/ml |
|---|---|---|---|
| Low | <2 | neg. | $5 \times 10^3$ to $5 \times 10^4$ |
| Intermediate | 2-6 | neg. | $1 \times 10^4$ to $1 \times 10^5$ |
| High | 7-60 | 5-45 | $1 \times 10^5$ to $1 \times 10^6$ |

Figure 11

| peptide | specificity | sequence | |
|---|---|---|---|
| $S_{190}$ | HBsAg (ayw) | VWLSVIWM# | (SEQ ID NO: 19) |
| $S_{208}$ | HBsAg (ayw) | ILSPFLPL | (SEQ ID NO: 21) |
| $S_{208adw}$ | HBsAg (adw) | IVSPFIPL | (SEQ ID NO: 22) |
| S Pool | HBsAg (ayw) | 15-mer peptides covering the C-terminus (aa 145-226) of S subtype ayw | (SEQ ID NO: 23) |
| $C_{93}$ | HBcAg (ayw) | MGLKFRQL | (SEQ ID NO: 24) |
| $B8R_{20}$ | MVA | TSYKFESV | (SEQ ID NO: 20) |
| $\beta\text{-Gal}_{96}$ | β-galactosidase (negative control) | DAPIYTNV | (SEQ ID NO: 25) | peptide is generated only from endogenously expressed antigen

Figure 12
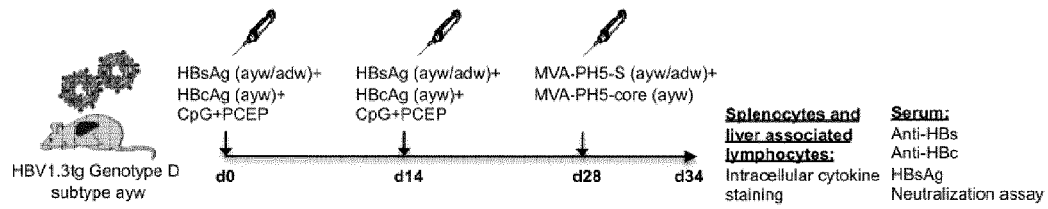
Figure 13
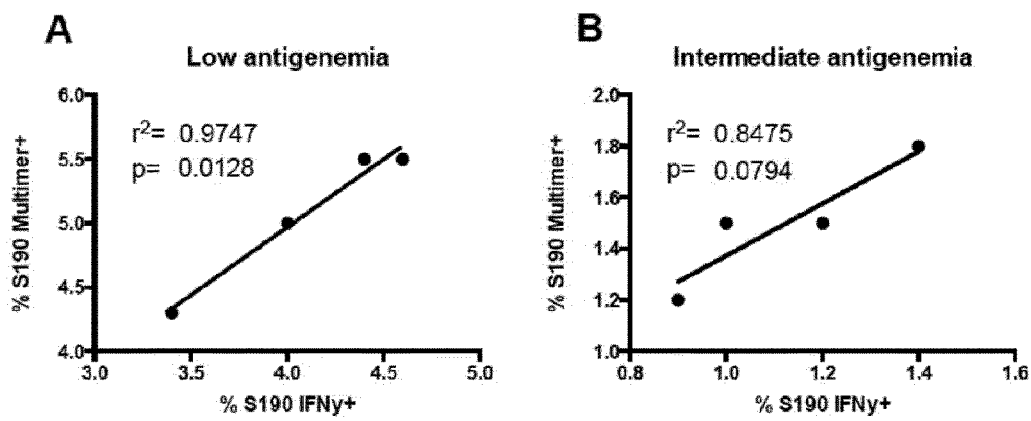
Figure 14
| HBeAg | Serum anti-HBs [mIU/mL] | serum HBsAg [IU/ml] | HBsAg in precipitated immune complexes [IU/mL] |
|---|---|---|---|
| Mouse 1 High | nd | 1160 | 7,6 |
| Mouse 2 High | nd | 85 | 5,7 |
| Mouse 3 High | nd | 24 | 6,4 |
| Mouse 4 Intermediate | 800 | 3 | 4,7 |
| Mouse 1 Low | >10000 | nd | 0,8 |

Figure 19

Small envelope protein of HBV A2/adw2 including C-terminal overhang

MENITSGFLGPLLVLQAGFFLLTRILTIPQSLDSWWTSLNFLGGSPVCLGQNSQSPTSNHSPTSCPPI
CPGYRWMCLRRFIIFLFILLLCLIFLLVLLDYQGMLPVCPLIPGSTTTSTGPCKTCTTPAQGNSMFPS
CCCTKPTDGNCTCIPIPSSWAFAKYLWEWASVRFSWLSLLVPFVQWFVGLSPTVWLSAIWMMWYWGPS
LYSIVSPFIPLLPIFFCLWVYIGSGATNFSLLKQAGDVEENPG (SEQ ID NO: 10)

Figure 20

Core protein fragment 1-149 of HBV D/ayw including N- and C-terminal overhangs

PMDIDPYKEFGATVELLSFLPSDFFPSVRDLLDTASALYREALESPEHCSPHHTALRQAILCWGELMT
LATWVGVNLEDPASRDLVVSYVNTNMGLKFRQLLWFHISCLTFGRETVIEYLVSFGVWIRTPPAYRPP
NAPILSTLPETTVVGSGATNFSLLKQAGDVEENPG (SEQ ID NO: 12)

Figure 21

RT domain of HBV polymerase including N- and C-terminal overhangs

PEDWGPCAEHGEHHIRIPRTPARVTGGVFLVDKNPHNTAESRLVVDFSQFSRGKTRVSWPKFAVPNLQ
SLTNLLSSNLSWLSLDVSAAFYHIPLHPAAMPHLLVGSSGLSRYVARLSSNSRIFNHQHGNLQNLHDS
CSRNLYVSLLLLYKTFGRKLHLYSHPIILGFRKIPMGVGLSPFLLAQFTSAICSVVRRAFPHCLAFSY
MDDVVLGAKSVQHLESLFTAVTNFLLSLGIHLNPNKTKRWGYSLNFMGYVIGSWGTLPQEHIVQKIKQ
CFRKLPVNRPIDWKVCQRIVGLLGFAAPFTQCGYPALMPLYACIQSKQAFTFSPTYKAFLCKQYLNLY
PVARQGSGEGRGSLLTCGDVEENPG (SEQ ID NO: 16)

Figure 22

Large envelope protein of HBV C/ayw including N- and C-terminal overhangs

PMGGWSSKPRQGMGTNLSVPNPLGFFPDHQLDPAFGANSNNPDWDFNPNKDHWPEANQVGAGAFGPGF
TPPHGGLLGWSPQAQGILTTVPAAPPPASTNRQSGRQPTPISPPLRDSHPQAMQWNSTTFHQALLDPR
VRGLYFPAGGSSSGTVNPVPTTASPISSIFSRTGDPAPNMENTTSGFLGPLLVLQAGFLLLTRILTIP
QSLDSWWTSLNFLGGAPTCPGQNSQSPTSNHSPTSCPPICPGYRWMCLRRFIIFLFILLLCLIFLLVL
LDYQGMLPVCPLLPGTSTTSTGPCRTCTIPAQGTSMFPSCCCTKPSDGNCTCIPIPSSWAFAKFLWEW
ASVRFSWLSLLVPFVQWFVGLSPTVWLSVIWMMWYWGPSLYNILSPFLPLLPIFFCLWVYIGSGEGRG
SLLTCGDVEENPG
(SEQ ID NO: 14)

Figure 23

Core protein of HBV C/ayw including N-terminal overhang

PMDIDPYKEFGASVELLSFLPSDFFPSIRDLLDTASALYREALESPEHCSPHHTALRQAILCWGELMN
LATWVGSNLEDPASRELVVSYVNVNMGLKIRQLLWFHISCLTFGRETVLEYLVSFGVWIRTPPAYRPP
NAPILSTLPETTVVRRRGRSPRRRTPSPRRRRSQSPRRRRSQSRESQC
(SEQ ID NO: 15)

Figure 24

Consensus sequence of RT-domain of HBV polymerase:

```
EDWGPCTEHGEHHIRIPRTPARVTGGVFLVDKNPHNTAESRLVVDFSQFSRGNTRVSWPKFAVPNLQS
LTNLLSSNLSWLSLDVSAAFYHLPLHPAAMPHLLVGSSGLSRYVARLSSNSRIINHQHGTMQNLHDSC
SRNLYVSLLLLYKTFGRKLHLYSHPIILGFRKIPMCVGLSPFLLAQFTSAICSVVRRAFPHCLAFSYM
DDVVLGAKSVQHLESLYTAVTNFLLSLGIHLNPNKTKRWGYSLNFMGYVIGSWGTLPQEHIVQKIKQC
FRKLPVNRPIDWKVCQRIVGLLGFAAPFTQCGYPALMPLYACIQAKQAFTFSPTYKAFLCKQYLNLYP
VAR
```
(SEQ ID NO: 03)

Figure 25

Consensus sequence of large envelope proteins of genotype C HBV strains

```
MGGWSSKPRQGMGTNLSVPNPLGFFPDHQLDPAFGANSNNPDWDFNPNKDHWPEANQVGAGAFGPGFT
PPHGGLLGWSPQAQGILTTVPAAPPPASTNRQSGRQPTPISPPLRDSHPQAMQWNSTTFHQALLDPRV
RGLYFPAGGSSSGTVNPVPTTASPISSIFSRTGDPAPNMENTTSGFLGPLLVLQAGFFLLTRILTIPQ
SLDSWWTSLNFLGGAPTCPGQNSQSPTSNHSPTSCPPICPGYRWMCLRRFIIFLFILLLCLIFLLVLL
DYQGMLPVCPLLPGTSTTSTGPCKTCTIPAQGTSMFPSCCCTKPSDGNCTCIPIPSSWAFARFLWEWA
SVRFSWLSLLVPFVQWFVGLSPTVWLSVIWMMWYWGPSLYNILSPFLPLLPIFFCLWVYI
```
(SEQ ID NO: 01)

Figure 26

Consensus sequence of core protein of genotype C HBV strains

```
MDIDPYKEFGASVELLSFLPSDFFPSIRDLLDTASALYREALESPEHCSPHHTALRQAILCWGELMNL
ATWVGSNLEDPASRELVVSYVNVNMGLKIRQLLWFHISCLTFGRETVLEYLVSFGVWIRTPPAYRPPN
APILSTLPETTVVRRRGRSPRRRTPSPRRRRSQSPRRRRSQSRESQC
```
(SEQ ID NO: 02)

Figure 29
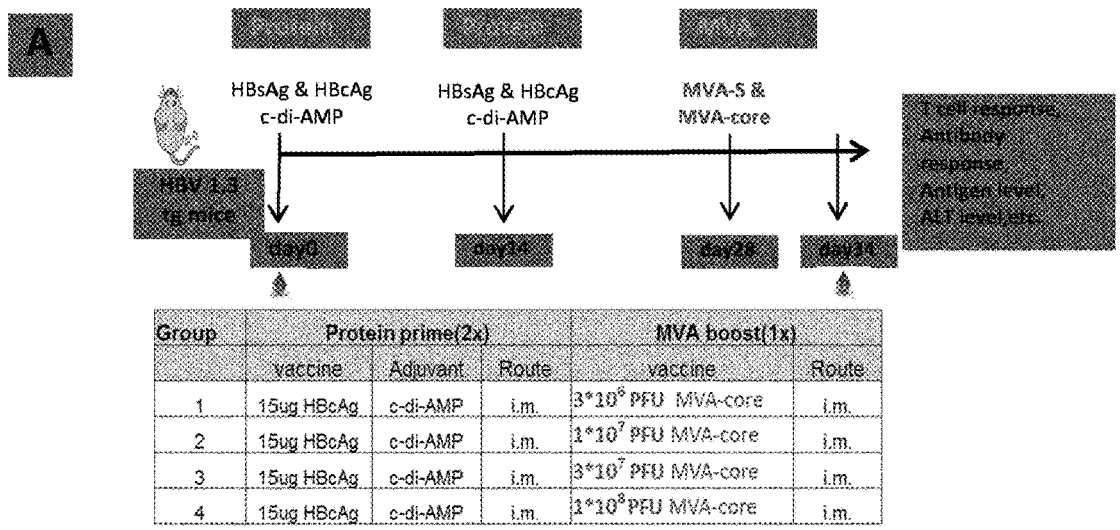
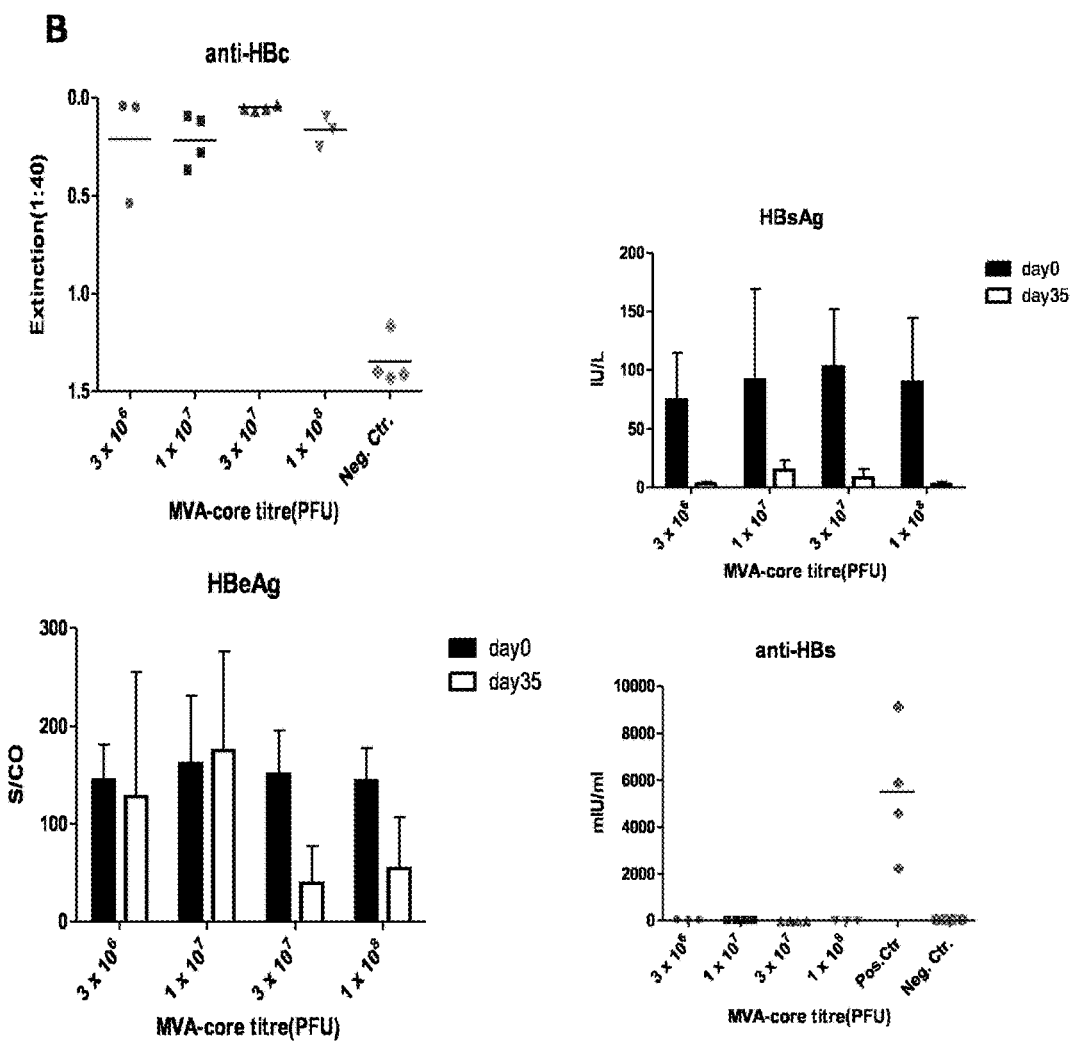

Figure 29 (cont.)
C
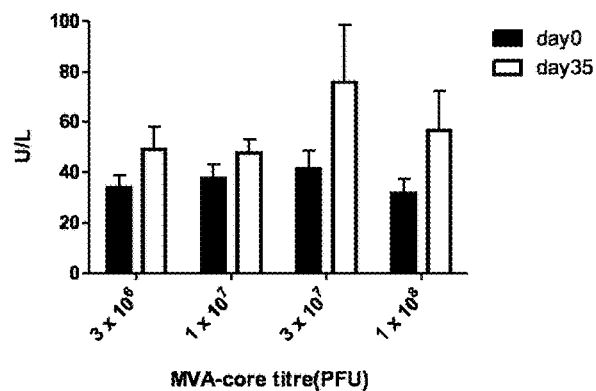
D
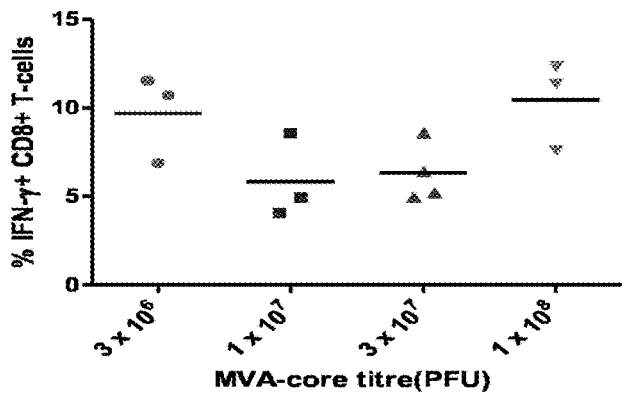
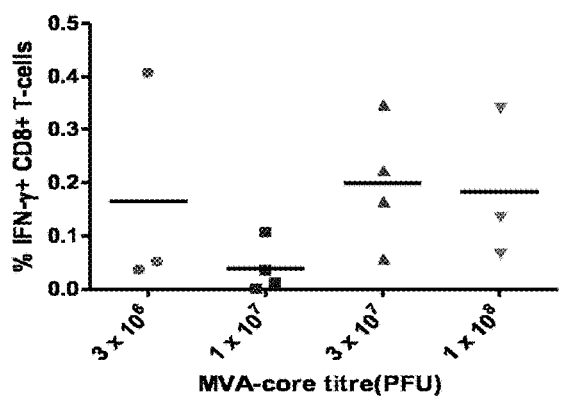
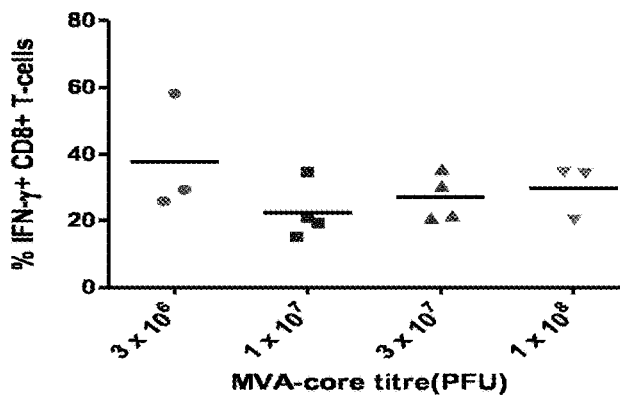
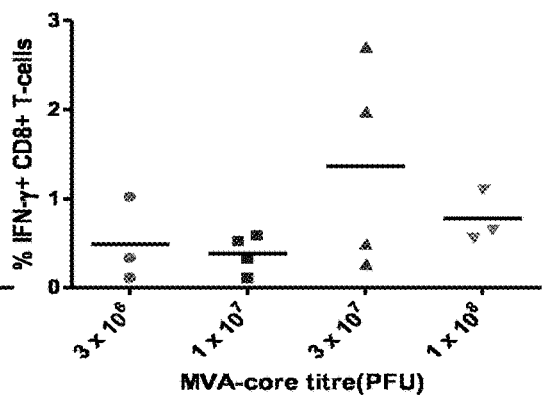

Figure 30
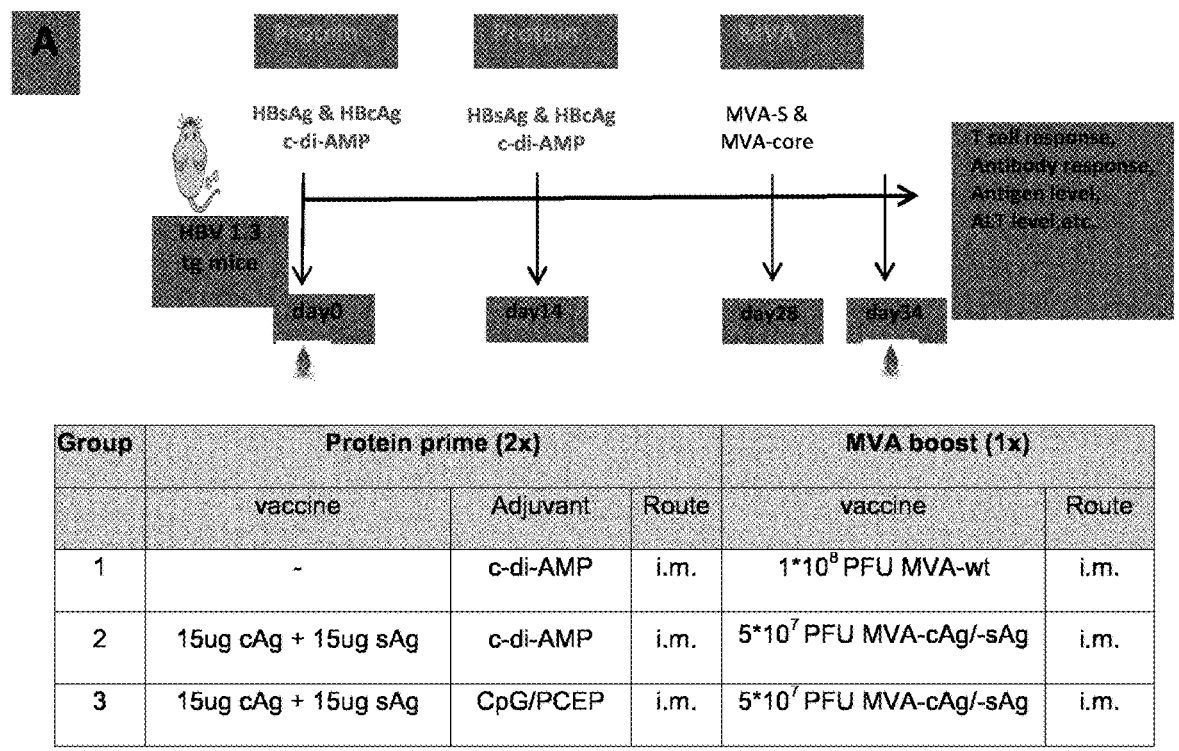
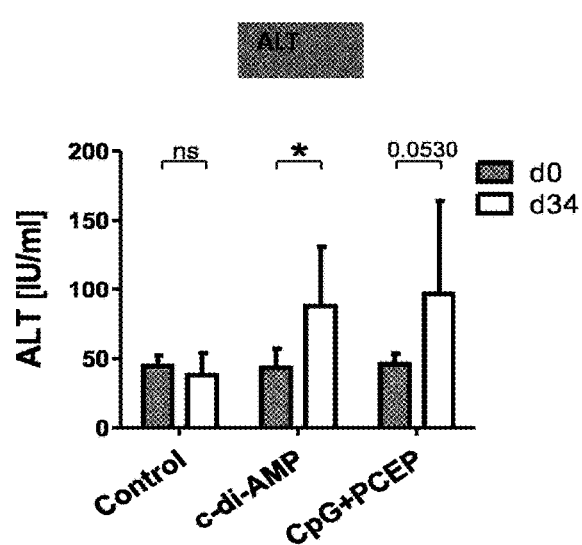

Figure 33

Construct of the recombinant vaccination vector (rMVA) further expressing CD70

CCTGGGACATACGTATATTTCTATGATCTGTCTTATATGAAGTCTATACAGCGAATAGATTC
AGAATTTCTACATAATTATATATTGTACGCTAATAAGTTTAATCTAACACTCCCCGAAGATTT
GTTTATAATCCCTACAAATTTGGATATTCTATGGCGTACAAAGGAATATATAGACTCGTTCG
ATATTAGTACAGAAACATGGAATAAATTATTATCCAATTATTATATGAAGATGATAGAGTATG
CTAAACTTTATGTACTAAGTCCTATTCTCGCTGAGGAGTTGGATAATTTTGAGAGGACGGGA
GAATTAACTCGAGGCCGCTGGTACCCAACCTAAAAATTGAAAATAAATACAAAGGTTCTTGA
GGGTTGTGTTAAATTGAAAGCGAGAAATAATCATAAATAAGCCCGGGGATCAACC

ATGGACATCGACCCTTATAAAGAATTTGGAGCTACTGTGGAGTTACTCTCGTTTTTGCCTTT
GACTTCTTTCCTTCAGTACGAGATCTTCTAGATACCGCCTCAGCTCTGTATCGGGAAGCCT
TAGAGTCTCCTGAGCATTGTTCACCTCACCATACTGCACTCAGGCAAGCAATTCTTTGCTG
GGGGGAACTAATGACTCTAGCTACCTGGGTGGGTGTTAATTTGGAAGATCCAGCGTCTAG
AGACCTAGTAGTCAGTTATGTCAACACTAATATGGGCCTAAAGTTCAGGCAACTCTTGTGG
TTTCACATTTCTTGTCTCACTTTTGGAAGAGAAACAGTTATAGAGTATTTGGTGTCTTTCGGA
GTGTGGATTCGCACTCCTCCAGCTTATAGACCACCAAATGCCCTATCCTATCAACACTTC
CGGAGACTACTGTTGTTAGACGACGAGGCAGGTCCCCTAGAAGAAGAACTCCCTCGCCTC
GCAGACGAAGGTCTCAATCGCCGCGTCGCAGAAGATCTCAATCTCGGGAATCTCAATGT
GGCTCCGGAGCCACCAACTTCTCCCTGCTGAAGCAGGCCGGCGACGTGGAGGAGAACCC
CGGCCCTTGCTGGAATTCGCCCTTATCGACCCAAGTACCGCCACCTAAGGCG

ATGCCGGAGGAGGGTTCGGGCTGCTCGGTGCGGCGCAGGCCCTATGGGTGCGTCCTGC
GGGCTGCTTTGGTCCCATTGGTCGCGGGCTTGGTGATCTGCCTCGTGGTGTGCATCCAGC
GCTTCGCACAGGCTCAGCAGCAGCTGCCGCTCGAGTCACTTGGGTGGGACGTAGCTGAG
CTGCAGCTGAATCACACAGGACCTCAGCAGGACCCCAGGCTATACTGGCAGGGGGCCC
AGCACTGGGCCGCTCCTTCCTGCATGGACCAGAGCTGGACAAGGGGCAGCTACGTATCCA
TCGTGATGGCATCTACATGGTACACATCCAGGTGACGCTGGCCATCTGCTCCTCCACGAC
GGCCTCCAGGCACCACCCCACCACCCTGGCCGTGGGAATCTGCTCTCCCGCCTCCCGTA
GCATCAGCCTGCTGCGTCTCAGCTTCCACCAAGGTTGTACCATTGCCTCCCAGCGCCTGA
CGCCCCTGGCCCGAGGGGACACACTCTGCACCAACCTCACTGGGACACTTTTGCCTTCCC
GAAACACTGATGAGACCTTCTTTGGAGTGCAGTGGGTGCGCCCTGATTGACCCGCGGGC
CCGGGATCCGCCCCTCTCCCTCCCCCCCCCTAACGTTACTGGCCGAAGCCGCTTGGAA
TAAGGCCGGTGTGCGTTTGTCTATATGTTATTTTCCACCATATTGCCGTCTTTTGGCAATG
TGAGGGCCCGGAAACCTGGCCCTGTCTTCTTGACGAGCATTCCTAGGGGTCTTTCCCCTC
TCGCCAAAGGAATGCAAGGTCTGTTGAATGTCGTGAAGGAAGCAGTTCCTCTGGAAGCT
TCTTGAAGACAAACAACGTCTGTAGCGACCCTTTGCAGGCAGCGGAACCCCCCACCTGG
CGACAGGTGCCTCTGCGGCCAAAAGCCACGTGTATAAGATACACCTGCAAAGGCGGCA
CAACCCCAGTGCCACGTTGTGAGTTGGATAGTTGTGGAAAGAGTCAAATGGCTCTCCTC
AAGCGTATTCAACAAGGGGCTGAAGGATGCCCAGAAGGTACCCCATTGTATGGGATCTG
ATCTGGGGCCTCGGTGCACATGCTTTACATGTGTTTAGTCGAGGTTAAAAAAACGTCTAG
GCCCCCCGAACCACGGGGACGTGGTTTTCCTTTGAAAAACACGATGATAATATGGCCAC
AACC*ATGGTGAGCAAGGGCGAGGAGCTGTTCACCGGGGTGGTGCCCATCCTGGTCGAGC*
*TGGACGGCGACGTAAACGGCCACAAGTTCAGCGTGTCCGGCGAGGGCGAGGGCGATGCC*
*ACCTACGGCAAGCTGACCCTGAAGTTCATCTGCACCACCGGCAAGCTGCCCGTGCCCTGG*
*CCCACCCTCGTGACCACCCTGACCTACGGCGTGCAGTGCTTCAGCCGCTACCCCGACCAC*
*ATGAAGCAGCACGACTTCTTCAAGTCCGCCATGCCCGAAGGCTACGTCCAGGAGCGCACC*
*ATCTTCTTCAAGGACGACGGCAACTACAAGACCCGCGCCGAGGTGAAGTTCGAGGGCGAC*

Figure 33 (cont.)

*ACCCTGGTGAACCGCATCGAGCTGAAGGGCATCGACTTCAAGGAGGACGGCAACATCCTG*
*GGGCACAAGCTGGAGTACAACTACAACAGCCACAACGTCTATATCATGGCCGACAAGCAG*
*AAGAACGGCATCAAGGTGAACTTCAAGATCCGCCACAACATCGAGGACGGCAGCGTGCAG*
*CTCGCCGACCACTACCAGCAGAACACCCCCATCGGCGACGGCCCCGTGCTGCTGCCCGA*
*CAACCACTACCTGAGCACCCAGTCCGCCCTGAGCAAAGACCCCAACGAGAAGCGCGATCA*
*CATGGTCCTGCTGGAGTTCGTGACCGCCGCCGGGATCACTCTCGGCATGGACGAGCTGTA*
*CAAGTAA*AGCGGCCGCGACTCTAGATCATAATCAGCCATACCACATTTGTAGAGGTTTTAC
TTGCTTTAAAAAACCTCCCACACCTCCCCCTGAACCTGAAACATAAAATGAATGCAATTGTT
GTTGTTAACTTGTTTATTGCAGCTTATAATGGTTACAAATAAAGCAATAGCATCACAAATTTC
ACAAATAAAGCATTTTTTTCACTGCATTCTAGTTGTGGTTTGTCGTCGACCTGCAG
TCAAACTCTAATGACCACATCTTTTTTAGAGATGAAAAATTTTCCACATCTCCTTTTGTAG
ACACGACTAAACATTTTGCAGAAAAAAGTTTATTAGTGTTTAGATAATCGTATACTTCATC
AGTGTAGATAGTAAATGTGAACAGATAAAAGGTATTCTTGCTCAATAGATTGGTAAATTC
CATAGAATATATTAATCCTTTCTTCTTGAGATCCCACATCATTTCAACCAGAGACGT
TTTATCCAATGATTTACCTCGTACTATACCACATACAAAACTAGATTTTGCAGTGACGTCG
TATCTGGTATTCCTACCAAACAAAATTTTACTTTTAGTTCTTTTAGAAAATTCTAAGGTAGA
ATCTCTATTTGCCAATATGTCATCTATGGAATTACCACTAGCAAAAAATGATAGAAATATA
TATTGATACATCGCAGCTGGTTTTGATCTACTATACTTTAAAAACGAATCAGATTCCATAA
TTGCCTGTATATCATCAGCTGAAAAACTATGTTTTACACGTATTCCTTCGGCATTTCTTTTT
AATGATATATCTTGTTTAGACAATGATAAAGTTATCATGTCCATGAGAGACGCGTCTCCGT
ATCGTATAAATATTTCATTAGATGTTAGACGCTTCATTAGGGGTATACTTCTATAAGGTTT
CTTAATCAGTCCATCATTGGTTGCGTCAAGAAC
tactatcggatgttgttgggtatctctagtgttacacatggccttactaaagtttgggtaaataactatgatatctctattaattatagatgcata
tatttcatttgtcaaggatattagtatcgacttgctatcgtcattaatacgtgtaatgtaatcatataaatcatgcgatagccaaggaaaattt
aaatagatgttcatcatataatcgtcgctataattcatattaatacgttgacattgactaatttgtaatatagcctcgccacgaagaaagctc
tcgtattcagtttcatcgataaaggataccgttaaatataactggttgccgatagtctcatagtctattaagtggtaagtttcgtacaaatac
agaatccctaaaatattatctaatgttggattaatctttaccataactgtataaaatggagacggagtcataactattttaccgtttgtactta
ctggaatagacgaaggaataatctccggacatgctggtaaagacccaaatgtctgtttgaagaaatccaatgttccaggtcctaatctc
ttaacaaaaattacgatattcgatcccgatatcctttgcattctatttaccagcatatcacgaactatattaagattatctatcatgtctattctc
ccaccgttatataaatcgcctccgctaagaaacgttagtatatccatacaatggaatacttcatttctaaaatagtattcgttttctaattcttt
aatgtgaaatcgtatactagaaagggaaaaattatctttgagttttccgttagaaaagaaccacgaaactaatgttctgattgcgtccgat
tccgttgctgaattaatggatttacaccaaaaactcatataacttctagatgtagaagcattcgctaaaaaattagtagaatcaaaggat
ataagtagatgttccaacaagtgagcaattcccaagatttcatctatatcattctcgaatccgaaattagaaattcccaagtagatatcctt
tttcatccgatcgttgatgaaaatacgaacttattcggtaagacaatcatatggaaaagaatttaccagatatcttcttttttccaaactgcg
ttaatgtattctcttacaaatattcacaagatgaattcagtaatatgagtaaaacggaacgtgatagtttctcattggcggtgtttccagttat
aaaacatagatggcataacgcacacgttgtaaaacataaaggaatatacaaagttagtacagaagcacgtggaaaaaagtatct
cctccatcactaggaaaacccgcacacataaacctaaccgcgaagcaatatatatacagtgaacacacaataagctttgaatgttat
agttttctaaaatgtataacaaatacagaaatcaattcgttcgatgagtatatattaagaggactattagaagctggtaatagtttacagat
attttccaattccgtaggtaaacgaacagatactataggtgtactagggaataagtatccatttagcaaaattccattggcctcattaactc
ctaaagcacaacgagagatattttcagcgtggatttctcatagacctgtagttttaactggaggaactggagtgggtaagacgtcacag
gtacccaagttattgctttggtttaattatttatttggtggattctctactctagataaaatcactgactttcacgaaagaccagtcattctatctc
ttcctaggatagctttagttagattgcatagcaataccatttaaaatcattgggatttaaggtactagatggatctcctatttctttacggtac
ggatctataccggaagaattaataaacaaacaaccaaaaaaatatggaattgtatttctacccataagttatctctaacaaaactattt
agttatggcactcttattatagacgaagttcatgagcatgatcaaataggagatattattatagcagtagcgagaaagcatcatacgaa
aatagattctatgttttaatgactgccacgttagaggatgacagggaacggctaaaagtatttttacctaatcccgcatttatacatattcct
ggagatacactgtttaaaattagcgaggtatttattcataataagataaatccatcttccagaatggcatacatagaagaagaaaagag
aaatttagttactgctatacagatgtatactcctcctgatggatcatccggtatagtcttgtggcatccgttgcacagtgtcacgaatataa
atcatatttagaaaaaagattaccgtatgatatgtatattattcatggtaaggtcttagatatagacgaaatattagaaaagtgtattcatc
acctaatgtatcgataattatttctactccttatttggaatccagcgttactatacgcaatgttacacacatttatgatatgggtagagttttgtc
cccgctccttttggaggatcgcaagaatttatttctaaatctatgagagatcaacgaaaaggaagagtaggaagagttaat (SEQ ID NO: 27)

Figure 34 (cont.)
C
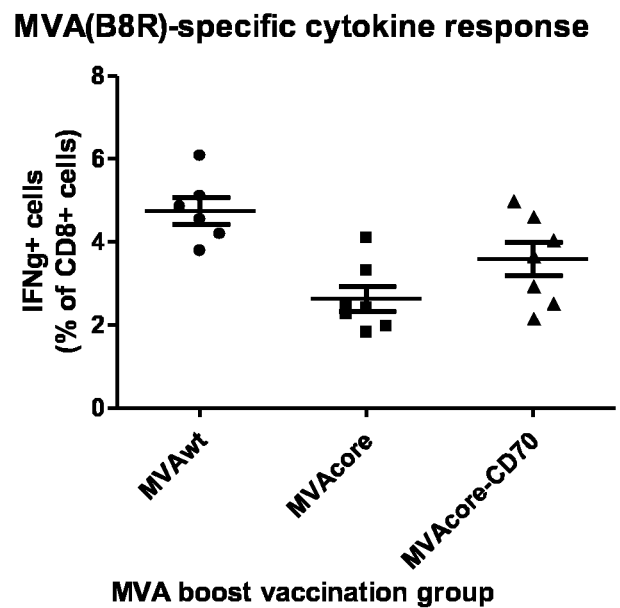
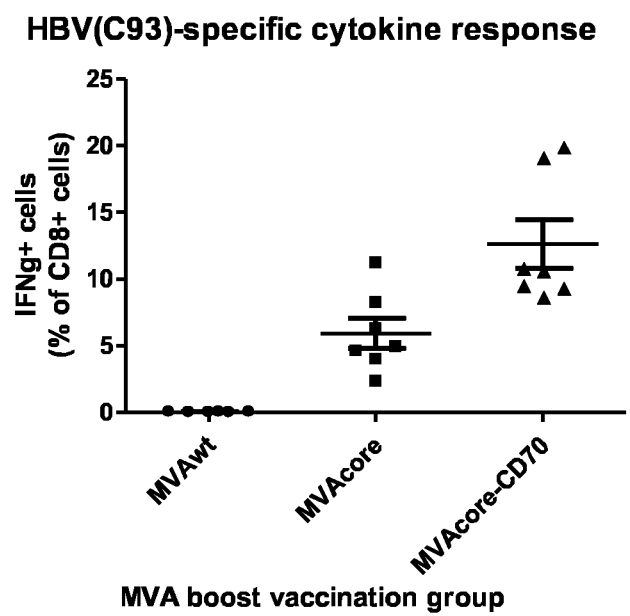

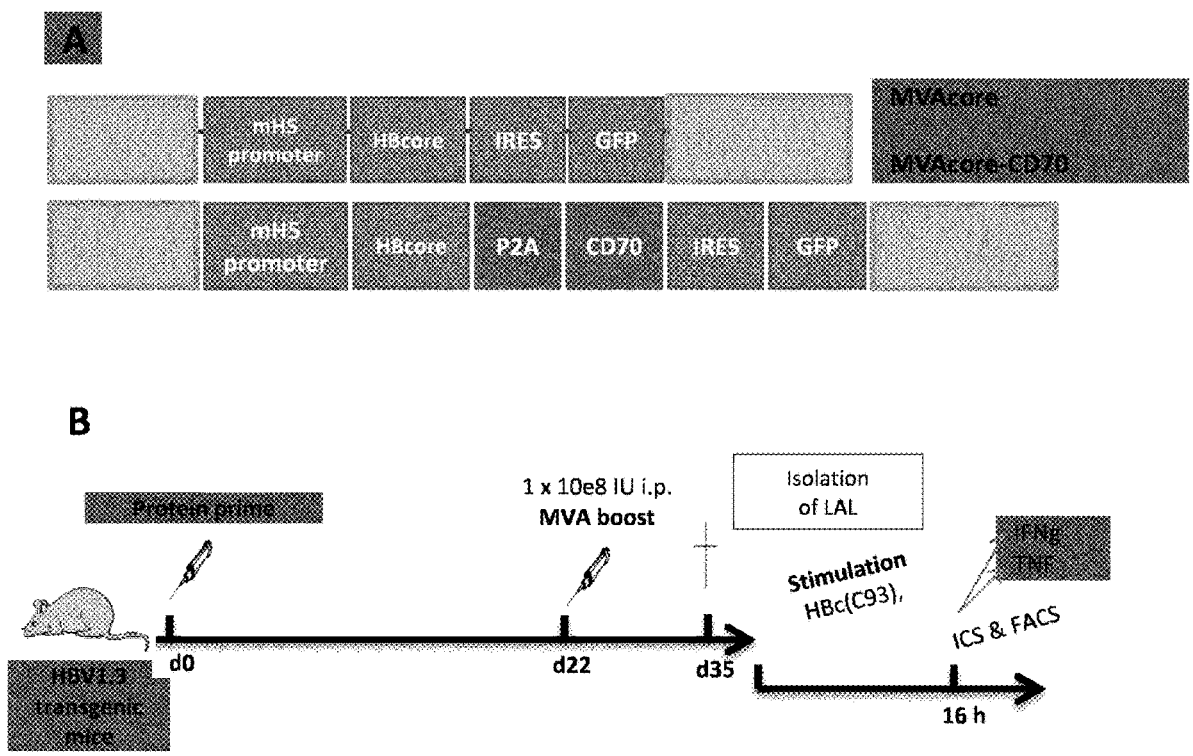

MEANS AND METHODS FOR TREATING HBV

CROSS-REFERENCE TO RELATED APPLICATION

This application is a U.S. national phase application filed under 35 U.S.C. § 371 claiming benefit to PCT International Patent Application No. PCT/EP2017/050553, filed on Jan. 12, 2017, which claims priority to Luxembourg Patent Application No. 92942, filed on Jan. 12, 2016, the disclosure of which is incorporated herein by reference in its entirety.

FIELD OF INVENTION

The present invention relates to an improved recombinant vaccination vector for the treatment or vaccination against hepatitis B virus (HBV) as well as pharmaceutical compositions or vaccines comprising said recombination. The present invention also relates to a recombinant vaccination vector for use in a method of vaccination against HBV, as well as kits for the vaccination against HBV.

BACKGROUND

More than 240 million humans are suffering from chronic Hepatitis B virus (HBV)-infection. Approved treatment options are nucleos(t)ide analogs and interferon α. Nucleos(t)ide analogs control but do not cure hepatitis B and require expensive long-term treatment potentially associated with the emergence of resistant viruses. Interferon α therapy is limited by side-effects and is only curative in 15-20% of patients.

The virus is divided into four major serotypes (adr, adw, ayr, ayw) that induce differential antibody responses based on antigenic epitopes present on its envelope proteins, and into (at least) eight genotypes (A-I) according to overall nucleotide sequence variation of the genome. The genotypes have a distinct geographical distribution and are used in tracing the evolution and transmission of the virus. Differences between genotypes affect the disease severity, course and likelihood of complications, and response to treatment and possibly vaccination. Furthermore, subgenotypes, e.g. A1-5, exist. In Central Europe and the United States, the predominant genotype is A2. However, only 1% of the infected humans carry the A2 subgenotype, while the majority of patients carry HBV of the genotype B, C, or D. It has been shown that conventional HBV vaccines provide a better protection against HBV of the same (sub)genotype as the HBV antigens comprised in the vaccine than to other (sub)genotypes.

It is well established that the host adaptive immune system is essential for efficient HBV control. Neutralizing antibodies directed against the HBV small surface antigen (HBsAg) prevent virus spread to non-infected hepatocytes and seroconversion from HBsAg to anti-HBs represents the clinical endpoint of HBV-infection (Rehermann and Nascimben, Nat Rev Immunol 2005; 5:215-29). Patients clearing the virus develop strong polyclonal and multispecific CD8+ and CD4+ T-cell responses whereas chronic infection is associated with depletion and progressive dysfunction of antiviral T-cells (Rehermann et al., J Exp Med 1995; 181: 1047-58) The clinical observation that chronic HBV-infection resolved in bone marrow transplant recipients that obtained bone marrow from HBV immune donors supports a strong role for T-cells in controlling the infection (Ilan et al., Gastroenterology 1993; 104:1818-21). Based on these observations, therapeutic vaccinations were designed to activate endogenous HBV-specific T-cell responses. However, numerous clinical attempts in chronically infected patients only had transient effects on anti-HBV immune responses and failed to control HBV (Kutscher et al., Microb Biotechnol 2012; 5:270-82). Continued exposure to high levels of circulating viral antigens seems to be a major hurdle for immunotherapeutic approaches because they induce tolerance and effector cell dysfunction.

Also, combining therapeutic vaccination with antiviral treatment, that controls viremia but has no effect on circulating antigen levels, did not improve vaccine efficacy and clinical outcome (Michel et al., J Hepatol 2011; 54:1286-96).

In order to facilitate the development of new immunotherapeutic strategies, HBV-transgenic mice (HBVtg), a model of vertically transmitted chronic HBV-infection has been developed (Guidotti et al., J Virol 1995; 69:6158-69). HBVtg mice replicate HBV in hepatocytes, produce HBcAg, HBsAg and hepatitis B e antigen (HBeAg) and release infectious virus into the blood (Guidotti et al., J Virol 1995; 69:6158-69). Expression of HBV antigens starts around birth and mice are immunologically tolerant to HBV-encoded proteins (Shimizu et al., J Immunol 1998; 161:4520-9), but this tolerance can be broken (Buchmann et al., Vaccine 2013; 31:1197-203).

Modified Vaccinia virus Ankara (MVA) is related to vaccinia virus, a member of the genera Orthopoxvirus, in the family of Poxviridae. MVA was generated by 516 serial passages on chicken embryo fibroblasts of the Ankara strain of vaccinia virus (CVA) (for review see Mayr, A., et al. Infection 3, 6-14 (1975)). As a consequence of these long-term passages, the genome of the resulting MVA virus had about 31 kilobases of its genomic sequence deleted and, therefore, was described as highly host cell restricted for replication to avian cells (Meyer, H. et al., J. Gen. Virol. 72, 1031-1038 (1991)). It was shown in a variety of animal models that the resulting MVA was significantly avirulent (Mayr, A. & Danner, K., Dev. Biol. Stand. 41: 225-34 (1978)) but still raised protective immune responses against poxviruses. Therefore, this MVA strain has been tested in clinical trials as a vaccine to immunize against the human smallpox disease (Mayr et al., Zbl. Bakt. Hyg. I, Abt. Org. B 167, 375-390 (1987); Stickl et al., Dtsch. med. Wschr. 99, 2386-2392 (1974)). These studies involved over 120,000 humans, including high-risk patients, and proved that, compared to vaccinia-based vaccines, MVA had diminished virulence and was well tolerated, while it still induced a good specific immune response.

In the following decades, MVA was engineered for use as a viral vector for recombinant gene expression or as a recombinant vaccine (Sutter, G. et al., Vaccine 12: 1032-40 (1994)). Strains of MVA for the development of vaccines or pharmaceuticals, have been described. See U.S. Pat. Nos. 6,761,893 and 6,193,752. Such strains are capable of reproductive replication in distinct non-human cells and cell lines, especially in chicken embryo fibroblasts (CEF), but are not capable of significant reproductive replication in human cell lines known to permit replication of other known vaccinia strains.

Based on the above, there is a need in the art for improved means and methods that can be used in therapeutic vaccination against HBV. These means and methods should in parallel induce neutralizing antibody responses and a multi-specific T cell response directed to multiple subtypes of HBV.

DETAILED DESCRIPTION

The present invention relates to a novel recombinant vaccination vector for the treatment or vaccination against hepatitis B virus (HBV) as well as pharmaceutical compositions or vaccines comprising said MVA. The present invention also relates to a vaccination method against HBV using recombinant MVA. The means and methods of the present invention are envisaged to induce both an antibody response as well as a T cell response against HBV in a subject, and it is further envisioned that the induced immune response is effective against a broad variety of HBV genotypes and serotypes.

A "recombinant vaccination vector" as used herein refers to an attenuated virus or bacterium. In this context, "vector" refers to the virus or bacterium used as the carrier. Typically, this attenuated virus or bacterium is used to introduce nucleic acid encoding for antigens to cells of the subject A recombinant vaccination vector of the invention may be an attenuated *Salmonella* strain. However, alternatively other prokaryotic microorganisms such as attenuated strains of *Escherichia coli, Shigella, Yersinia, Lactobacillus, Mycobacteria, Listeria* or *Vibrio* could be used. Examples of suitable strains of microorganisms include *Salmonella typhimurium, Salmonella typhi, Salmonella dublin, Salmonella enteretidis, Shigella flexeneri, Shigella sonnel*. Attenuated *Salmonella* strains are one of the best characterized mucosal vaccine carriers. Recombinant *Salmonella* strains that are attenuated yet invasive have been used as oral vaccine vectors to carry protective epitopes of several pathogens into the mucosal associated lymphoid tissue thus inducing mucosal, systemic and CTL immune responses against both the carrier and the foreign antigens.

Further, a recombinant vaccination vector of the invention may be an attenuated *Salmonella* strain, a CMV-, a VSV-based vector, an Adenoviral vector or a Measles vector.

A recombinant vaccination vector of the invention may be a viral vector that may be a viral particle having infectivity, which is also a carrier for introducing a gene into a cell. Viral vaccination vectors are familiar to the person skilled in the art. Particularly contemplated by the invention is a poxvirus vector. A recombinant poxvirus may be a poxvirus that is produced by standard genetic engineering methods. In a preferred embodiment, the recombinant vaccination vector of the invention is a MVA.

MVA is particularly suited as vector system. Its potency to be effective in inducing both humoral and cellular immune responses in a short period of time after vaccination against, for example, small pox virus has been demonstrated. Its safety has been established. Its potency to even induce an immune response in immune-compromised subjects is known.

However, apart from the advantages that MVA does have for use as a vaccine against HBV, the greatest challenge for a HBV vaccine is that it is able to induce both a humoral as well as a cellular immune response and that this immune response is preferably directed to multiple genotypes and/or serotypes of HBV. The choice of the vector, the vaccination scheme and the HBV antigens may all contribute to the effectiveness of the vaccination.

The present invention encompasses the use of a combination of HBV antigens from different HBV genotypes and/or serotypes. This combination not only led to a broad immune response against multiple HBV strains but also to a stronger immune response against each HBV genotype compared to vaccines comprising only antigens from a single HBV genotype. In fact, using the means and methods of the current invention, the inventors were even able to overcome immune tolerance in subjects with low, medium and even high antigen levels.

MVA-based vaccines are advantageous for several reasons. For example, the preferred MVA strain, MVA-F6 (Sutter and Staib, 2003. Curr. Drug Targets Infect. Disord. 3:263-271), grows well in primary Chicken Embryo Fibroblast (CEF) cells and does not replicate in human cells. In human cells, the viral genes as well as an engineered transgene are expressed, but no infectious virus is produced. The restricted host range of MVA may explain the non-virulent phenotype observed in vivo in a wide range of mammalian species including humans. MVA has been shown to be safe in numerous toxicity studies. Construction, production and use of recombinant MVA has been described in the art, for example in WO 97/02355, Sutter and Staib, 2003 (supra), and WO 2003/008533.

The present invention envisages recombinant vaccination vector, preferably a modified vaccinia virus Ankara (MVA), expressing one or more antigens from hepatitis B virus (HBV). The one or more antigens may be selected from an envelope protein (HBs-antigen) from HBV, a core protein (HBc-antigen) from HBV or a RT domain of a polymerase from HBV. The envelope protein may for example be an envelope protein of HBV serotype adw, such as of HBV genotype A serotype adw, such as of HBV genotype A2 serotype adw2. The core protein may for example be a core protein of HBV serotype ayw, such as of HBV genotype D serotype ayw.

The recombinant vaccination vector, preferably MVA, of the present invention may express more than one envelope proteins, wherein the more than one envelope proteins may be from different genotypes or serotypes of HBV. For example, the MVA of the present invention may express an envelope protein of HBV genotype A serotype adw as well as an envelope protein of genotype C. Similarly, the MVA of the present invention may express more than one core proteins, wherein the more than one core proteins may be from different genotypes or serotypes of HBV. For example, the MVA of the present invention may express a core protein of HBV genotype D serotype ayw as well as a core protein of genotype C.

The recombinant vaccination vector, preferably MVA, of the present invention may also express a polymerase from HBV or a RT domain of the HBV polymerase. This polymerase can be of any genotype or serotype. The polymerase may preferably be a polymerase from HBV genotype D.

The recombinant vaccination vector, preferably MVA, of the present invention may express (a) an envelope protein (HBs-antigen) from hepatitis B virus serotype adw, wherein the envelope protein is preferably a large envelope or small envelope protein from hepatitis B virus genotype A serotype adw; preferably a small envelope protein and (b) a core protein (HBc-antigen) from hepatitis B virus serotype ayw, wherein the core protein is preferably from hepatitis B virus genotype D serotype ayw; and at least one of the following: (c) an envelope protein (HBs-antigen) from hepatitis B virus having at least 90% sequence identity to the amino acid sequence set forth in SEQ ID NO: 1, (d) a core protein (HBc-antigen) from hepatitis B virus having at least 90% sequence identity to the amino acid sequence set forth in SEQ ID NO: 2, and/or (e) an RT domain of a polymerase from hepatitis B virus having at least 90% sequence identity to the amino acid sequence set forth in SEQ ID NO: 3. It is understood that the MVA of the present invention may express three, preferably four or most preferably five antigens of HBV, such as the antigens (a), (b), (c), the antigens (a), (b), (d), or the antigens (a), (b), (e), the antigens (a), (b), (c), (d), the antigens (a), (b), (c), (e), the antigens (a), (b), (d), (e), or the antigens (a), (b), (c), (d), (e).

As used herein an "envelope protein", "HBs-antigen" or "HBsAg" of HBV refers to the surface antigen of the hepatitis B virus (HBV). The "envelope protein", "HBs-antigen" or "HBsAg" may relate on any one of the three variants, the small, middle, and large envelope protein, which are translated from distinct mRNAs. Common to all three variants, is the "a" determinant epitope that is located at codon positions 124 to 147 within the major hydrophilic region (MHR) of the S gene. This "a" determinant is one of the main targets of anti-HBs antibodies during the course of the initial immune response in acute hepatitis B. The term an "envelope protein", "HBs-antigen" or "HBsAg" may optionally relate to an immunogenic fragment of the envelope protein. An immunogenic fragment of an envelope protein relates to proteins or peptides derived from any full-length envelope protein that is N-terminally and/or C-terminally shortened, i.e. lacking at least one of the N-terminal and/or C-terminal amino acids. Such a fragment comprises preferably at least 70, preferably at least 80, preferably at least 90, preferably at least 100, more preferably at least 125, most preferably at least 150 consecutive amino acids of the primary sequence of an envelope protein and is usually immunogenic. Typically, such an immunogenic fragment comprises compared to the full length protein at least amino acids 99 to 168 corresponding to the amino acid positions of the small envelope protein.

As used herein, a "core protein" or "HBc-antigen" of HBV refers to the structural protein of the nucleocapsid. Full-length core protein is 183 amino acids in length and consists of an assembly domain (amino acids 1 to 149) and a nucleic acid-binding domain (amino acids 150 to 183). The 34-residue nucleic acid-binding domain is extremely basic, with 17 arginines, consistent with its function. Core protein is dimeric in solution; these dimers self-assemble into icoshedral capsids. It is understood that also truncated core proteins, comprising only amino acids 1 to 149 are capable of forming capsids. The term "core protein" or "HBc-antigen" may optionally relate to an immunogenic fragment of the core protein. An immunogenic fragment of a core protein relates to proteins or peptides derived from any full-length core protein that is N-terminally and/or C-terminally shortened, i.e. lacking at least one of the N-terminal and/or C-terminal amino acids. Such a fragment comprises preferably at least 100, more preferably 125, most preferably 149 or more consecutive amino acids of the primary sequence of a core protein and is usually immunogenic. Typically, such an immunogenic fragment comprises compared to the full length core protein at least amino acids 18 to 143 corresponding to the sequence positions set forth in SEQ ID NO: 11. A typical example is a core protein fragment that consists of amino acids 1 to 149 of the full-length core protein set forth in SEQ ID NO: 11.

As used herein, "immunogenic" refers to the ability of a particular substance, such as an antigen or epitope, to provoke an immune response in the body of a human or animal. In other words, immunogenicity is the ability to induce a humoral and/or cell mediated immune response. The ability of an antigen to elicit immune responses is called immunogenicity, which can be humoral and/or cell-mediated immune responses. Without wishing to be bound by theory, it is assumed that any naturally occurring HBs-antigen, HBc-antigen or polymerase from HBV is immunogenic. Also, it is assumed that many variants of naturally occurring HBs-antigen, HBc-antigen or polymerase from HBV, in which one or more amino acids are exchanged, deleted or inserted compared to the naturally occurring sequence. As an illustrative example, an immunogenic variant of a naturally occurring HBs-antigen is an HBs-antigen, in which the "a" determinant epitope has been replaced with the "a" determinant of an HBs-antigen of another serotype. Typically, an immunogenic variant of a naturally occurring HBs-antigen, HBc-antigen or polymerase may have 90% sequence identity with the amino acid sequence of the natural occurring HBs-antigen, HBc-antigen or polymerase.

The recombinant vaccination vector, preferably MVA, of the present invention comprises an envelope protein from hepatitis B virus serotype adw. Such an envelope protein may be a small, middle, or large envelope protein, with small or large envelope protein being preferred, with small envelope protein being most preferred. The envelope protein is preferably of genotype A, serotype adw (A/adw), preferably of HBV A2/adw2. However, any naturally occurring or engineered envelope protein having the immunogenicity of a natural occurring envelope protein of a HBV adw is suited for the present invention. Preferred envelope proteins comprise a sequence having at least about 90%, preferably at least about 91%, preferably at least about 92%, preferably at least about 93%, preferably at least about 94%, preferably at least about 95%, preferably at least about 96%, preferably at least about 97%, preferably at least about 98%, preferably at least about 99%, preferably about 100% sequence identity to the amino acid sequence set forth in SEQ ID NO: 08, or preferably comprises or consists of the amino acid sequence set forth in SEQ ID NO: 08. The envelope protein may also have additional amino acids at the N- or C-terminal end. Preferably, the envelope protein has 30 or less, preferably 25 or less, preferably 20 or less, preferably 15 or less, preferably 10 or less, preferably 5 or less, preferably 4 or less, preferably 3 or less, preferably 2 or less, preferably 1 or less, additional amino acids at the N- and/or C terminal end. These amino acids are preferably fragments of self-cleavage sites, such as P2A or T2A, which are described in Kim et al. 2011, PLoS ONE, 6(4):e18556. Thus, the envelope protein optionally comprises at the N-terminal end an additional prolin and/or at its C terminal end the additional sequence GSGATNFSLLKQAGDVEENPG (SEQ ID NO: 09). The envelope protein may thus have a sequence set forth in SEQ ID NO: 10.

The recombinant vaccination vector, preferably MVA, of the present invention comprises a core protein from hepatitis B virus serotype ayw. The core protein is preferably of HBV genotype D/ayw. Any naturally occurring or engineered core protein having the immunogenicity of a natural occurring core protein of a HBV ayw is suited for the present invention. In preferred embodiments, the core protein is a fragment of a full-length core protein consisting of amino acids 1 to 149 of the full-length protein. Preferred core proteins comprise a sequence having at least about 90%, preferably at least about 91%, preferably at least about 92%, preferably at least about 93%, preferably at least about 94%, preferably at least about 95%, preferably at least about 96%, preferably at least about 97%, preferably at least about 98%, preferably at least about 99%, preferably about 100% sequence identity to the amino acid sequence set forth in SEQ ID NO: 11, or preferably comprises or consists of the amino acid sequence set forth in SEQ ID NO: 11. The core protein may also have additional amino acids at the N- or C-terminal end. Preferably, the core protein has 30 or less, preferably 25 or less, preferably 20 or less, preferably 15 or less, preferably 10 or less, preferably 5 or less, preferably 4 or less, preferably 3 or less, preferably 2 or less, preferably 1 or less, additional amino acids at the N- and/or C terminal end. These amino acids are preferably fragments of self-cleavage sites, such as P2A or T2A. Thus, the core protein optionally comprises at the N-terminal end an additional prolin and/or at its C terminal end the additional sequence set forth in SEQ ID NO: 12. A fragment of the core protein consisting of full length amino acids 1 to 149 and having a C terminal sequence as described herein is considered to still have the ability to assemble to capsids and the additional C-terminal sequence is supposed to not interfere with capsid formation.

The recombinant vaccination vector, preferably MVA, of the present invention may comprise an immunogenic envelope protein (HBs-antigen) from hepatitis B virus having at least about 90%, preferably at least about 91%, preferably at least about 92%, preferably at least about 93%, preferably at least about 94%, preferably at least about 95%, preferably at least about 96%, preferably at least about 97%, preferably at least about 98%, preferably at least about 99%, preferably about 100% sequence identity sequence identity to the amino acid sequence set forth in SEQ ID NO: 01. SEQ ID NO: 01 is a consensus sequence of large envelope proteins of genotype C strains, which was generated based on an alignment of 500 HBV sequences representing the worldwide distribution of HBV strains. An illustrative example of a immunogenic envelope protein having at least about 90% sequence identity to the amino acid sequence set forth in SEQ ID NO: 04, having 99% sequence identity to SEQ ID NO: 1, which corresponds to the sequence set forth in derived from the putative prepre-S protein of HBV with the GenBank accession number ABV02797 (version ABV02797.1 GI:157057635 of 12 Sep. 2007), in which the A-determinant (the most important target sequence for anti-HBs antibodies) was modified to ayw (for formation of antibodies directed against serotype ayw) by exchanging 2 amino acids. The existence of a HBV-strain with essentially the same sequence as SEQ ID NO: 04 ensures that essential processes (folding/processing/presentation) are functional for the encoded protein. Hence, also contemplated by the invention is that the immunogenic envelope protein having at least about 90% sequence identity to the amino acid sequence set forth in SEQ ID NO: 1 is an envelope protein having at least about 90%, preferably at least about 91%, preferably at least about 92%, preferably at least about 93%, preferably at least about 94%, preferably at least about 95%, preferably at least about 96%, preferably at least about 97%, preferably at least about 98%, preferably at least about 99%, preferably about 100% sequence identity sequence identity to the amino acid sequence set forth in SEQ ID NO: 04. Moreover, the consensus sequence for envelope proteins of genotype C strains is highly similar to the consensus sequence for envelope proteins of genotype B strains. Since the immunogenic envelope protein is based on the envelope protein consensus sequence for genotype C strains, which is at the same time very similar to the consensus sequence for the envelope protein of genotype B strains, this immunogenic envelope protein is capable of inducing an immune response against a broad spectrum of at least genotype B and genotype C strains. It is understood that the immunogenic envelope protein having at least 90% sequence identity to the amino acid sequence set forth in SEQ ID NO: 1 optionally also refers to an immunogenic fragment thereof that has at least 90%, preferably at least about 91%, preferably at least about 92%, preferably at least about 93%, preferably at least about 94%, preferably at least about 95%, preferably at least about 96%, preferably at least about 97%, preferably at least about 98%, preferably at least about 99%, preferably about 100% sequence identity to the corresponding fragment of SEQ ID NO: 1. The envelope protein may also have additional amino acids at the N- or C-terminal end. Preferably, the envelope protein has 30 or less, preferably 25 or less, preferably 20 or less, preferably 15 or less, preferably 10 or less, preferably 5 or less, preferably 4 or less, preferably 3 or less, preferably 2 or less, preferably 1 or less, additional amino acids at the N- and/or C terminal end. These amino acids are preferably fragments of self-cleavage sites, such as P2A or T2A. Thus, the envelope protein optionally comprises at the N-terminal end an additional prolin and/or at its C terminal end the additional sequence GSGEGRGSLLTCGDVEENPG (SEQ ID NO: 13). The envelope protein may thus have a sequence set forth in SEQ ID NO: 14.

The recombinant vaccination vector, preferably MVA, of the present invention may also comprise an immunogenic core protein (HBc-antigen) from hepatitis B virus having at least about 90%, preferably at least about 91%, preferably at least about 92%, preferably at least about 93%, preferably at least about 94%, preferably at least about 95%, preferably at least about 96%, preferably at least about 97%, preferably at least about 98%, preferably at least about 99%, preferably about 100% sequence identity to the amino acid sequence set forth in SEQ ID NO: 2. SEQ ID NO: 2 is a consensus sequence of core proteins of genotype C strains that was generated based on alignment of 500 HBV-sequences representing the worldwide distribution of HBV strains. An illustrative example of a immunogenic core protein having at least about 90% sequence identity to the amino acid sequence set forth in SEQ ID NO: 05, having 100% sequence identity to SEQ ID NO: 2, which is essentially identical to the sequence derived from the capsid protein of HBV with the GenBank accession number NP_647607 (version NP_647607.1 GI:21326588 of 9 Jul. 2015). Hence, also contemplated by the invention is that the immunogenic core protein having at least about 90% sequence identity to the amino acid sequence set forth in SEQ ID NO: 2 is an envelope protein having at least about 90%, preferably at least about 91%, preferably at least about 92%, preferably at least about 93%, preferably at least about 94%, preferably at least about 95%, preferably at least about 96%, preferably at least about 97%, preferably at least about 98%, preferably at least about 99%, preferably about 100% sequence identity sequence identity to the amino acid sequence set forth in SEQ ID NO: 05. In addition, the consensus sequence for genotype C strains is identical to the consensus sequence of genotype B strains. Since the immunogenic envelope protein is based on the envelope protein consensus sequence for genotype C strains, which is identical to the consensus sequence for the envelope protein of genotype B strains, this immunogenic envelope protein is capable of inducing an immune response against a broad spectrum of at least genotype B and genotype C strains. It is understood that the immunogenic core protein having at least about 90% sequence identity to the amino acid sequence set forth in SEQ ID NO: 2 optionally also refers to an immunogenic fragment thereof that has at least 90% preferably at least about 91%, preferably at least about 92%, preferably at least about 93%, preferably at least about 94%, preferably at least about 95%, preferably at least about 96%, preferably at least about 97%, preferably at least about 98%, preferably at least about 99%, preferably about 100% sequence identity to the corresponding fragment of SEQ ID NO: 2. As an illustrative example, such an immunogenic fragment may be a fragment having 90% sequence identity to amino acids 1 to 149 of SEQ ID NO: 2. The core protein may also have additional amino acids at the N- or C-terminal end. Preferably, the core protein has 30 or less, preferably 25 or less, preferably 20 or less, preferably 15 or less, preferably 10 or less, preferably 5 or less, preferably 4 or less, preferably 3 or less, preferably 2 or less, preferably 1 or less, additional amino acids at the N- and/or C terminal end. These amino acids are preferably fragments of self-cleavage sites, such as P2A or T2A. Thus, the core protein optionally comprises at the N-terminal end an additional prolin. The core protein may further optionally comprise its C terminal end an additional sequence as set forth in SEQ ID NO: 09 or 13. The core protein may thus have a sequence set forth in SEQ ID NO: 15.

The recombinant vaccination vector, preferably MVA, of the present invention may also comprise an immunogenic RT domain of a polymerase from hepatitis B virus having at least about 90% preferably at least about 91%, preferably at least about 92%, preferably at least about 93%, preferably at least about 94%, preferably at least about 95%, preferably at least about 96%, preferably at least about 97%, preferably at least about 98%, preferably at least about 99%, preferably about 100% sequence identity to the amino acid sequence set forth in SEQ ID NO: 3. SEQ ID NO: 3 is a consensus sequence of RT domains of genotype A, B, C, and D strains that was generated based on alignment of 500 HBV-sequences representing the worldwide distribution of HBV strains. An illustrative example for such an immunogenic RT domain of a polymerase is a protein with the amino acid sequence set forth in SEQ ID NO: 6, which has 97% sequence identity to SEQ ID NO: 3. SEQ ID NO: 6 corresponds to the amino acid sequence of a RT domain of a polymerase derived from the partial polymerase of HBV with the GenBank accession number AFY09280 (version AFY09280.1 GI:425891330 of 31 Jan. 2013). SEQ ID NO: 6 is a typical example because it is the naturally occurring RT domain of a polymerase that has the highest similarity to the generated consensus sequence of genotypes A, B, C and D. The existence of a HBV-strain with this sequence ensures that essential processes (folding/processing/presentation) are functional for the encoded RT-domain. Hence, also contemplated by the invention is that the immunogenic RT domain having at least about 90% sequence identity to the amino acid sequence set forth in SEQ ID NO: 3 is an envelope protein having at least about 90%, preferably at least about 91%, preferably at least about 92%, preferably at least about 93%, preferably at least about 94%, preferably at least about 95%, preferably at least about 96%, preferably at least about 97%, preferably at least about 98%, preferably at least about 99%, preferably about 100% sequence identity to the amino acid sequence set forth in SEQ ID NO: 06. Since the RT domain of the polymerase comprises several highly conserved epitopes and since the RT domain of the polymerase comprised in the MVA of the invention is based on the RT domain consensus sequence for genotype A, B, C, and D strains, this immunogenic RT domain of a polymerase is capable of inducing an immune response against a broad spectrum of at least genotype A, B, C, and D strains. The present invention also envisions that the RT domain of a polymerase can be comprised in a full-length polymerase. Thus, also a full length polymerase or a truncated full-length polymerase comprising the immunogenic RT domain is within the scope of the invention. It is understood that the immunogenic RT domain of a polymerase having at least 90% sequence identity to the amino acid sequence set forth in SEQ ID NO: 3 optionally also refers to an immunogenic fragment thereof that has at least about 90% preferably at least about 91%, preferably at least about 92%, preferably at least about 93%, preferably at least about 94%, preferably at least about 95%, preferably at least about 96%, preferably at least about 97%, preferably at least about 98%, preferably at least about 99%, preferably about 100% sequence identity to the corresponding fragment of SEQ ID NO: 3. The RT domain of the polymerase may also have additional amino acids at the N- or C-terminal end. Preferably, the RT domain has 30 or less, preferably 25 or less, preferably 20 or less, preferably 15 or less, preferably 10 or less, preferably 5 or less, preferably 4 or less, preferably 3 or less, preferably 2 or less, preferably 1 or less, additional amino acids at the N- and/or C terminal end. These amino acids are preferably fragments of self-cleavage sites, such as P2A or T2A. Thus, the RT domain optionally comprises at the N-terminal end an additional prolin. The core protein may further optionally comprise its C terminal end an additional sequence as set forth in SEQ ID NO: 13. The RT domain may thus have a sequence set forth in SEQ ID NO: 16.

The recombinant vaccination vector as described herein, preferably MVA, may also comprise or further express a CD70 molecule. Preferably the CD70 is a human CD70.

CD70 is the ligand for CD27, and is also known as CD27L. It is a type II transmembrane protein and is expressed on highly activated lymphocytes (like in T- and B-cell lymphomas) Further it is expressed on renal cell carcinoma and is evaluated as a tumor target). CD70 ligand expression is normally closely regulated, however when CD27L is constitutively expressed on B cells an extensive and effective memory-like T cell pool develops (Arens, R. et al 2004 J Exp Med 199(11) 1595-605). In chronic viral infections, CD70 signalling may be relevant to outcome.

CD27/CD70 is a member of the tumor necrosis factor receptor/tumor necrosis factor ("TNFR/TNF") superfamily well known for their T-cell shaping properties. Among CD27/CD70, this family includes CD30/CD30L, CD40/CD40L, OX40/OX40L, 4-1BB/4-1BBL, GITR/GITRL and Fas/FasL. The role of CD70, among others such as OX40L and 4-1BBL for primary and secondary T-cell responses has been investigated in a broad range of infectious disease models [Hendrick et al., "CD27 is required for generation and long-term maintenance of T-cell immunity," Nature Immunol. 1(5):433-440 (2000); Matter et al., "Virus-induced polyclonal B-cell activation improves protective CTL memory via retained CD27 expression on memory CTL," Eur. J. Immunol. 35(11):3229-3239 (2005); A. Schildknecht et al., "Priming of CD8+ T-cell responses by pathogens typically depends on CD70-mediated interactions with dendritic cells," Eur. J. Immunol. 37(3):716-728 (2007)]. Interestingly, the up-regulation of co-stimulatory molecules including, among others, CD70 on dendritic cells ("DCs") can be induced by combined TLR/CD40 stimulation [Sanchez et al., "Combined TLR/CD40 stimulation mediates potent cellular immunity by regulating dendritic cell expression of CD70 in vivo," J. Immunol. 178(3):1564-1572 (2007)].

Hence, also contemplated by the invention is that the CD70 has at least about 90%, preferably at least about 91%, preferably at least about 92%, preferably at least about 93%, preferably at least about 94%, preferably at least about 95%, preferably at least about 96%, preferably at least about 97%, preferably at least about 98%, preferably at least about 99%, preferably about 100% sequence identity to the amino acid sequence set forth in SEQ ID NO: 26.

The recombinant vaccination vector, preferably MVA, of the present invention is optimized for therapeutic vaccination against a broad HBV spectrum and comprises antigenic sequences from several frequently occurring HBV genotypes. This MVA is therefore capable of inducing an immune response against HBV of different genotypes and serotypes.

The inventors of the present invention have surprisingly found that compared to a MVA vaccine that only comprises HBV D/ayw antigen(s), the combination of an HBs-antigen from HBV A/adw with a HBc-antigen from HBV D/ayw will not only induce a broad immune response against HBV of genotypes A and D, but will also induce an even stronger T cell response against HBV D/ayw. Furthermore, the MVA of the present invention may also express an HBs-antigen or an HBc-antigen which are based on the consensus sequence of genotype C HBV strains. These consensus sequences of genotype C HBV strains are furthermore either highly similar or even identical to the consensus sequence of genotype B strains. This means that the MVA of the present invention comprising one or both of these sequences will further induce a broad immune response against at least genotype B and genotype C strains. In addition, the MVA of the present invention may express a RT domain of a polymerase that is based on the consensus sequence of genotype A, B, C, and D strains and which contains highly conserved antigens. Thus, introducing this RT domain to the MVA will further promote the induction of a broad immune response against HBV of the at least the genotypes A, B, C, and D. The MVA of the present invention is therefore an effective vaccine against MBV of at least genotypes A, B, C, and D.

The term "antigen" refers to a molecule which contains one or more epitopes that stimulate a host's immune system to make a cellular antigen-specific immune response, or a humoral antibody response. Antigens may include proteins, polypeptides, antigenic protein fragments and the like. Furthermore, the antigen can be derived from any known virus, bacterium, parasite, prion, plants, protozoans, or fungus and can be a whole organism. The term also includes tumor antigens. Synthetic antigens such as polyepitopes, flanking epitopes, and other recombinant or synthetically derived antigens are also included in this application. In a preferred embodiment, the antigen in the present invention is a polypeptide or protein.

In relation to the term "epitope", the term "antigen" refers to a (longer) sequence, in particular a (longer) amino acid sequence or protein sequence, whereas the phrase "antigenic epitope" or "an epitope of the antigen" encompasses a stretch of shorter sequence from the longer sequence. The term "antigen" thus encompasses epitopes. The term "antigen" also includes variants of proteins, polypeptides, and antigenic protein fragments as described herein. Also, the term "antigen" encompasses sequences identical to the native sequence as well as modification to the native sequence, such as deletions, additions, insertions and substitutions. Preferably, an antigen variant has at least about 50%, at least about 60% or 65%, at least about 70% or 75%, at least about 80%, 81%, 82%, 83%, 84%, 85%, 86%, 87%, 88%, or 89%, more typically, at least about 90%, 91%, 92%, 93%, or 94% and even more typically at least about 95%, 96%, 97%, 98% or 99%, most typically, at least about 99% amino acid identity with the reference antigen (i.e. the antigen from which it is derived).

An epitope, also termed herein as "antigenic epitope", forms part of the antigen that still elicit an immune response in a host. An epitope is, however, not limited to the exact sequence of the antigen from which it is derived. Thus, the term "epitope" encompasses sequences identical to the native sequence as well as modification to the native sequence, such as deletions, additions, insertions and substitutions. Preferably, an epitope variant have at least about 50%, at least about 60% or 65%, at least about 70% or 75%, at least about 80%, 81%, 82%, 83%, 84%, 85%, 86%, 87%, 88%, or 89%, more typically, at least about 90%, 91%, 92%, 93%, or 94% and even more typically at least about 95%, 96%, 97%, 98% or 99%, most typically, at least about 99% amino acid identity with the reference epitope (i.e. the epitope from which it is derived).

Techniques for determining sequence identity between two nucleic acids and amino acids are known in the art. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100.

"Percent (%) amino acid sequence identity" with respect to antigens or epitopes described herein is defined as the percentage of amino acid residues in a candidate sequence that are identical with the amino acid residues in the reference sequence (i.e. the antigen or epitope from which it is derived), after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared.

The same is applicable to "percent (%) nucleotide sequence identity", mutatis mutandis.

For example, an appropriate alignment for nucleic acid sequences is provided by the local homology algorithm of Smith and Waterman, (1981), Advances in Applied Mathematics 2: 482-489. This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov (1986), Nucl. Acids Res. 14(6): 6745-6763. An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.nih.gov/cgi-bin/BLAST.

The nucleic acids encoding for HBV antigens in the MVA of the invention may be comprised in individual expression cassettes, or preferably all together in a single expression cassette. The term "expression cassette" as used herein encompasses DNA as well as RNA sequences which are capable of directing expression of a particular nucleotide sequence in an appropriate host cell. In general, it comprises a promoter operably linked to a polynucleotide of interest, which is optionally operably linked to a termination signal and/or other regulatory elements. The expression cassette may comprise a transcription regulating nucleotide sequence. An expression cassette may also comprise sequences required for proper translation of the nucleotide sequence. The expression cassette may be one, which is naturally occurring but has been obtained in a recombinant form useful for heterologous expression. The coding region usually codes for a protein of interest. The expression cassette comprising the polynucleotide sequence of interest may also be chimeric, meaning that at least one of its components is heterologous with respect to at least one of its other components. Typically, the expression cassette herein is not naturally occurring (i.e., heterologous or exogenous or foreign) in the MVA genome and is capable of transcription in infected cells.

The expression of the nucleotide sequence in the expression cassette may be under the control of a constitutive promoter or of an inducible promoter, which initiates transcription only when the host cell is exposed to some particular external stimulus. In the expression cassettes of the present invention, the promoter is preferably a poxviral promoter. Such a poxviral promoter may be a natural occurring promoter or a synthetic promoter. As an illustrative example, the poxvirus promoter is a Pr7.5 promoter, a hybrid early/late promoter, a PrS promoter, a synthetic or natural early or late promoter such as one of the promoters described in WO 2010/102822 or in WO 2005/054484, or cowpox virus ATI promoter For example the poxviral promoter is P7.5 (SEQ ID NO: 17) (Endo et al. J Gen Virol. 1991 March; 72 (Pt 3):699-703). Preferred promoters, however, are promoters that are stronger than P7.5, for example the promoter PH5 as described in US 2011/0064769 having the sequence set forth in SEQ ID NO: 18.

Nucleic acid sequences encoding the antigen or an epitope thereof are preferably codon optimized. A "codon-optimized" nucleic acid sequence refers to a nucleic acid sequence containing codons that are replaced by codons preferred by the desired host cell, preferably a human host cell. A nucleic acid sequence is converted into a codon-optimized nucleic acid sequence having an identical translated polypeptide sequence, but with alternative codon usage, in particular using the most frequently codons of the targeted organism. The method of creating a codon-optimized nucleic acid sequence of an antigen generally includes identifying codons in the naturally occurring sequence of an antigen that are commonly not associated with high expressing genes in the target organism and replacing them with codons that are known to be widely used in gene expression of the target organism. A codon-optimized nucleic acid sequence may show improved expression over the naturally occurring sequence in the desired host cell. Whether a codon optimized sequence will induce an improvement in the protein production over the non-optimized sequence can be examined by a skilled person.

Codon optimization avoids the use of rare codons for a desired host, since rare codons may block or reduce expression of the encoded protein. Also, substitutions that may introduce nucleic acid signals for the desired host are preferably avoided. Such signals include, but are not limited to, splice signals, termination signals, and initiation signals. Preferably, the following sequence motifs are avoided depending on the type of vector utilized, e.g., the vaccinia virus early transcription termination signal needs not to be avoided in many other vectors, internal TATA-boxes, chi-sites, and ribosomal entry sites; AT-rich and GC-rich sequence stretches; ARE, INS, and CRS sequence elements; repeat sequences and RNA secondary structures; (cryptic) splice donor and acceptor sites, and branch points; and vaccinia early transcription termination signals: (TTTTTNT).

Techniques for codon optimization are known in the art. Substitution of nucleotides with different nucleotides refers to the technical or artificial replacement of nucleotides by other nucleotides. Preferably, substituted nucleotides do not alter the encoded amino acid sequence. Substitution can be performed by identifying codons in the two homologous nucleotide sequences encoding the same amino acids and altering codons in one of the two homologous nucleotide sequences such that the codons still encodes the same amino acids. The alterations can be made in one, both or all of the homologous nucleotide sequences.

The invention envisions that all HBV antigens are preferably translated as one single polypeptide chain comprising several antigens. On the polypeptide chain, antigen sequences are preferably separated by self-cleavage site sequences. Thus, the polypeptide chain comprising several antigens will be post-translationally cleaved to multiple polypeptide chains, wherein each of the multiple polypeptide chains may comprise a single HBV antigen. This approach has the advantage that all HBV antigens are expressed in about equimolar levels. A preferred arrangement for polypeptide chain comprising several antigens is—from N-terminus to C-terminus—an envelope protein from HBV A/adw, a P2A site, a core protein from HBV D/ayw, a P2A site, an immunogenic RT domain of a polymerase from hepatitis B virus as described herein, a T2A site, an immunogenic envelope protein (HBs-antigen) from hepatitis B as described herein, a T2A site, an immunogenic core protein (HBs-antigen) from hepatitis B as described herein. In a preferred embodiment, the polypeptide chain comprising several antigens comprises a sequence set forth in SEQ ID NO: 07. As depicted in FIG. 16B, the two different envelope proteins will be located in a cellular membrane and may be secreted as subviral particles. These subviral particles may comprise both envelope proteins that are from different HBV genotypes and may be taken up by antigen-presenting cells, which may increase the induced immune response. The core particles may form empty capsids, wherein the empty capsids may similarly comprise the core proteins that are from different HBV genotypes. Such a capsid will trigger an immune response against multiple HBV genotypes. The polymerase will be degraded in the proteasome and presented by in an HLA context. The arrangement described herein has further the advantage that most of the only partially processed proteins, i.e. proteins where a self-cleaving site has not been cleaved, will be incorporated into secreted virus-like particles which will assumingly increase the immune response, in particular enhance and broaden the adaptive immune response (cf. FIG. 18).

The invention encompasses a recombinant MVA comprising HBV genes incorporated in a variety of insertion sites in the MVA genome. "Variety of insertion sites" means HBV genes encoding HBV antigens, respectively, can be inserted into the same or one or more different insertion sites in the MVA genome, with the same insertion site being preferred. Different means that, for example, a first insertion site is not the same as a second insertion site.

As an illustrative example, the HBV genes may be inserted into intergenic regions (IGR) of the MVA. Such a IGR may be selected from IGR07/08, IGR 44/45, IGR 64/65, IGR 88/89, IGR 136/137, and IGR 148/149. However, it is preferred that the HBV genes are inserted into naturally occurring deletion sites I, II, III, IV, V, or VI of the MVA, wherein it is preferred that at least one or preferably all HBV gene(s) are inserted to naturally occurring deletion site III. As an illustrative example, all HBV genes may be comprised in a single expression cassette on a single open reading frame as described herein, wherein the single expression cassette is inserted into naturally occurring deletion site III.

The recombinant MVA virus can be generated by routine methods known in the art. Methods to obtain recombinant poxviruses or to insert exogenous coding sequences into a poxviral genome are well known to the person skilled in the art. For example, methods are described in the following references: Molecular Cloning, A laboratory Manual. Second Edition. By J. Sambrook, E. F. Fritsch and T. Maniatis. Cold Spring Harbor Laboratory Press. 2003: describes techniques for standard molecular biology techniques such as cloning of DNA, DNA and RNA isolation, western blot analysis, RT-PCR and PCR amplification techniques. Virology Methods Manual. Edited by Brian W J Mahy and Hillar O Kangro. Academic Press. 1996: describes techniques for the handling and manipulation of viruses. Molecular Virology: A Practical Approach. Edited by A J Davison and R M Elliott. The Practical Approach Series. IRL Press at Oxford University Press. Oxford 1993. Chapter 9: Expression of genes by Vaccinia virus vectors. Current Protocols in Molecular Biology. Publisher: John Wiley and Son Inc. 1998. Chapter 16, section IV: Expression of proteins in mammalian cells using vaccinia viral vector: describes techniques and know-how for the handling, manipulation and genetic engineering of MVA.

For the generation of recombinant poxviruses according to the present invention, different methods may be applicable. The DNA sequence to be inserted into the virus can be placed into an *E. coli* plasmid construct into which DNA homologous to a section of DNA of the poxvirus has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of poxviral DNA containing a non-essential locus. The resulting plasmid construct can be amplified by propagation within *E. coli* bacteria and isolated. The isolated plasmid containing the DNA gene sequence to be inserted can be transfected into a cell culture, e.g., chicken embryo fibroblasts (CEFs), along with infection of this culture by the poxvirus. Recombination between homologous poxviral DNA in the plasmid and the viral genome, respectively, can generate a poxvirus modified by the presence of foreign DNA sequences.

A cell of a suitable cell culture as, e.g., CEF cells, can be infected with a poxvirus. The infected cell can be, subsequently, transfected with a first plasmid vector comprising a foreign gene or genes, preferably under the transcriptional control of a poxvirus expression control element. As explained above, the plasmid vector also comprises sequences capable of directing the insertion of the exogenous sequence into a selected part of the poxviral genome. Optionally, the plasmid vector also contains a cassette comprising a marker and/or selection gene operably linked to a poxviral promoter. Suitable marker or selection genes are, e.g., the genes encoding the green fluorescent protein, β-galactosidase, neomycin-phosphoribosyltransferase or other markers. The use of selection or marker cassettes simplifies the identification and isolation of the generated recombinant poxvirus. However, a recombinant poxvirus can also be identified by PCR technology. Subsequently, a further cell can be infected with the recombinant poxvirus obtained as described above and transfected with a second vector comprising a second foreign gene or genes. In case, this gene can be introduced into a different insertion site of the poxviral genome, the second vector also differs in the poxvirus-homologous sequences directing the integration of the second foreign gene or genes into the genome of the poxvirus. After homologous recombination has occurred, the recombinant virus comprising two or more foreign genes can be isolated. For introducing additional foreign genes into the recombinant virus, the steps of infection and transfection can be repeated by using the recombinant virus isolated in previous steps for infection and by using a further vector comprising a further foreign gene or genes for transfection.

Alternatively, the steps of infection and transfection as described above are interchangeable, i.e., a suitable cell can at first be transfected by the plasmid vector comprising the foreign gene and, then, infected with the poxvirus. As a further alternative, it is also possible to introduce each foreign gene into different viruses, co-infect a cell with all the obtained recombinant viruses and screen for a recombinant including all foreign genes. A third alternative is ligation of DNA genome and foreign sequences in vitro and reconstitution of the recombined vaccinia virus DNA genome using a helper virus. A fourth alternative is homologous recombination in *E. coli* or another bacterial species between a vaccinia virus genome cloned as a bacterial artificial chromosome (BAC) and a linear foreign sequence flanked with DNA sequences homologous to sequences flanking the desired site of integration in the vaccinia virus genome.

Since the recombinant MVA virus according to the invention is highly replication restricted and, thus, highly attenuated, it is an ideal candidate for the treatment of a wide range of mammals including humans and even immune-compromised humans. Moreover, the production of MVA-based vaccines is more or less independent of existing production capacity for conventional vaccines, since MVA can be conveniently cultured in CEF cells. Thus, the MVA based vaccine of the present invention can be produced in large amounts in a short period of time. Furthermore, the MVA vector vaccines of the present invention can deliver multiple HBV antigens and thus allows for simultaneous induction of high level humoral and cellular immunity. Hence, the present invention also provides a pharmaceutical composition and also a vaccine for inducing an immune response in a living animal body, including a human.

The vaccine preferably comprises MVA viruses in a concentration range of $10^4$ to $10^9$ $TCID_{50}$/ml, preferably in a concentration range of $10^5$ to $5\times10^8$ $TCID_{50}$/ml, more preferably in a concentration range of $10^6$ to $10^8$ $TCID_{50}$/ml, and most preferably in a concentration range of $10^7$ to $10^8$ $TCID_{50}$/ml.

A preferred vaccination dose for humans comprises $10^6$ to $10^9$ TCID$_{50}$, most preferably a dose of $10^6$ TCID$_{50}$ or $10^7$ TCID$_{50}$ or $10^8$ TCID$_{50}$.

The pharmaceutical composition may generally include one or more pharmaceutically acceptable and/or approved additives like carriers, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

The term "pharmaceutically acceptable" means a non-toxic material that does not interfere with the effectiveness of the biological activity of the MVA according to the present invention. The characteristics of the carrier will depend on the route of administration. The pharmaceutical composition may further contain other agents which either enhance the activity or use in treatment. Such additional factors and/or agents may be included in the pharmaceutical composition to be applied for the method for immunization according to the present invention to produce a synergistic effect or to minimize side-effects. Techniques for formulation and administration of the MVA according to the invention may be found in "Remington's Pharmaceutical Sciences", (Muck Publishing Company, Easton, Pa., latest edition).

For the preparation of vaccines, the recombinant MVA according to the invention can be converted into a physiologically acceptable form. This can be done based on the experience in the preparation of poxvirus vaccines used for vaccination against smallpox (as described by Stickl, H. et al. [1974] Dtsch. med. Wschr. 99, 2386-2392).

For example, the purified virus can be stored at −80° C. with a titre of $5 \times 10^8$ TCID$_{50}$/ml formulated in about 10 mM Tris, 140 mM NaCl pH 7.4. For the preparation of vaccine shots, e.g., $10^2$-$10^8$ particles of the virus can be lyophilized in 100 ml of phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other aids such as antioxidants or inert gas, stabilizers or recombinant proteins (e.g. human serum albumin) suitable for in vivo administration. The glass ampoule is then sealed and can be stored between 4° C. and room temperature for several months. However, as long as no need exists, the ampoule is stored preferably at temperatures below −20° C.

For vaccination or therapy, the lyophilisate can be dissolved in an aqueous solution, preferably physiological saline or Tris buffer, and administered either systemically or locally, i.e. parenteral, subcutaneous, intravenous, intramuscular, or any other path of administration know to the skilled practitioner. The mode of administration, the dose and the number of administrations can be optimized by those skilled in the art in a known manner.

It is understood that a preferred vaccine or pharmaceutical composition comprises the recombinant MVA of the invention as described herein. It is also understood that the recombinant MVA of the invention can be used in therapy or vaccination, preferably therapeutic vaccination, preferably against HBV.

The recombinant MVA of the present invention can be advantageously used to manufacture a medicament or vaccine which is useful for treating and/or preventing a pathological condition such as an infectious disease or hepatitis B.

The present invention further envisions a vaccination method against hepatitis B. The vaccination method may be a method of therapeutic vaccination, i.e. for treatment of a disease. In the vaccination method of the invention, a MVA virus expressing an envelope protein from HBV adw as described herein and a MVA virus expressing a core protein from HBV ayw as described herein are administered to a subject. The subject can be any subject as defined herein, preferably a human subject. The subject is preferably in need of the administration. In the vaccination method of the present invention, the envelope protein from HBV adw and the core protein from HBV ayw may be expressed by two different MVA, wherein each of the MVA expresses either the envelope protein or the core protein. In this case, both MVA have to be administered to the subject. The envelope protein from HBV adw and the core protein from HBV ayw may however also be expressed by the same MVA. In this case, only one MVA has to be administered to the subject. It is understood that the latter embodiment is preferred.

Further, the present invention encompasses a MVA virus expressing an envelope protein from HBV adw as described herein which further expresses a CD70 molecule and a MVA virus expressing a core protein from HBV ayw as described herein which further expresses a CD70 molecule that is administered to a subject. The subject can be any subject as defined herein, preferably a human subject. The subject is preferably in need of the administration. Further, the subject preferably is a chronic hepatitis B patient in need of a curative treatment. In the vaccination method of the present invention, the envelope protein from HBV adw and the CD70 molecule and the core protein from HBV ayw and the CD70 molecule may be expressed by two different MVA, wherein each of the MVA expresses either the envelope protein and CD70 or the core protein and CD70. In this case, both MVA should be administered to the subject. The envelope protein from HBV adw and the core protein from HBV ayw and the CD70 molecule may however also be expressed by the same MVA. In this case, only one MVA has to be administered to the subject. It is understood that the latter embodiment is preferred.

It is further understood, that the vaccination method of the invention comprises the administration of a MVA of the invention to a subject and that the MVA is preferably in an effective dose.

The vaccination method of the present invention may comprise at least two vaccination steps. Here, the immune response is induced by prime/boost regimes in which "free" proteins, such as an envelope protein from HBV a/adw and/or a core protein from HBV D/ayw, are used for prime vaccination, wherein one or more recombinant MVA of the invention is/are used for at least one boost vaccinations.

Hence, in a first step (prime), a "protein vaccine" may be administered to the subject. The term "protein vaccine" as used herein refers to a composition comprising envelope protein from HBV A/adw and/or core protein from HBV D/ayw, preferably the envelope protein and the core protein. Both envelope protein and core protein are preferably "free" proteins, meaning that they are preferably not comprised in viral particles. The envelope protein and the core protein may be present in two compositions that are administered alone or in combination with each other. The envelope protein and the core protein may also be comprised in a single composition. The envelope protein or the core protein comprised in the "protein vaccine" may be recombinantly produced by a microorganism, for example by a bacterial or a fungal cell.

It is understood that the "protein vaccine" is preferably essentially free of viral particles, in particular essentially free of MVA. "Essentially free" in this context means that the protein vaccine comprises less than $10^3$ TCID$_{50}$/ml, preferably less than $10^2$ TCID$_{50}$/ml, preferably less than $10^1$ TCID$_{50}$/ml, preferably less than $10^0$ TCID$_{50}$/ml, preferably less than $10^{-1}$ TCID$_{50}$/ml, preferably less than $10^{-2}$ TCID$_{50}$/ml. The protein vaccine may further comprise a suitable adjuvant. As used herein, an "adjuvant" refers to a substance that enhances, augments or potentiates the host's immune response (antibody and/or cell-mediated) to an antigen or fragment thereof. Suitable adjuvants are known to the skilled person. A preferred adjuvant is selected from the group consisting of poly[di(sodium carboxylatoethylphenoxy)]phosphazene (PCEP), an immune stimulatory oligonucleotide, a toll like receptor (TLR) agonist, a saponin or combinations thereof, wherein the TLR agonist is preferably a TLR 3 agonist, a TLR 4 agonist, a TLR 7 agonist, a TLR 8 agonist, or a TLR 9 agonist, and wherein the immune stimulatory oligonucleotide is preferably poly I/C, poly ICLC (a stabilized form of poly I/C) CpG, a Rig-I ligand, a STING ligand, cyclic di-AMP, cyclic di-CMP, cyclic di-GMP, a TLR 7 agonist, a TLR8 agonist, CTA1DD, or dmLT, or combinations thereof. However, the inventors of the present invention have found out that if the protein vaccine comprises a aluminum free adjuvant, such as for example a CpG adjuvant or PCEP, a stronger T cell response will be induced by the vaccination method of the present invention. This finding is surprising since conventional vaccines comprising HBV antigens, such as Engerix-B typically comprises an aluminum containing adjuvant such as aluminum hydroxide. Consequently, the protein vaccine described herein preferably comprises a CpG adjuvant or PCEP or both. The present invention further provides a virus vector, preferably a MVA virus vector, wherein the adjuvant is cyclic di-AMP.

In a further step (boost), one or more recombinant MVA as described herein is/are administered to the subject. The one or more recombinant MVA may be comprised in a pharmaceutical composition or vaccine as described herein.

Typically, the recombinant MVA is administered at least about 1 day after the prime vaccination, preferably at least about 5 days, preferably at least about 1 week, preferably about 1 week to about 8 weeks, preferably about 2 weeks to about 5 weeks, preferably about 3 weeks to about 4 weeks.

It is also encompassed by the invention, that the vaccination regime comprises two or more boost vaccinations after the prime vaccinations. In a preferred embodiment, a protein vaccine is used for prime vaccination and to the first boost vaccination. It is also envisioned by the invention that a second, third or further boost vaccination steps using the protein vaccine may be conducted. Following boost vaccination with protein vaccines, a boost vaccination is conducted by administering one or more recombinant MVA as described herein. It is also encompassed by the invention that the first administration of the recombinant MVA can be followed by a second, third or further administrations (further boost vaccinations).

In such a case, the first boost vaccination with the protein vaccine is conducted at least about 1 day after the previous vaccination step, preferably at least about 5 days, preferably at least about 1 week, preferably about 1 week to about 8 weeks, preferably about 2 weeks to about 5 weeks, preferably about 3 weeks to about 4 weeks. Any subsequent boost vaccination either with the recombinant MVA or with a protein vaccine is then conducted at least about 1 day after the previous vaccination, preferably at least about 5 days, preferably at least about 1 week, preferably about 1 week to about 8 weeks, preferably about 2 weeks to about 5 weeks, preferably about 3 weeks to about 4 weeks.

The vaccination method of the invention may further comprise a treatment of the subject with siRNA and/or shRNA prior to prime-boost vaccination. Such siRNAs or shRNAs are envisioned to target HBV genes and thereby reduces the expression of the targeted HBV genes in a subject infected with HBV. Preferably, the siRNAs and/or shRNAs target the 3' regions of the RNAs encoding the targeted HBV genes. In a preferred embodiment the targeted 3' regions of the RNAs encoding the targeted HBV genes are located upstream to the poly A tails of the RNAs (i.e. the targeted region is 5' to the poly A tail, or in other words in a 5' to 3' direction the targeted region comes first, followed by the poly A tail). If siRNAs are used, it is envisioned that at least one HBV gene is targeted. However, in a preferred embodiment all HBV genes are targeted. One siRNA or shRNA may be used to target a HBV gene. However, also more than one siRNA and/or shRNA may be used to target a HBV gene. It is envisioned that such a treatment with siRNAs and/or shRNAs reduces the expression (i.e. the translation) of the targeted gene/s by at least about 1%, 5%, 10%, 15%, 20%, 25%, 30%, 35%, 40%, 45%, 50%, 55%, 60%, 65%, 70%, 75%, 80% or 85%, preferably at least about 90%. Such a treatment of the subject with siRNA and/or shRNA may be conducted between 1 day and 20 weeks, 1 week and 19 weeks, 2 weeks and 18 weeks, 3 weeks and 17 weeks, 4 weeks and 16 weeks, 5 weeks and 15 weeks, 6 weeks and 14 weeks, 7 weeks and 13 weeks, preferably about 8 weeks prior to start with prime-boost vaccination. The inventors surprisingly found out that such a treatment with siRNA and/or shRNA prior to start with prime-boost vaccination increases the generated T cell response after prime-boost vaccination.

The method for immunization according to the present invention will make use of a therapeutically effective amount of the protein vaccine or the recombinant MVA. A therapeutically effective dose further refers to that amount of the compound/ingredient sufficient to result in amelioration of symptoms, e.g. treatment, healing, prevention or amelioration of such conditions. In a preferred embodiment the immunization may be both prophylactic and/or therapeutic. Effective doses of the present invention for affecting the immune response vary depending upon many different factors, including the type of antigen or vaccine, means of administration, target site, whether the subjects human or an animal, and whether treatment is prophylactic or therapeutic. Preferred doses of the recombinant MVA are disclosed herein.

The invention provides methods for immunizing a subject animal, including birds. Preferably, the animal is a mammal, including rats, rabbits, pigs, mice, and humans comprising administering a dosage of an MVA to a subject. Most preferably, the subject is a human. In one embodiment, the subject is an adult.

Administration can be done by any route of administration as determined by a skilled person. Preferably, administration is parenteral, enteral mucosal, preferably intramuscular, intravenous, subcutaneous (e.g., by scratching or injection), nasal (e.g., by inhalation) or oral. Preferred modes of administration are parenteral or mucosal.

Further, the invention provides an administration which is intramuscular, and wherein administration comprises administration of an adjuvant. Preferably the adjuvant comprises cyclic di-AMP.

Additionally, the present invention also encompasses an administration which is subcutaneous or intramuscular, and wherein the administration comprises administration of an adjuvant. Preferably the adjuvant comprises poly I/C or Rig-1-ligand.

The invention also contemplates vaccination methods as described above, wherein the vaccination vector is not a MVA but one or more *Salmonella* strain(s) that expresses the same antigen(s) as the MVA. Hence, the vaccination method described herein applies mutatis mutandis for vaccination methods using a *Salmonella* strain. Such a vaccination method is preferably a mucosal vaccination method, in which the protein vaccine is preferably adjuvanted with CTA1DD, or dmLT.

The present invention also encompasses any compound disclosed in the methods herein for use in these methods. For example, the present invention encompasses the recombinant MVA for use in a vaccination method as disclosed herein.

The present invention also contemplates a pharmaceutical composition or a vaccine comprising one or more of the recombinant vaccination vectors of the invention. As already mentioned, the "vaccine" can be used to prevent or treat a pathological condition in a subject. The term encompasses both subunit vaccines, i.e. vaccine compositions containing antigens which are separate and discrete from a whole organism with which the antigen is associated in nature, as well as compositions containing the recombinant poxvirus of the present invention carrying, inter alia, the antigen and/or an epitope thereof. The vaccine may or may not include one or more additional components that enhance the immunological activity of the active component. A vaccine may additionally comprise further components typical to pharmaceutical compositions. The vaccine of the present invention is, preferably, for human and/or veterinary use.

The vaccine or the composition of the invention, e.g. a vaccine comprising the MVA virus, may generally include one or more pharmaceutically acceptable carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules, such as proteins, polysaccharides, polylactic acids, polyglycolic acids, polymeric amino acids, amino acid copolymers, lipid aggregates, or the like. Other carriers as described in US 2011/0052627 Col. 7 can also be added to the composition.

The present invention also encompasses a kit comprising at least two vials/containers for prime/boost immunization wherein at least one vial/container comprises a protein vaccine described herein a first inoculation (priming inoculation) and optionally further vials for further inoculations (boost inoculations), wherein the further vial preferably comprise a recombinant vaccination vector of the invention. The kit also comprises at least one further vial/container comprising the recombinant vaccination vector as described herein for at least a further inoculation ("boosting inoculation"). The kit may further comprise instructions for the administration of the recombinant vaccination vector to a subject.

The invention contemplates that the preferred subject is a human. The instructions may indicate that the protein vaccine as defined herein and or the recombinant vaccination vector is administered to the subject in multiple (i.e., 2, 3, 4, 5, 6, etc.) dosages at specific time points (e.g., at least 4 weeks, at least 6 weeks, at least 8 weeks after the previous administration). Preferably, the instructions indicate that the protein vaccine and/or the recombinant vaccination vector is to be administered in at least 3 or at least 4 dosages.

Contemplated by the invention is a kit described herein, wherein the vaccine(s) comprised in the kit is/are suitable for parenteral administration. In such a kit, the protein vaccine may preferably be adjuvanted with PCEP and/or a CpG vaccine, and the recombinant vaccination vector may preferably be a MVA of the invention.

Contemplated by the invention is also a kit described herein, wherein the vaccine(s) comprised in the kit is/are suitable for mucosal administration. In such a kit, the protein vaccine may preferably be adjuvanted with CTA1DD, dmLT, PCEP, c-di-AMP, c-di-CMP, c-diGMP or combinations thereof, and the recombinant vaccination vector may preferably be a *Salmonella* strain, a CMV-, a VSV-based vector, an Adenoviral vector, or a Measles vector, preferably a *Salmonella* strain of the invention.

Additionally, contemplated by the invention is also a kit described herein, wherein the vaccine(s) comprised in the kit is/are suitable for mucosal administration. In such a kit, the protein vaccine may preferably be adjuvanted with CTA1DD, dmLT, PCEP, poly I/C, Rig-1-ligand, c-di-AMP, c-di-CMP, c-diGMP or combinations thereof, and the recombinant vaccination vector may preferably be a *Salmonella* strain of the invention, or preferably a *Salmonella* strain, a CMV-, a VSV-based vector, an Adenoviral vector, or a Measles vector.

The present invention further provides a kit, wherein the protein composition is suitable for intramuscular administration. Preferably, the composition comprises at least one adjuvant that is cyclic-di-AMP.

Contemplated by the present is also a kit, wherein the protein composition is suitable for subcutaneous or intramuscular administration. Preferably, the composition comprises at least one adjuvant that is poly I/C.

The present invention also provides a (host) cell comprising the recombinant MVA described herein. Examples of cells that are permissive to poxviruses include, but are not limited to, COS, HEK-293, BHK, CHO, TM4, CVI, VERO-76, HELA, MDCK, BRL 3A and NIH/3T3 cells. For MVA, the preferred cells are CEF and BHK cells. Additional cell lines are known to those of ordinary skill in the art. Introduction of the poxvirus construct into a cell can be effected by calcium phosphate transfection, electroporation, infection, and other methods known in the art and described in standard laboratory manuals, such as *Current Protocols in Molecular Biology* John Wiley & Sons, Inc. New York.

The present invention also provides (host) cells infected with the recombinant poxvirus. Accordingly, the (host) cell can be infected with an MVA viral vector, and transfected with a further vector, e.g., plasmid vector, comprising the gene to be inserted, preferably under the transcriptional control of an MVA or poxvirus expression control element or promoter, such as the synthetic PrS promoter. As explained above, the plasmid vector comprises sequences capable of directing the insertion of the heterologous sequence into a selected part of the poxvirus genome, such as those flanking one of the naturally occurring deletion sites or intergenic regions.

The term "about" or "approximately" as used herein means within a deviation of 20%, such as within a deviation of 10% or within 5% of a given value or range.

BRIEF DESCRIPTION OF THE FIGURES

FIG. 2: Vaccination-induced HBV-specific antibody- and CD4+ T-cell responses inversely correlate with antigenemia. (A-D) HBVtg mice of low, medium and high antigenemia (n=4) were immunized with CpG adjuvanted HBsAg or HBcAg. On day 21, mice were boosted with MVA-S ($1 \times 10^8$ i. u.) or MVA-core ($1 \times 10^8$ i. u.), respectively. On day 27 (day 6 post boost), sera were analyzed for (A) anti-HBs and (B) anti-HBc antibodies. (C) Splenocytes and (D) liver-associated lymphocytes of low-antigenemic HBVtg mice were stimulated with HBsAg and analyzed for IFNγ-expressing CD4+ T-cells by intracellular cytokine staining. Frequencies of IFNγ-producing T-cells shown are background subtracted. S/CO signal to cutoff; neg.=negative; i. u. infectious units.

FIG. 3: Vaccination-induced HBV-specific CD8+ T-cell frequencies inversely correlate with antigenemia. HBVtg mice of low, medium and high antigenemia (n=4) were immunized with 12 μg CpG adjuvanted HBsAg or HBcAg. On day 21, mice were boosted with MVA-S ($1 \times 10^8$ i. u.) or MVA-core ($1 \times 10^8$ i. u.). On day 27 post boost, splenocytes (A) and liver-associated lymphocytes (B) were stimulated with HBsAg ($S_{109}$ and $S_{208}$)- or HBcAg ($C_{93}$)-specific peptides and analyzed for IFNγ expression by intracellular cytokine staining. Upper and middle panels show exemplary animals, the lowest panel gives frequencies of IFNγ-producing T-cells after background subtraction. i. u. infectious units.

FIG. 10: Grouping of HBVtg mice. Mice were grouped according to their antigen levels which correlates in the case of HBVtg mice closely to the virus titers determined in serum.

FIG. 11: Peptides used for stimulating T-cells. The table gives sequences of peptides used to determine CD8+ T cell responses restricted by the murine $K^b/K^d$ MHS-I alleles. The S pool was used to broadly determine CD4+ and CD8+ T cell responses of mice and humans.

FIG. 12: Graphical overview of the vaccination scheme of Example 4. High-antigenemic HBVtg mice (were vaccinated with 16 µg HBsAg (subtype ayw or adw) and 16 µg HBcAg (subtype ayw) together with the indicated adjuvants on days 0 and 14. On day 28, mice were boosted with MVA-PH5-S (5×10e7 i.u.; subtype ayw or adw) and MVA-core (5×10e7 i.u.). On day 6 post boost, (B) splenocytes (left panel) and liver-associated lymphocytes (LAL, right panel) were isolated and stimulated with peptides S109 and S208 (subtype adw if indicated) or C93 and analyzed for IFNγ expression by intracellular cytokine staining (ICS).

FIG. 13: Correlation of multimer and intracellular cytokine stainings of HBV specific CD8+ T cells. HBVtg mice were immunized with 12 µg HBsAg containing CpG as adjuvant. On day 21, mice were boosted with MVA-S. HBV-specific T cell responses were detected at day 28 by either S190 multimer staining or ICS after ex vivo restimulation with peptide S190.

FIG. 14: Detection of serum immune complexes. HBVtg mice were immunized with CpG adjuvanted HBsAg. On day 21, mice were boosted with MVA-S (1×10⁸ i. u.). On day 6 post boost, sera were analyzed for anti-HBs, HBsAg and HBsAg in precipitated immune complexes. i. u.; infectious units; nd; not detectable FIG. 15A-B shows anti-HBs (FIG. 15A) and anti-HBc (FIG. 15B) antibody responses after 28 (protein prime only) and 34 days (protein prime plus MVA boost). FIG. 15C-D shows CD8+ T cell responses against S and core epitopes after prime (FIG. 15C) and after the MVA-boost (FIG. 15D) FIG. 15E shows a neutralization assay in which HBV subtype ayw was incubated with indicated serum dilutions before infection and HBsAg secretion by infected cells was measured after 4, 7 and 10 days.

FIG. 16A depicts the structure of the multiantigenic polypeptide chain represented by SEQ ID NO: 07. FIG. 16B schematically depicts the formation of subviral particles comprising HBs A/adw and C/ayw antigens. FIG. 16C schematically depicts the formation of empty capsids comprising HBc D/ayw and C/ayw antigens.

FIG. 19: Amino acid sequence of small envelope protein of HBV A2/adw2 including C-terminal overhang (SEQ ID NO: 10). The underlined sequence corresponds to the amino acid sequence of small envelope protein of HBV A2/adw2 without C-terminal overhang (SEQ ID NO: 08). The C-terminal overhang is a P2A cleavage fragment that corresponds to SEQ ID NO: 09.

FIG. 20: Amino acid sequence of core protein fragment 1-149 of HBV D/ayw including N- and C-terminal overhangs (SEQ ID NO: 12). The underlined sequence corresponds to the amino acid sequence of core protein fragment 1-149 of HBV D/ayw without N- and C-terminal overhangs (SEQ ID NO: 11). The C-terminal overhang is a P2A cleavage fragment that corresponds to SEQ ID NO: 09.

FIG. 21: Amino acid sequence of RT domain of HBV polymerase including N- and C-terminal overhangs (SEQ ID NO: 16). The underlined sequence corresponds to the amino acid sequence of RT domain of HBV polymerase without N- and C-terminal overhangs (SEQ ID NO: 06). The C-terminal overhang is a T2A cleavage fragment that corresponds to SEQ ID NO: 13.

FIG. 22: Amino acid sequence of large envelope protein of HBV C/ayw including N- and C-terminal overhangs (SEQ ID NO: 14). The underlined sequence corresponds to the amino acid sequence of large envelope protein of HBV C/ayw without N- and C-terminal overhangs (SEQ ID NO: 04). The C-terminal overhang is a T2A cleavage fragment that corresponds to SEQ ID NO: 13.

FIG. 23: Amino acid sequence of core protein of HBV C/ayw including N-terminal overhang (SEQ ID NO: 15). The underlined sequence corresponds to the amino acid sequence of core protein of HBV C/ayw without N-terminal overhangs (SEQ ID NO: 05).

FIG. 24: Amino acid sequence of consensus sequence of RT-domain of HBV polymerase (SEQ ID NO: 03)

FIG. 25: Amino acid sequence of Consensus sequence of large envelope proteins of genotype C HBV strains (SEQ ID NO: 01).

FIG. 26: Amino acid sequence of consensus sequence of core protein of genotype C HBV strains (SEQ ID NO: 02).

FIG. 29: Estimation of optimal MVA dosage. HBVtg mice of low and medium antigenemia were grouped according to serum HBeAg levels. (A) Groups of HBVtg mice (n=3-4) were immunized twice in two weeks' intervals with 15 µg of particulate HBcAg adjuvanted with c-di-AMP. On day 28, mice were boosted with 4 different dosages of MVA-core (3×10⁶, 1×10⁷, 3×10⁷, 1×10⁸ PFU, respectively). Sera of mice from day 0 and 35 (day 7 post boost) were analysed for HBsAg, HBeAg, anti-HBs and anti-HBc antibodies (B), and ALT levels (C). (D) On day 35 splenocytes and liver-associated lymphocytes of HBVtg mice were isolated, stimulated with MVA-derived peptide B8R or HBcAg-derived peptide c93 and analyzed for IFNγ-expressing CD8+ T-cells by intracellular cytokine staining. Frequencies of IFNγ-producing T-cells shown are background subtracted. i.m.—intramuscular immunization; S/CO—signal to cutoff; PFU—plague forming units; U-units; IU-international units.

FIG. 33: Nucleotide sequence of the construct of the recombinant vaccination vector (rMVA) further expressing CD70 (SEQ ID NO: 27). The different domains of said construct are depicted as follows: Del III-flanking sequence 1, mH5 promoter, HBcore protein, P2A, human CD70 molecule, IRES (EMCV), eGFP, Del III-flanking sequence 2.

EXAMPLES

Mice and Vaccinations

Figure 1:
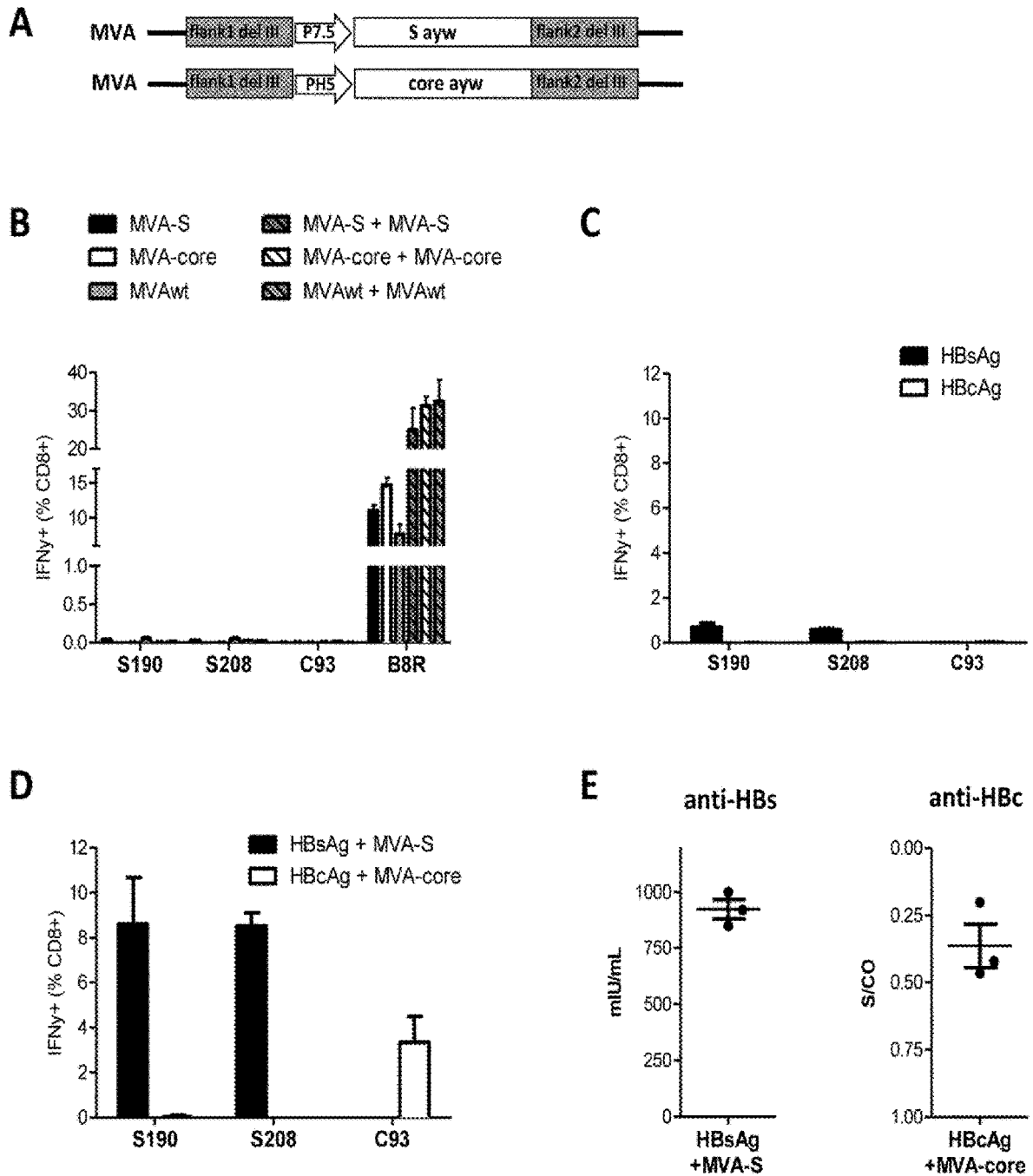
FIG. 1: Protein-prime/MVA-boost vaccination is highly immunogenic. (A) S and core open reading frames of HBV subtype ayw were inserted into deletion III (del III) of the MVA genome under control of poxviral promoters P7.5 and PH5, respectively. (B) Wildtype mice (n=3) were vaccinated once (day 0; filled bars) or twice (day 0 and 21; striped bars) with MVA-S ($1 \times 10^8$ i. u.), MVA-core ($1 \times 10^8$ i. u.) or MVAwt ($1 \times 10^8$ i. u.). On day 8 (post prime) or 27(post boost), splenocytes were stimulated with HBsAg ($S_{190}$ and $S_{208}$)- or HBcAg ($C_{93}$)-derived peptides and analyzed for IFNγ expression by intracellular cytokine staining. (C) C57BL/6 mice were vaccinated with 12 μg recombinant HBsAg or HBcAg. CpG was used as adjuvant. On day 8, splenocytes were stimulated with HBsAg- or HBcAg-derived peptides and analyzed for IFNγ expression by ICS. (D) C57BL/6 mice were prime vaccinated with 12 μg recombinant, CpG adjuvanted HBcAg or HBsAg, and on day 21, boosted with MVA-core ($1 \times 10^8$ i. u.) or MVA-S ($1 \times 10^8$ i. u.). On day 27, splenocytes were stimulated with HBsAg- or HBcAg-derived peptides and analyzed for IFNγ expression by ICS. Sera were analyzed for anti-HBs by immunoassay (middle panel) or anti-HBc by competitive ELISA (right panel). Frequencies of IFNγ-producing T-cells shown are background subtracted. S/CO signal to cutoff; i. u. infectious units.

C57BL/6 wildtype (wt) and HBV-transgenic mice (Strain HBV1.3.32 (Guidotti et al., J Virol 1995; 69:6158-69) (HBV genotype D, subtype ayw), kindly provided by F. Chisari, The Scripps Institute, La Jolla, Calif., USA) were derived from in-house breeding under specific pathogen-free conditions following institutional guidelines. For protein vaccinations, mice were immunized subcutaneously with recombinant yeast HBsAg or E. coli HBcAg (APP Latvijas BiomedicT nas, Riga, Latvia) mixed with 31.91 µg of synthetic phosphorothioated CpG ODN 1668 and/or 25 or 50 µg poly[di(sodiumcarboxylatoethyl-phenoxy)phosphazene] (PCEP) in 50 µl PBS. For MVA vaccination, mice were vaccinated intraperitoneally with $1 \times 10^8$ infectious units of respective recombinant MVA in 500 µl PBS.

Intracellular Cytokine Staining, Multimer Staining and Degranulation Assay

Splenocytes and liver-associated lymphocytes (LAL) were isolated as described previously (Stross et al., Hepatology 2012; 56:873-83) and stimulated with H2-k$^b$- or H-2D$^b$-restricted peptides (FIG. 10) (jpt Peptide Technologies, Berlin, Germany) or recombinant HBsAg (kindly provided by Rheinbiotech-Dynavax, Dusseldorf, Germany) for 5 h in presence of 1 mg/ml Brefeldin A (Sigma-Aldrich, Taufkirchen, Germany). Cells were live/dead-stained with ethidium monoazide bromide (Invitrogen, Karlsruhe, Germany) and blocked with anti-CD16/CD32-Fc-Block (BD Biosciences, Heidelberg, Germany). Surface markers were stained with PB-conjugated anti-CD8a and PE-conjugated anti-CD4 (eBiosciences, Eching, Germany). Intracellular cytokine staining (ICS) was performed with FITC anti-IFNγ (XMG1.2), PE-Cy7 anti-TNFa and APC anti-IL-2 (eBiosciences, Eching, Germany) using the Cytofix/Cytoperm kit (BD Biosciences, Heidelberg, Germany) according to the manufacturer's recommendations.

For degranulation assay, splenocytes were stimulated with peptide in the presence of Monensin, Brefeldin A, FITC-conjugated anti-CD107a antibody and APC-conjugated anti-CD107b antibody for 5 h followed by surface Pacific Blue CD8a staining and ICS with PerCP-Cy5.5 IFNγ (eBiosciences, Eching, Germany) using the Cytofix/Cytoperm kit (BD Biosciences, Heidelberg, Germany) according to the manufacturer's recommendations.

For multimer staining, splenocytes and LAL were stained with PE-conjugated $S_{190}$ (VWLSVIWM, SEQ ID NO: 19) or MVA B8R (TSYKFESV, SEQ ID NO: 20) multimers for 20 minutes followed by staining with Pacific Blue CD8a, FITC KLRG1 and APC CD127 (eBiosciences, Eching, Germany) in the presence of anti-Fc receptor antibody (clone 2.4G2) for 20 minutes. Data were acquired by FACS analysis on aFACSCanto II (BD Biosciences, Heidelberg, Germany) and analyzed using FlowJo software (Treestar, Ashland, USA).

Serological Analysis

Serum levels of HBsAg, HBeAg, anti-HBs and anti-HBc were determined in 1:20 dilutions using AXSYM™ assays (Abbott Laboratories, Abbott Park, Ill., USA). Quantification of serum HBV titers by real-time polymerase chain reaction was performed as described previously (Untergasser et al., Hepatology 2006; 43:539-47).

Neutralization Assay

HepaRG cells differentiated and cultured as described (Lucifora et al., J Hepatol 2011; 55:996-1003) were infected with 200 DNA-containing, enveloped HBV particles/cell (subtype ayw) in duplicate in the presence of a serial dilution of sera from vaccinated mice (1:33, 1:100, 1:333, and 1:1000). As positive control 0.8 international units of the Hepatect™ CP antibody (Biotest Pharma GmbH, Dreieich, Germany) were used. 24 hours post infection, cells were washed three times with PBS and 1 ml of differentiation medium was added. Supernatants were collected on day 4, 7 and 10 post infection and HBsAg was detected by immunoassay in 1:20 dilutions.

Statistical Analysis

Statistical analyses were performed using Prism5 software (GraphPad, San Diego, USA). Results are expressed as mean±standard error of the mean. Differences between groups were analyzed for statistical significance using two-tailed Student's t-tests.

Generation of MVA Vaccines

Recombinant MVA were generated by homologous recombination and host range selection as described previously (Staib et al., Biotechniques 2003; 34:694-6, 698, 700). The entire HBcAg (genotype D, subtype ayw) and HBsAg open reading frames (genotype D, subtype ayw or adw) were cloned into MVA transfer plasmids pIIIΔHR-PH5 or pIIIΔHR-P7.5, thereby placing the HBV proteins under the control of the early/late Vaccinia virus-specific promoters PH5 (HBcAg ayw/HBsAg ayw/HBsAg adw) or P7.5 (HBsAg ayw). After construction of each virus, gene expression, sequence of inserted DNA, and viral purity were verified. For generation of vaccine preparations, MVA were routinely propagated in CEF, purified by ultracentrifugation through sucrose, reconstituted in 1 mM Tris-HCL pH 9.0 and titrated following standard methodology (Staib et al., Methods Mol Biol 2004; 269:77-100).

Immunoblot

NIH-3T3 mouse fibroblasts (CRL-1658) were cultured in RPMI 1640 medium supplemented with 10% FCS, 100 U/ml penicillin and 100 μg/ml streptomycin. Cells were harvested in lysis buffer (50 mM Tris-HCl [pH 8.0], 150 mM NaCl, 1% Nonidet P-40, 0.02% $NaN_3$, and 100 μg/ml phenylmethylsulfonyl fluoride) 16 h post infection, dissolved on 12% sodium dodecyl sulfate-polyacrylamide gel electrophoresis (SDS-PAGE), and blotted onto a nitrocellulose membrane (0.45 μM; Bio-Rad, Munich, Germany). Membranes were incubated at 4° C. with anti-HBc (antiserum H800; kindly provided by H. Schaller), anti-HBs (Murex HBsAg version 3; Abbott, Abbott Park, Ill., USA) or anti-actin (Sigma, Munich, Germany) antibodies at 1:10000, 1:50 and 1:10000 dilutions, respectively. Horseradish peroxidase-labeled secondary mouse and rabbit antibodies (Dianova, Hamburg, Germany) were used at a 1:5000 dilution for 1 h at 21° C. Antibodies were diluted in phosphate-buffered saline containing 5% skim milk. Enhanced chemiluminescence was used as directed (Roche, Mannheim, Germany).

Secreted HBsAg in supernatant of cultured cells was determined using Abbott AxSYM HBsAg assay (Abbott Laboratories, Abbott Park, Ill., USA).

Example 1: Protein-Prime/MVA-Boost Vaccination Induces Strong Anti-HBV Immunity

Figure 7:
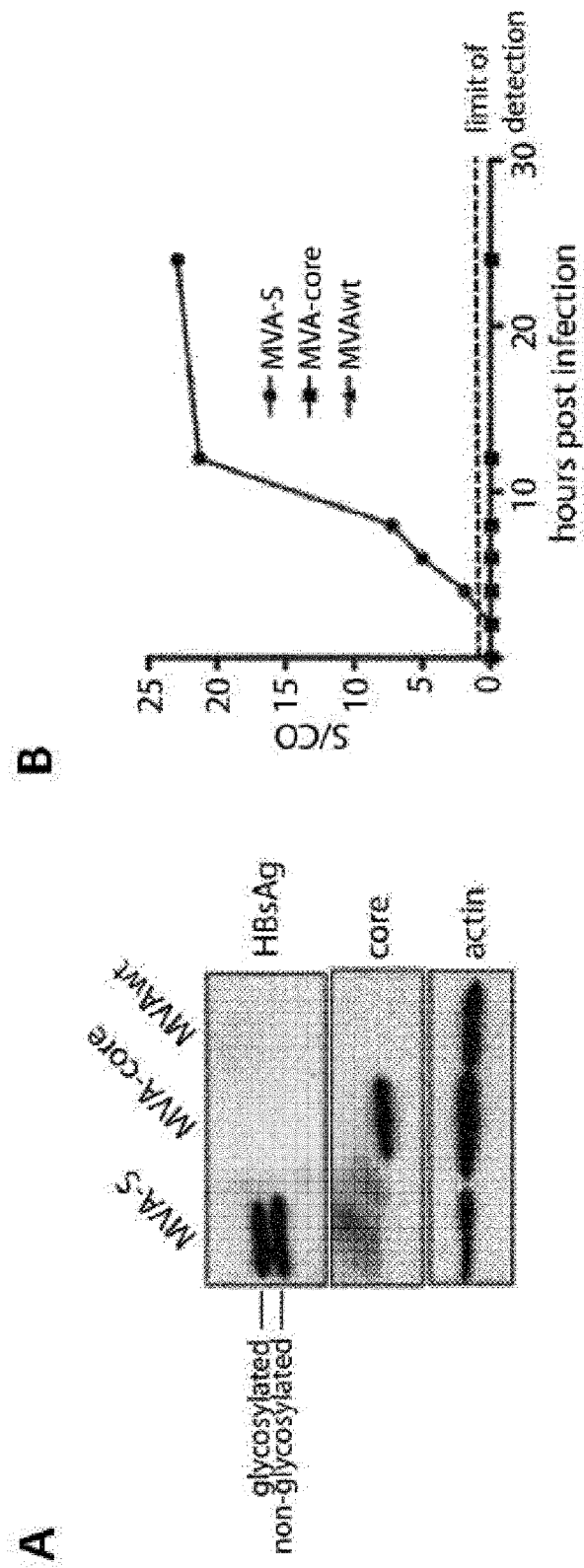
FIG. 7: Expression of HBV antigens by MVA vectors. (A) and (B) Murine NIH-3T3 cells were infected with MVA-S, MVA-core or MVAwt (MOI of 10). 16 h post infection (A) total cellular lysates were analyzed for HBsAg and HBcAg expression by Western blot. (B) secreted HBsAg in the supernatant was determined by HBsAg-specific ELISA. S/CO: signal to cutoff.
Figure 8:
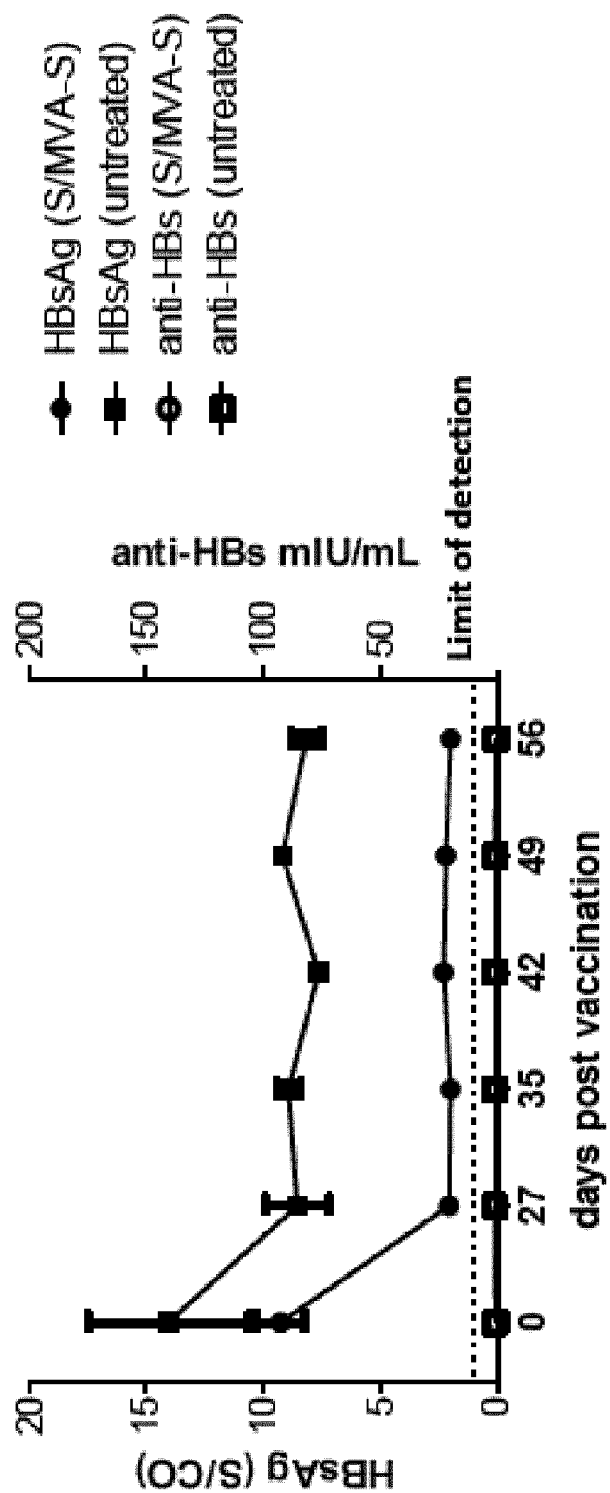
FIG. 8: Vaccination with CpG adjuvanted HBsAg. High-antigenemic HBVtg mice were immunized with 12 μg HBsAg containing CpG as adjuvant. On day 21, mice were boosted with MVA-S. On days 0, 27, 35, 42, 49 and 56 post prime immunization, sera were analyzed for levels of HBsAg and anti-HBs. S/CO: signal to cutoff.

Two MVA vaccines expressing either HBs (MVA-S) or HBc (MVA-core) were generated from HBV genotype D, subtype ayw (FIG. 1A). Western blotting and HBsAg ELISA confirmed correct protein expression from either MVA (FIGS. 7A, B).

To examine immunogenicity, C57BL/6 (wt) mice were immunized with MVA-S, MVA-core or MVAwt ($10^8$ infectious units) i.p. and frequencies of IFNγ-producing CD8+ T-cells were determined by intracellular cytokine staining (ICS) on day 8 post immunization. The i.p. route was used because systemic MVA distribution was intended. MVA-S, MVA-core and MVAwt immunization induced comparable CD8+ T-cell responses to the MVA-derived immunodominant B8R peptide, which was boosted after a second immunization (FIG. 1B). In contrast, no HBV-specific CD8+ T-cell responses were detected (FIG. 1B).

In order to induce HBV-specific immunity, we performed heterologous prime-boost vaccinations. Mice received 12 μg of recombinant, particulate HBsAg or HBcAg (subtype ayw) with CpG as adjuvant. 8 days after HBsAg vaccination, frequencies of splenic CD8+ T-cells secreting IFNγ in response to stimulation with $S_{190}$ and $S_{208}$ peptides were around 0.6% whereas hardly any CD8+ T-cell responses against $C_{93}$ were detectable following HBcAg immunization (FIG. 1C). A boost vaccination on day 21 with either MVA-S or MVA-core was able to induce high frequencies of HBsAg- or HBcAg-specific CD8+ T-cells as well as high anti-HBs or anti-HBc titers, respectively (FIG. 1D). Taken together, those data indicate that heterologous prime-boost vaccination was needed to induce HBV-specific T-cells.

Example 2: High Antigenemia Prevents Induction of Anti-HBV Immunity

In order to investigate the impact of HBV antigen load on the induction of HBV-specific immune responses, HBV1.3.32 transgenic (HBVtg) mice were sorted into low, medium and high-antigenemic groups according to their serum HBeAg levels before vaccination (FIG. 10). 6 days post boost, anti-HBs titers in mice receiving HBsAg/MVA-S were higher in the low-antigenemic group as compared to mice from the medium-antigenemic group, and remained undetectable in high-antigenemic mice (FIG. 2A). Even when it was monitored for 35 days after MVA-S boost, high-antigenemic mice did not develop detectable anti-HBs titers, and HBsAg persisted at low levels (FIG. 11). To study whether anti-HBs may be complexed by the excess amounts of HBsAg and thus escape detection, we dissolved precipitated 131 protein complexes with urea and repeated the immunoassay. Hereby, we found HBsAg-anti-HBs immune complexes in vaccinated high and intermediate but not low antigenemic HBVtg mice (FIG. 14). HBcAg-specific antibodies, however, were detected in sera of HBcAg/MVA-core vaccinated mice from all groups, but titers again showed the tendency to inversely correlate with antigenemia (FIG. 2B). In order to analyze the vaccination-induced CD4+ T-cell response, we stimulated splenocytes and liver-associated lymphocytes (LAL) with HBsAg. Although we found high frequencies of HBsAg-specific CD4+ T-cells in wt mice, we did not detect HBV-specific CD4+ T-cells in HBVtg mice in any of the groups (FIG. 2C, D).

Similar to antibody titers, we observed an inverse correlation between antigenemia and HBV-specific CD8+ T-cell responses. In high-antigenemic mice, HBsAg/MVA-S as well as HBcAg/MVA-core immunization failed to induce detectable HBsAg- or HBcAg-specific CD8+ T− cells— neither in the periphery (spleen) nor in the liver, the site of HBV-replication (FIG. 3A, B). Mice with a medium or low HBeAg burden developed $S_{190}^-$ and $S_{208}$-specific CD8+ T-cell responses to HBsAg/MVA-S, and $C_{93}$-specific T-cell responses to HBcAg/MVA-C vaccination. HBV-specific CD8+ T-cell frequencies detected in low-antigenemic mice were higher as those found in medium-antigenemic mice. Importantly, MVA B8R-specific CD8+ T-cell frequencies were independent of antigenemia and comparable between all groups indicating equal vaccination efficiency (FIG. 3A,B).

During chronic infection and antigen persistence, CD8+ T-cells can develop an exhausted, dysfunctional phenotype. In such conditions, the number of antigen-specific T-cells is largely underestimated through functional tests such as IFNγ production. Therefore it was performed $S_{190}$-, $C_{93}$- and B8R-specific multimer-staining, which did not detect HBV-specific CD8+ T-cells in spleens or livers of immunized high-antigenemic mice while B8R-multimer positive CD8+ T-cells were readily detectable. This suggested that the vaccine indeed failed to induce HBV-specific T-cells in this group. In low- and medium-antigenemic groups, HBV-$S_{190}$—specific and MVA-B8R-specific responses displayed a similar ratio of multimer-positive and IFNγ-positive CD8+ T-cells (FIG. 13). Taken together, HBV antigen levels influence how efficiently HBV-specific antibody as well as T-cell responses can be induced by heterologous prime-boost vaccination.

Example 3: Antigenemia Influences the Quality of Vaccination-Induced Responses

Figure 4:
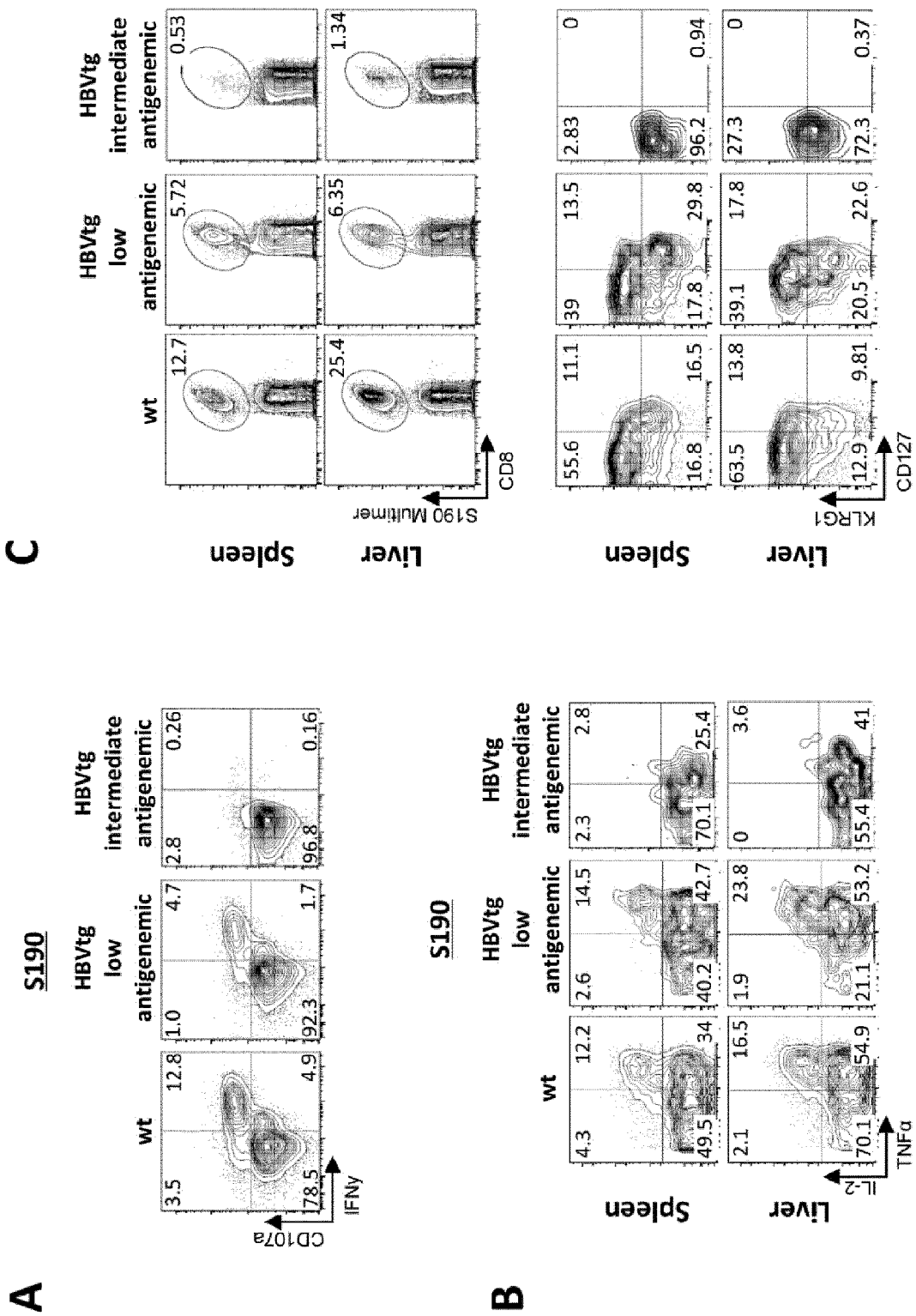
FIG. 4: Functionality of vaccination-induced HBV-specific CD8+ T-cells. Wildtype mice as well as low and medium antigenemic HBVtg mice were immunized with CpG adjuvanted HBsAg. On day 21, mice were boosted with MVA-S ($1 \times 10^8$ i. u.). On day 6 post boost, S-specific spleen-derived CD8+ T-cells were analyzed (A) for CD107a and IFNγ expression. (B) S-specific spleen or liver derived CD8+ T-cells were analyzed for IFNγ-, IL-2- and TNFa-expression after stimulation with peptide $S_{190}$. (C) Multimer-staining of $S_{190}$-specific CD8+ T cells and co-staining for CD127 and KLRG-1 surface expression. i. u. infectious units.

Important effector functions of CD8+ T-cells include the production of IL-2 and TNFα in addition to IFNγ as well as the ability to degranulate in response to peptide stimulation, which can be analyzed by the surface expression of CD107a. Upon S190 peptide stimulation, IFNγ+S190-specific splenic CD8+ T-cells induced in wt mice and low-antigenemic HBVtg mice by HBsAg/MVA-S immunization degranulated to similar ratios (72.3% and 73.4%, respectively) (FIG. 4A). and showed comparable expression of IL-2 and TNFa in spleen and liver CD8+ T-cells derived from medium-antigenemic mice, which were also able to degranulate upon peptide stimulation although to a lesser extent (62%), but lacked IL-2 expression (FIG. 4B).

To determine the differentiation status of multimer-binding cells to proliferate, we stained CD127 and KLRG-1. Vaccination of wt and low-antigenemic HBVtg mice induced a high percentage of $S_{190}$-specific CD127+ KLRG-1-multimer-binding cells in the livers and spleens, that are considered to be a transient precursors of long-lived cells with the potential to proliferate and to give rise to new effector cell progeny (FIG. 4C). In medium-antigenemic mice, these cells, however, were hardly detectable (FIG. 4C). These data indicate that HBV antigen expression diminishes polyfunctionality of CD8+ T-cells and in particular effector cell IL-2 secretion and proliferation capacity.

Example 4: Comparison of Adjuvants for Protein-Prime Vaccination

In order to investigate the polyphosphazene adjuvant PCEP will enhance the immune stimulatory effect of CpG, PCEP was used instead of CpG or was added to CpG for the protein vaccine formulation and combined HBsAg and HBcAg.

Figure 9:
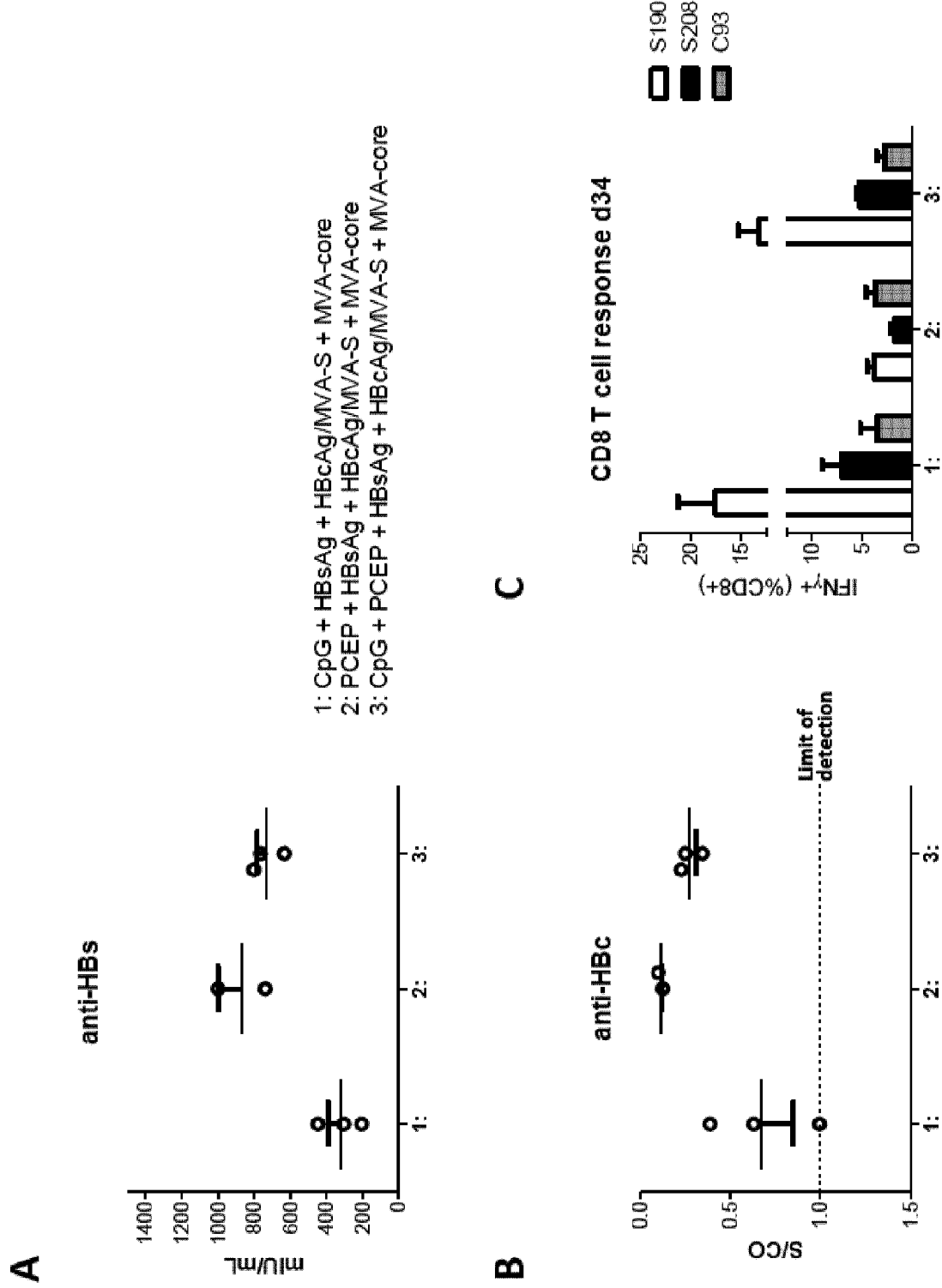
FIG. 9: Comparison of adjuvants for protein-prime vaccination. (A) to (C) Wildtype mice were vaccinated with 16 μg HBsAg (subtype ayw) and 16 μg HBcAg (subtype ayw) together with the indicated adjuvant(s) on days 0. On day 28, mice were boosted with MVA-PH5-S ($5 \times 10^7$ i.u.; subtype ayw) and MVA-core ($5 \times 10^7$ i.u.). On day 6 post boost sera were analyzed for presence of (A) anti-HBs and (B) anti-HBc. (C) On day 6 post boost splenocytes were analyzed by ICS after stimulation with HBsAg ($S_{190}$ and $S_{208adw}$)- or HBcAg ($C_{93}$)-specific peptides. Bars show percentage (mean±SEM) of CD8+ cells staining positive for IFNγ after background subtraction. i. u. infectious units.

Wildtype mice were vaccinated with 16 µg HBsAg (subtype ayw) and 16 µg HBcAg (subtype ayw) together with the respective adjuvant(s) on days 0. On day 28, mice were boosted with MVA-PH5-S ($5 \times 10^7$ i.u.; subtype ayw) and MVA-core ($5 \times 10^7$ i.u.). On day 6 post boost sera were analyzed for presence of anti-HBs (FIG. 9A) and anti-HBc (FIG. 9B). On day 6 post boost splenocytes were analyzed by ICS after stimulation with HBsAg ($S_{190}$ and $S_{208adw}$)- or HBcAg ($C_{93}$)-specific peptides (FIG. 9C). Bars show percentage (mean±SEM) of CD8+ cells staining positive for IFNγ after background subtraction. i. u. infectious units.

The use of PCEP (alone or in combination with CpG) was superior in inducing anti-HBs and anti-HBc antibody responses to CpG alone after protein-prime/MVA-boost vaccination in wt mice, while CD8+ T-cell responses were comparable (FIG. 9A-C).

Example 5: Comparison of Adjuvant Combinations

Next it was aimed at determining the effect of different adjuvants on humoral and cellular immune responses. Therefore, wild type CH57Bl/6 mice were primed with particulate HBcAg and HBsAg complexed in different adjuvant formulations. In groups 1 to 3 (n=3) HBsAg was complexed with alumn hydroxide and combined with HBcAg, CpG or polyphosphazene adjuvant or both. Groups 4 to 6 (n=3) were vaccinated using particulate HBcAg and HBsAg adjuvanted with either CpG or polyphosphazene or both but without any alumn. At day 28, all animals were booster with MVA expressing core and S subtype adw.

Figure 15:
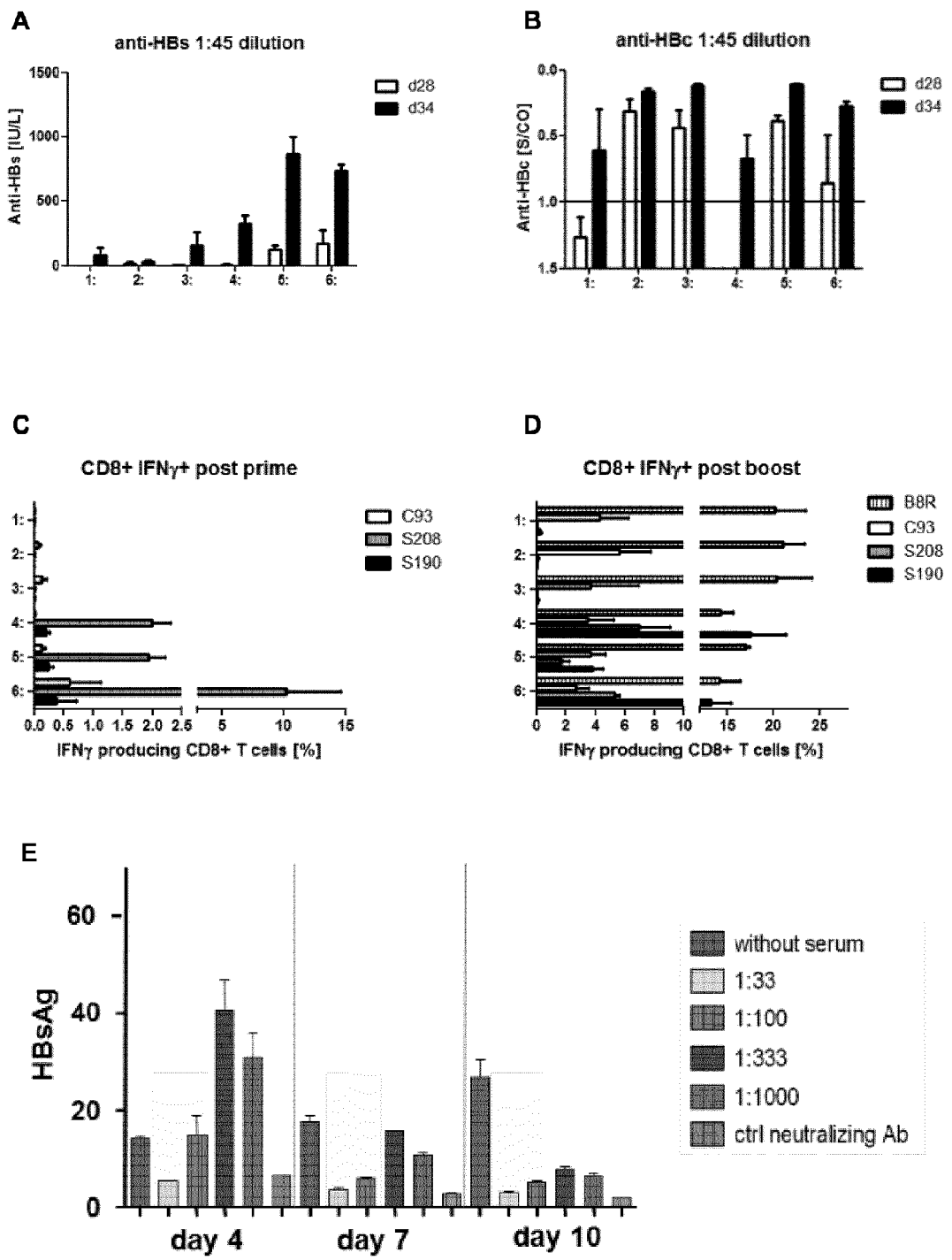
FIG. 15: Comparison of different vaccine adjuvants. Wild type CH57131/6 mice were immunized with HBcAg and HBsAg complexed in different adjuvant formulations. 1:CpG plus alumn hydroxide; 2: polyphosphazene PCEP plus alum; 3: PCEP plus CpG plus alumn; 4: CpG only; 5: PCEP only; 6: CpG plus PCEP. At day 28, all animals were boosted with MVA expressing core and S subtype adw.
Figure 16:
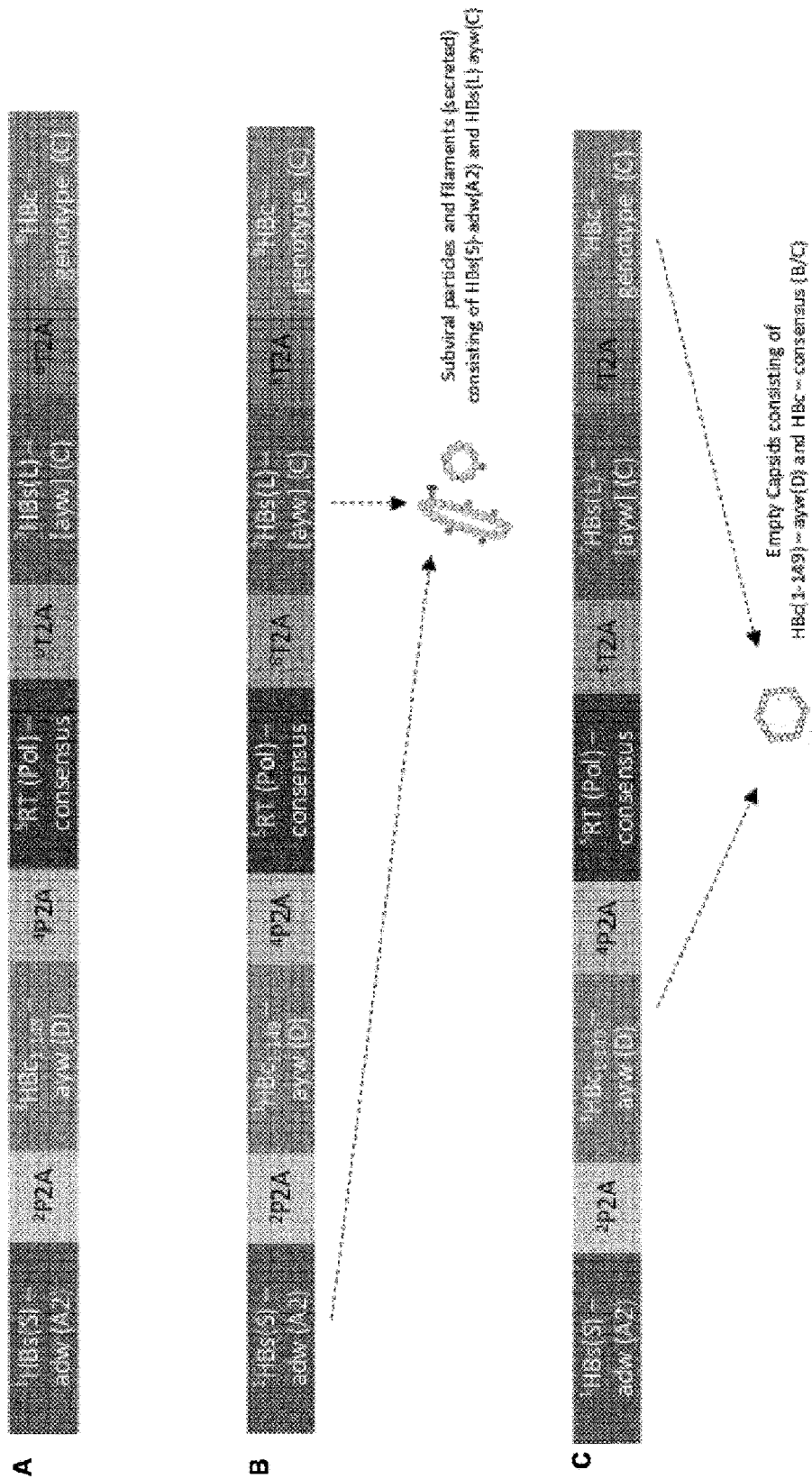
FIG. 16: Multiantigenic open reading frame.
Figure 17:
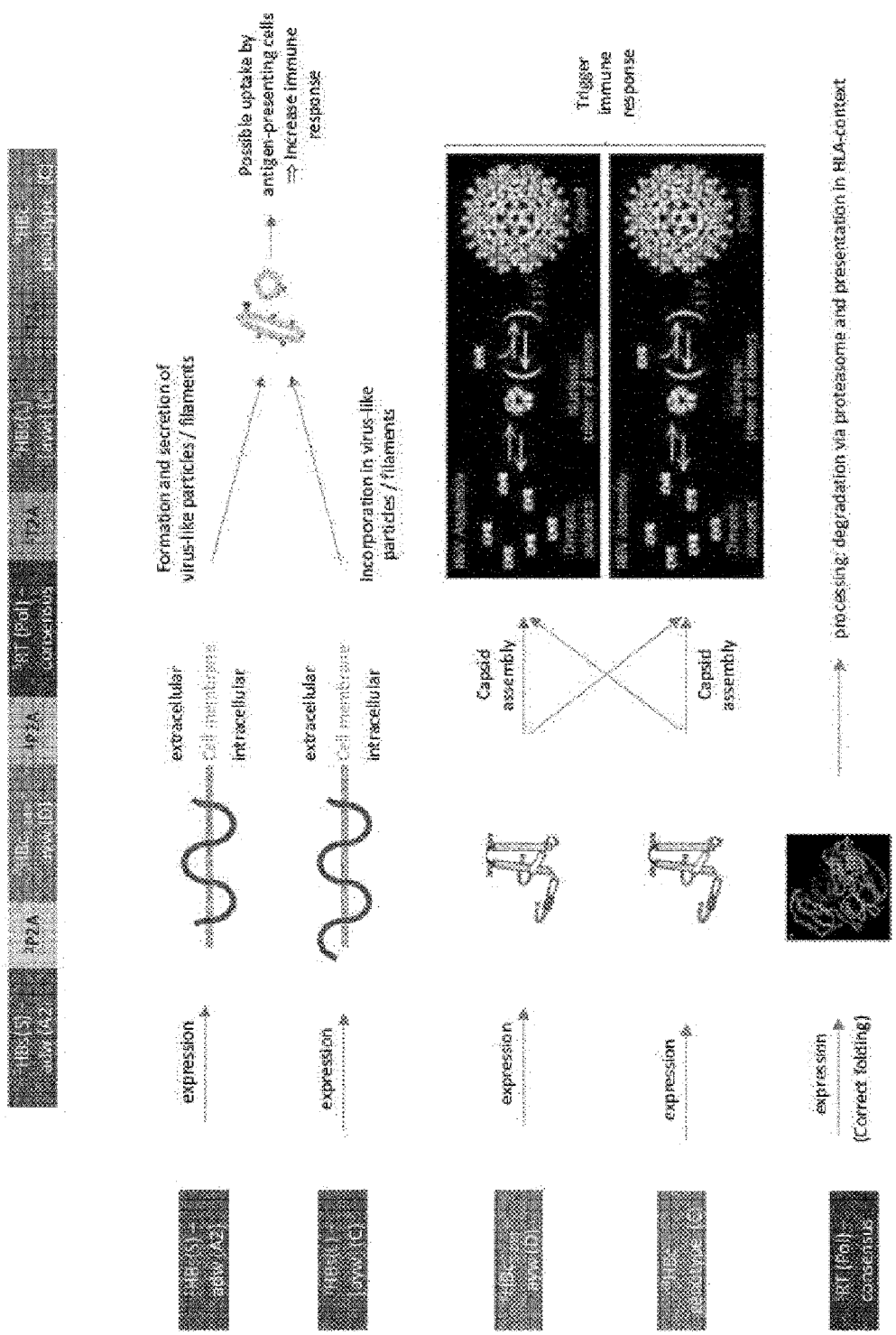
FIG. 17: Schematic illustration of completely processed proteins derived from the multiantigenic polypeptide chain represented by SEQ ID NO: 07 and their fate.
Figure 18:
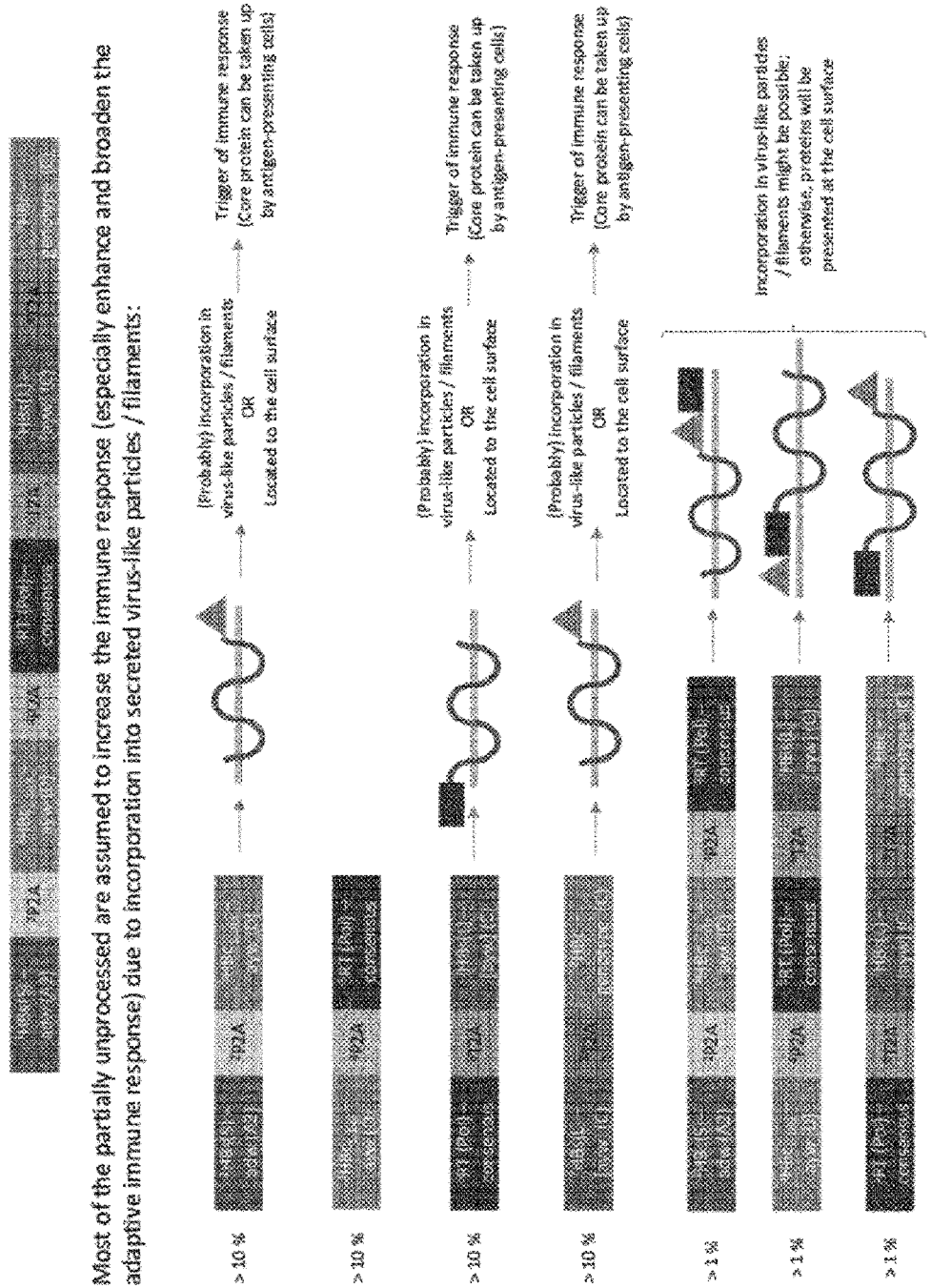
FIG. 18: Schematic illustration of partially unprocessed proteins derived from the multiantigenic polypeptide chain represented by SEQ ID NO: 07 and their expected fate. Most of the partially unprocessed are assumed to increase the immune response (especially enhance and broaden the adaptive immune response) due to incorporation into secreted virus-like particles/filaments.

Antibody responses against HBs and HBc were determined after 28 days (protein prime only) and after 34 days (protein prime plus MVA boost). FIGS. 15A and 15B show that antibody responses in particular against HBs were unexpectedly much more pronounced when alum was avoided. FIG. 15C-D shows CD8+ T cell responses against S and core epitopes after prime (FIG. 15C) and after the MVA-boost (FIG. 15D).

T cell responses were detectable already after prime when vaccine formulations contained no alumn. Interestingly, after the MVA boost with equal efficiency in all groups (indicated by B8R-specific responses), all mice developed core-specific T cell responses, while again animals vaccinated without alumn developed much more pronounced S-specific CD8+ T cell responses.

Example 6: Vaccination with Heterologous HBsAg Subtype Breaks T-Cell Tolerance and Induces Strong Antibody Production in High-Antigenemic HBVtg Mice Mouse sera were analyzed for their neutralization capacity after vaccination. Mice vaccinated with HBsAg subtype adw, were able to cross-neutralize HBV subtype ayw even in high dilutions of up to 1:1000 (FIG. 15E).

Next, it was aimed at enhancing the immunogenicity of heterologous protein-prime/MVA-boost vaccination to break tolerance in the presence of higher HBV antigen load.

Figure 5:
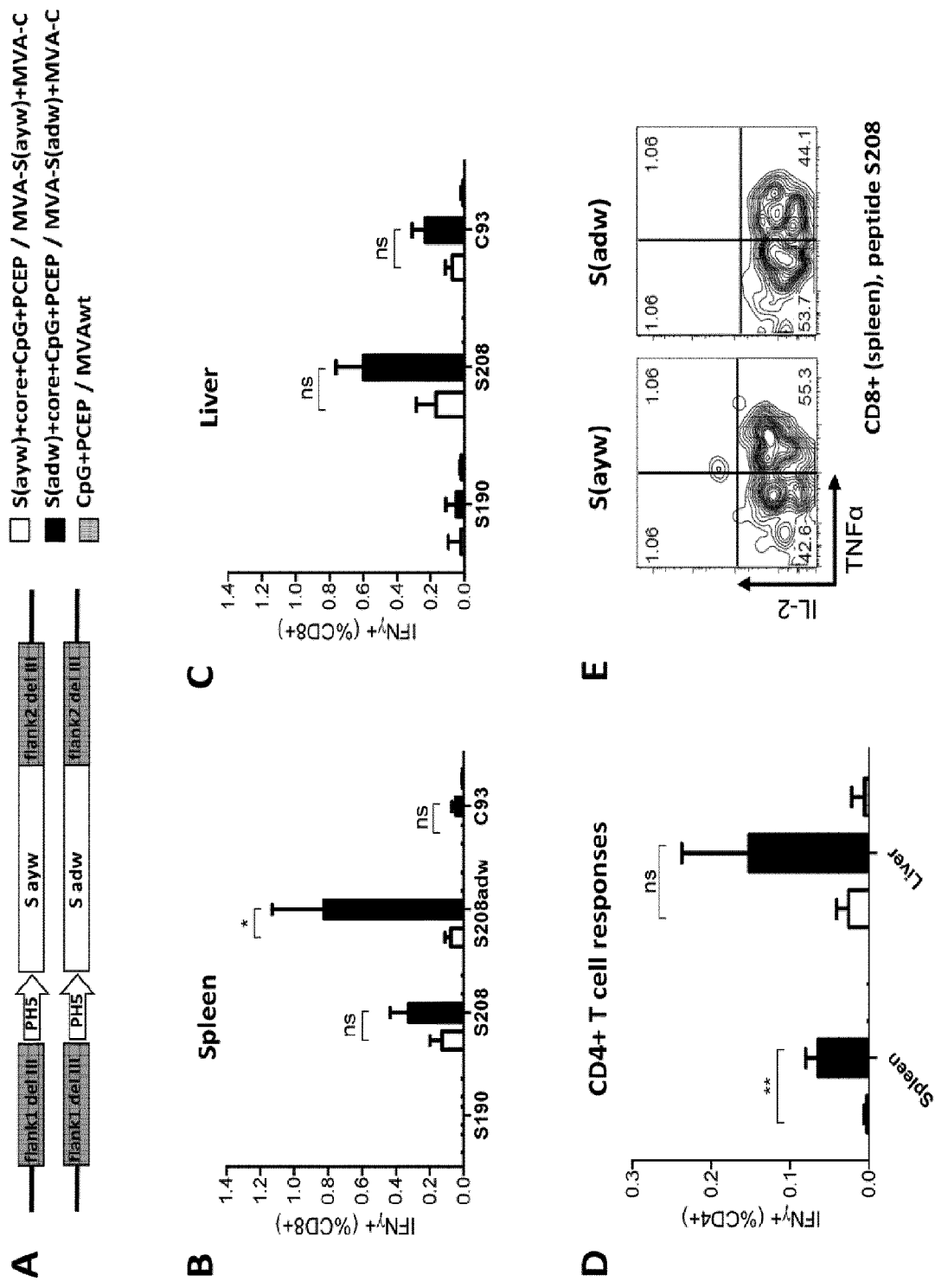
FIG. 5: Heterologous vaccination breaks T-cell tolerance in high-antigenemic HBVtg mice. (A) S subtype ayw and adw open reading frames were placed into deletion III (del III) of the MVA genome under control of the strong poxvirus promoter PH5. (B) to (D) High-antigenemic HBVtg mice (n>4) were vaccinated with 16 μg HBsAg (subtype ayw or adw) and 16 μg HBcAg (subtype ayw) together with the indicated adjuvants on days 0 and 14. On day 28, mice were boosted with MVA-PH5-S ($5 \times 10^7$ i. u.; subtype ayw or adw) and MVA-core ($5 \times 10^7$ i. u.). On day 6 post boost (B) splenocytes (left panel) and liver-associated lymphocytes (LAL, right panel) were isolated and stimulated with peptides $S_{109}$ and $S_{208}$ (subtype adw if indicated) or $C_{93}$ and analyzed for IFNγ expression by intracellular cytokine staining. (C) Splenocytes and LAL were stimulated with a C-terminal pool of HBsAg-specific 15-mer peptides (covering amino acids 145 to 226, subtype ayw) and analyzed for IFNγ-expressing CD4+ T-cells by ICS. (D) Representative FACS plot of $S_{208}$-specific CD8+ T-cells expressing IFNγ were analyzed for TNFa and IL-2 expression. Mean±SEM of IFNγ-producing T cell frequencies are shown background subtraction. ns: not significant. * p<0.05,  p<0.01 students t-test; i. u. infectious units

To test whether a stronger antigen trigger would improve vaccination efficiency, new MVAs expressing HBsAg were engineered also under control of the stronger promoter PH5 (FIG. 5A) and a second protein vaccination on day 14 was performed (FIG. 12). In addition, HBsAg of subtype ayw (identical to HBVtg mice) and adw were compared. In addition, PCEP was added to CpG for the protein vaccine formulation and combined HBsAg and HBcAg during prime and boost in order to achieve immune responses to multiple HBV antigens. When this modified vaccination regimen (combined HBsAg/HBcAg prime adjuvanted with CpG and PCEP on days 0 and 14 followed by boost on day 28 using MVA-S/MVA-core which express the antigens under the stronger PH5 promoter) was applied, there was the ability to break tolerance in high-antigenemic HBVtg mice and induced HBsAg- and HBcAg-specific CD8+ and CD4+ T-cells (FIGS. 5B, C).

Next, it was investigated whether a partial mismatch between vaccine and target antigen would improve vaccine efficacy (Schirmbeck et al., Eur J Immunol 2003; 33:3342-52). Either vaccine antigen, $S_{ayw}$ or $S_{adw}$, induced CD8+ T-cells against both subtypes (FIG. 5B) as determined with subtype-specific peptide $S_{208}$ (FIG. 11). However, the heterologous $S_{adw}$-containing vaccine induced stronger CD8+ and detectable CD4+ T-cell responses (FIGS. 5B, C). Similar to what we had observed with S-specific CD8+ T-cells derived from medium-antigenemic mice (FIG. 4B), splenic $S_{208}$-specific CD8+ T-cells were found to secrete IFNγ and to certain extend TNFa, but showed only marginal expression of IL-2 (FIG. 5D).

Figure 6:
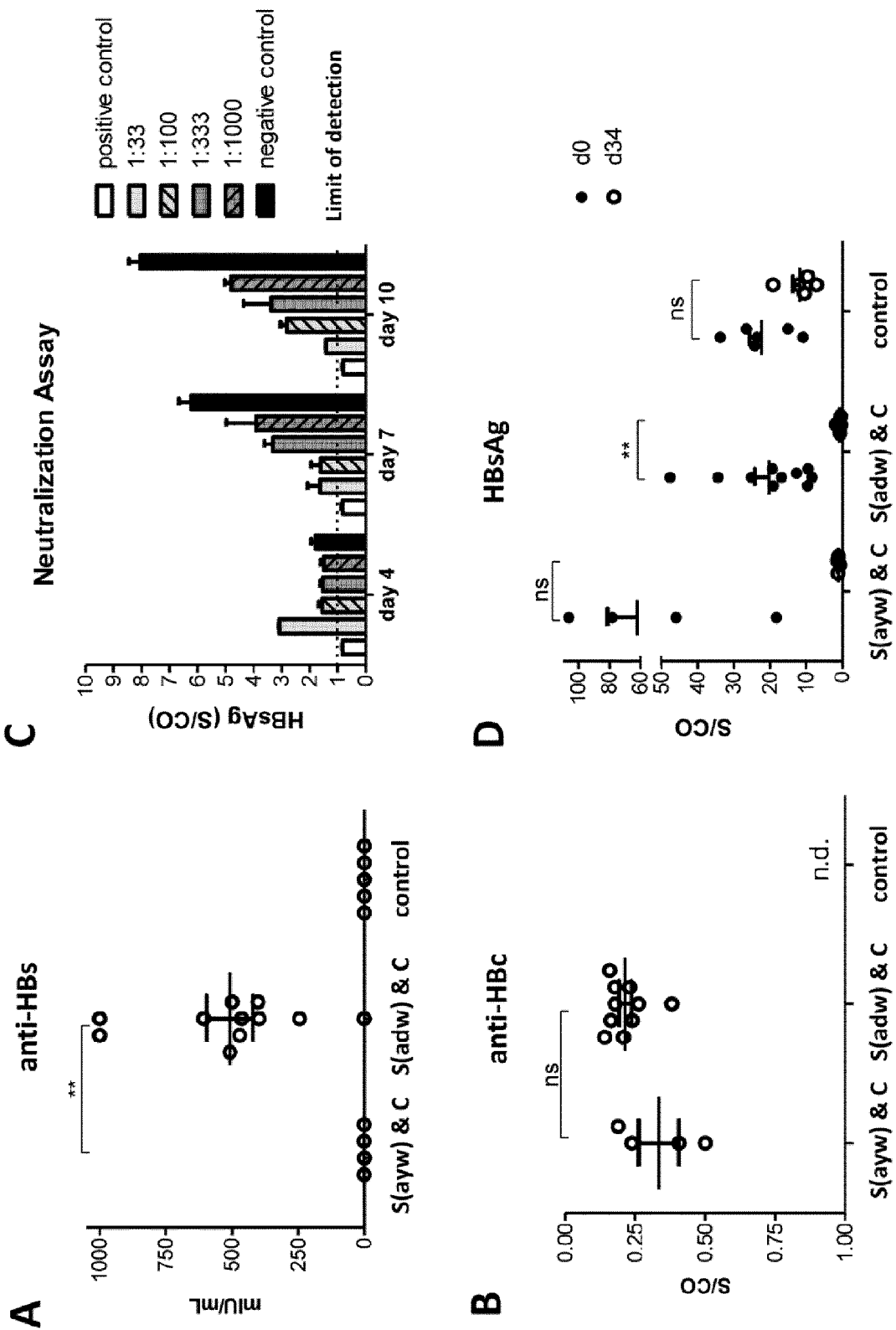
FIG. 6: Heterologous vaccination induces seroconversion in high-antigenemic HBVtg mice. (A) to (D) High-antigenemic HBVtg mice (n>4) were vaccinated with 16 μg HBcAg (subtype ayw) and 16 μg HBsAg (subtype ayw or adw as indicated) adjuvanted with CpG and PCEP on days 0 and 14. On day 28, mice were boosted with MVA-PH5-S ($5 \times 10^7$ i.u.; subtype ayw or adw) and MVA-core ($5 \times 10^7$ i.u.). As control, 5 high-antigenemic HBVtg mice were vaccinated with adjuvants CpG and PCEP on days 0 and 14 followed by a boost with $1 \times 10^8$ MVA-wt. On day 6 post boost, sera were analyzed for presence of (A) anti-HBs or (B) anti-HBc antibodies. (C) Anti-HBs positive sera from HBVtg mice were analyzed for neutralization capacity of subtype ayw HBsAg. (D) shows serum HBsAg levels before and after vaccination. Mean±SEM is shown. ns: not significant S/CO signal to cutoff.  p<0.01 students t-test.

Notably, only the $S_{adw}$, but not the $S_{ayw}$ containing vaccine formulation was able to induce detectable anti-HBs antibody responses in high-antigenemic mice (FIG. 6A), while anti-HBc antibodies were induced by both formulations (FIG. 6B). Importantly, anti-HBs antibodies generated by $S_{adw}$ were able to neutralize HBV particles of subtype ayw (FIG. 6C). Concomitantly to the induction of neutralizing anti-HBs in the $S_{adw}$ vaccination group, levels of HBsAg significantly dropped to low levels (FIG. 6D). Taken together, this indicated that the modified vaccination scheme indeed allowed breaking B- and T-cell tolerance in HBVtg mice.

Example 7: Broad Immune Response Induced by Multi-Antigenic MVA

Next, it was aimed at comparing the induction of immune responses against one, two and several HBV antigens using a multi-antigenic MVA. Unexpectedly, humoral as well as cellular immune responses against either S or S and Pol were improved when core was co-expressed by the MVA vaccine vector.

Example 8: Combination of RNAi and Therapeutic Vaccination

Figure 27:
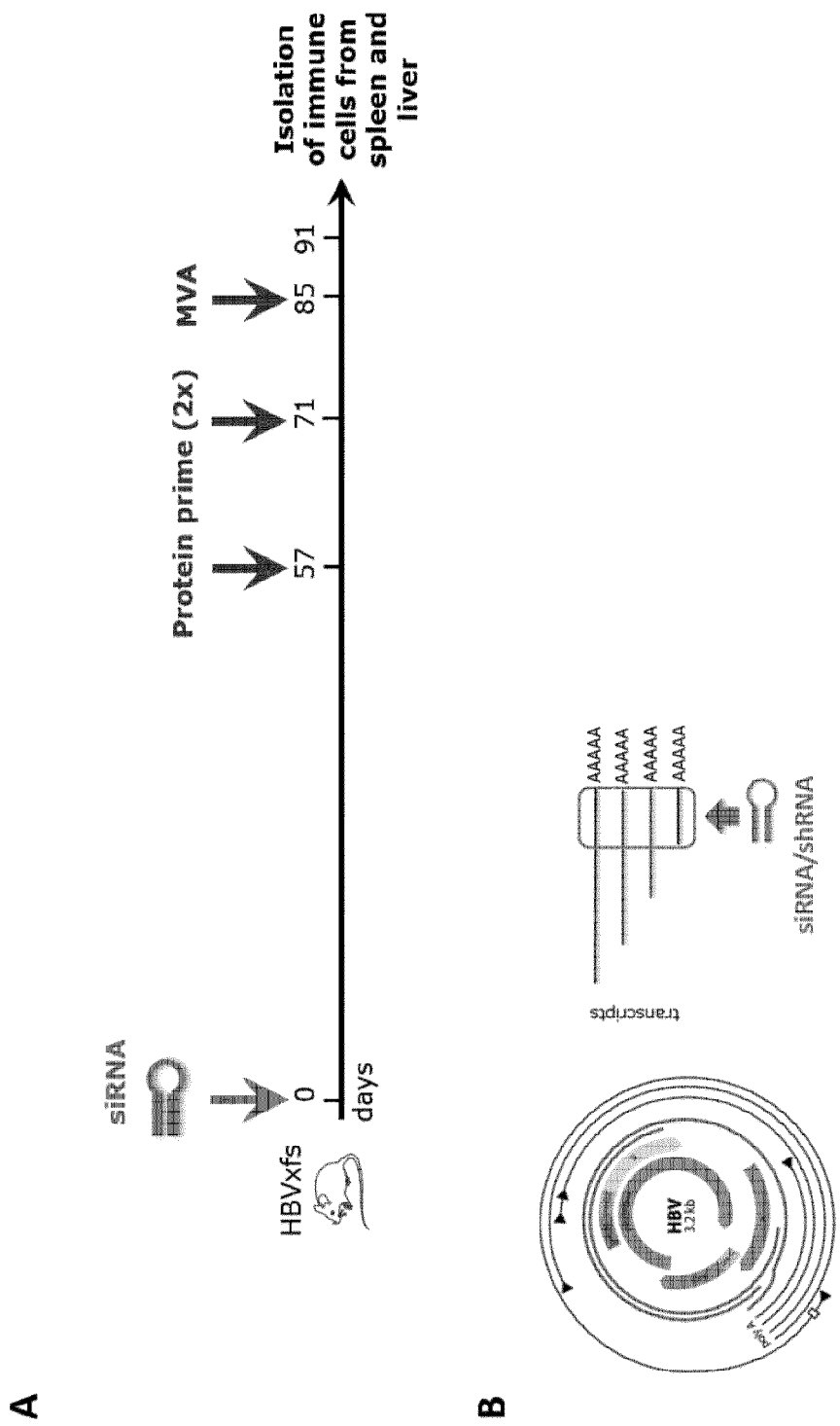
FIG. 27: Combination of RNAi and therapeutic vaccination. (A) Experimental set-up. HBVxfs transgenic mice received HBV-specific siRNA (siHBV), an irrelevant siRNA (siNEG) or were left untreated. Eight weeks later, all mice received protein prime—MVA boost therapeutic immunization with HBV core and surface antigens (HBcAg and HBsAg). (B) Schematic illustration of the HBV-specific siRNA/shRNA design.

HBV transgenic mice, strain HBVxfs, expressing high titer HBV antigens were treated with HBV-specific siRNAs targeting the 3' region of all HBV RNAs. siRNA treatment reduced HBeAg and HBsAg levels by 90%. After 8 weeks, animals were vaccinated with a protein prime—MVA-HBV boost vaccine to induce anti-HBs antibodies and HBV-specific T cells (FIG. 27). As a protein vaccine, particulate HBsAg and HBcAg were adjuvanted with CpG and PCEP. The MVA vaccine vector expressed the complete open reading frame of HBV S and core proteins. Controls were no siRNA, no vaccination and a combination thereof.

Figure 28:
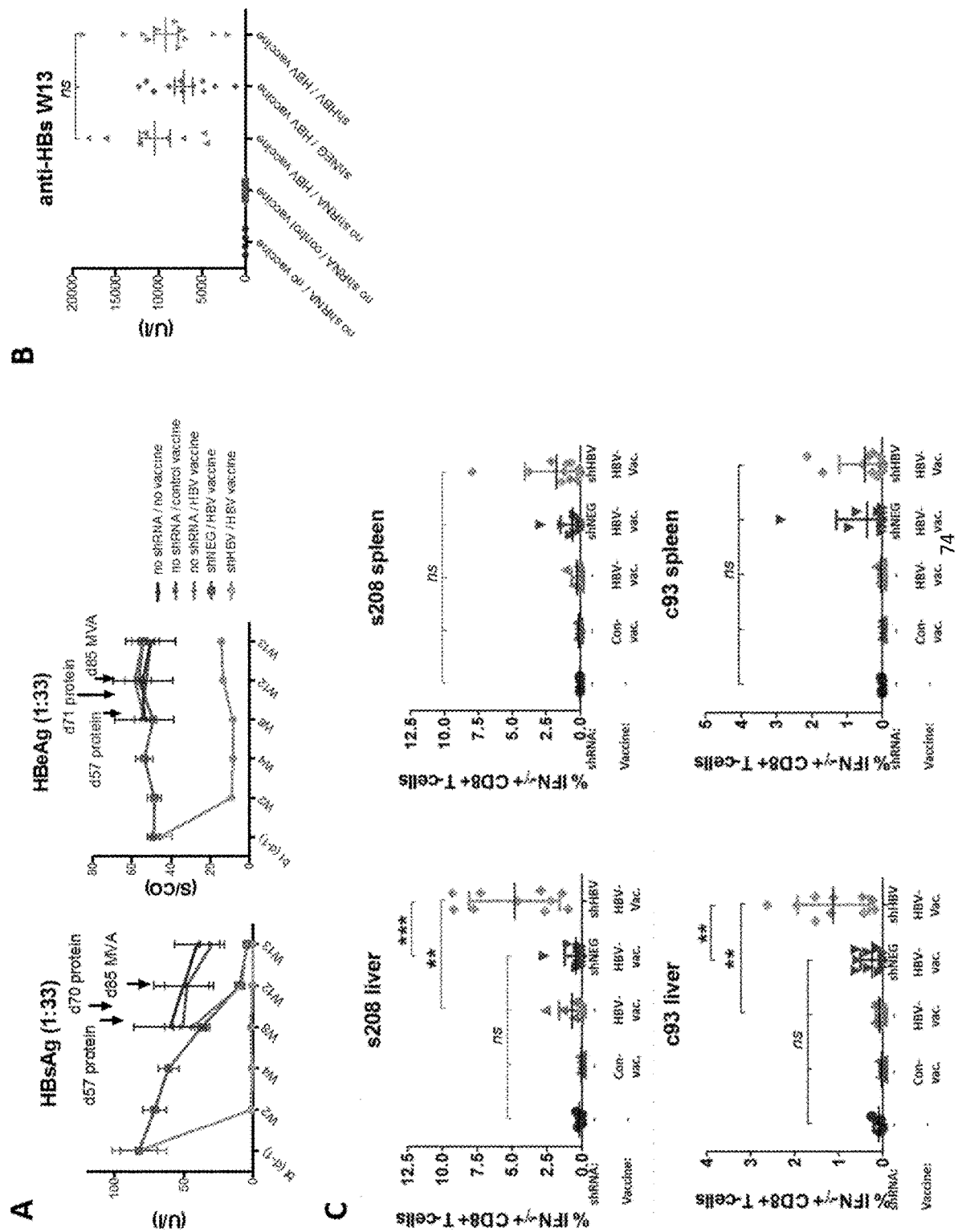
FIG. 28: HBV antigen levels and antibody response and CD8+ T cell responses. (A) Kinetics of serum HBeAg and HBeAg levels. (B) Anti-HBs antibodies in the serum of mice at the time point of sacrifice (day 91, week (W)13). (C) CD8+ T cell responses measured in liver and spleen after prime-boost vaccination.

6 days after boost vaccination, mice were sacrificed and HBeAg and HBsAg levels as well as anti-HBs titers were determined (FIG. 28A, B). From livers and spleen, T cells were isolated, ex vivo stimulated with HBV-specific peptides, stained for interferon gamma expression by intracellular cytokine staining and analyzed by flow cytometry (FIG. 28C).

Example 9: Estimation of Optimal MVA Dosage

In the first sets of experiments we aimed to assess the lowest MVA dosage for heterologous protein-prime/MVA-boost vaccination that would show satisfactory immunogenicity and would be able to break immune tolerance in HBVtg mice. Therefore, groups of low and middle antigenemic HBVtg mice were immunized twice in two weeks' intervals with 15 µg of particulate HBcAg adjuvanted with bis-(3',5')-cyclic dimeric adenosine monophosphate (c-di-AMP). On day 28, mice were boosted with 4 different dosages of MVA-core ($3\times10^6$, $1\times10^7$, $3\times10^7$, $1\times10^8$ PFU, respectively) (FIG. 29A). Humoral and cellular immune responses elicited by immunization regimens employing various MVA dosages were evaluated 7 days after the boost immunization (day 35).

Sera of mice from day 0 and 35 (day 7 post boost) were analyzed for HBsAg, HBeAg, anti-HBs and anti-HBc antibodies (FIG. 29B). All immunization regimens elicited similar levels of anti-HBc antibodies detected in the serum of HBVtg mice at day 35. In addition, all groups of mice showed significant reduction of HBsAg in the blood. This effect was not mediated by anti-HBs antibodies as the immunization regimen did not include HBsAg, crucial for HBsAg serocoversion in HBVtg model. Interestingly, HBVtg mice from the groups that received higher dosages of MVA-core ($3\times10^7$ and $1\times10^8$ PFU) as a boost showed considerable decrease in serum HBeAg levels (FIG. 29B). Moreover, slight elevation of liver alanine transferase (ALT) was observed also in the groups of mice that received higher dosages of MVA-core ($3\times10^7$ and $1\times10^8$ PFU) (FIG. 29C). These data suggest that immunization protocols in these two groups of mice resulted in suppressed HBV replication in the liver possibly due to the enhanced activity of HBcAg-specific T cells. Indeed, intracellular IFNγ staining of liver-associated lymphocytes (LALs) and splenocytes showed, that HBVtg mice that were immunized with higher dosages of MVA-core could mount more effective HBV-specific CD8+ T cell responses, particularly in the liver (FIG. 29D). Simultaneously, MVA-specific CD8+ T cell responses were not significantly increased with the higher MVA dosage used for immunization.

It can be concluded from these results that MVA-core dosage of $3\times10^7$ PFU for heterologous protein-prime/MVA-boost vaccination is sufficient to break immune tolerance in low and middle antigenemic HBVtg mice.

Example 10: Evaluation of c-Di-AMP as an Adjuvant for Protein Priming

Figure 30:
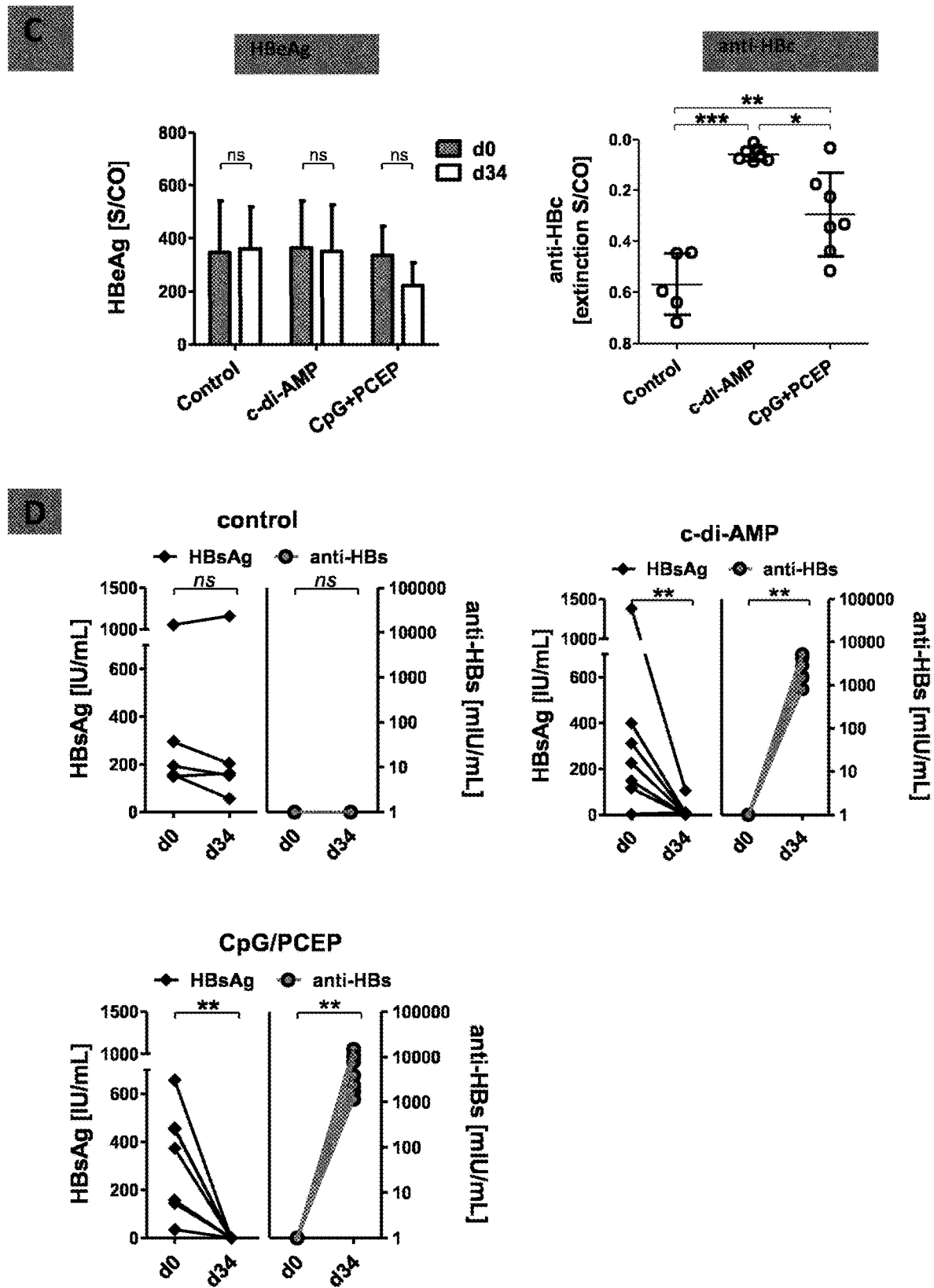
FIG. 30: Evaluation of c-di-AMP as an adjuvant for protein priming. HBVtg mice of medium and high antigenemia were grouped according to serum HBeAg levels. (A) Groups of HBVtg mice (n=7) were immunized in two weeks' intervals with mixture of 15 µg of particulate HBsAg and 15 µg of HBcAg adjuvanted with c-di-AMP, or combination of CpG/PCEP. On day 28, mice were boosted with $10^8$ MVA-S/core. HBVtg mice (n=4) injected twice with c-di-AMP and boosted with 'empty' MVA (MVAwt) were used as controls. Sera of mice from day 0 and 34 (day 6 post boost) were analysed for ALT levels (B), HBsAg, HBeAg, anti-HBs and anti-HBc antibodies (C-D). (E) On day 34 splenocytes and liver-associated lymphocytes of HBVtg mice (n=4) were isolated, stimulated with HBcAg-derived peptide c93 or HBsAg-derived peptide s208 and analyzed for IFNγ-expressing CD8+ T-cells by intracellular cytokine staining. Frequencies of IFNγ-producing T-cells shown are background subtracted. i.m.—intramuscular immunization; S/CO—signal to cutoff; PFU—plague forming units; IU-international units.
Figure 30:
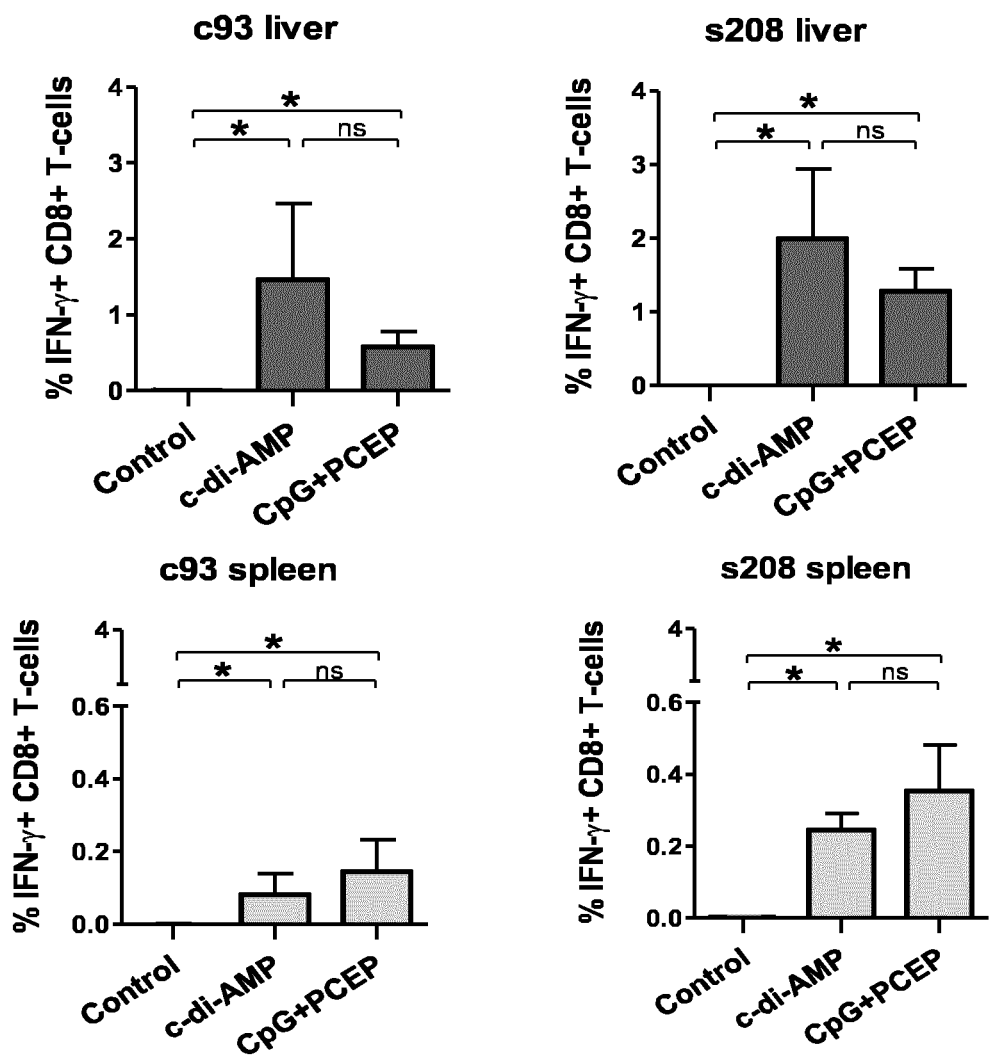

Lack of a safe and effective adjuvant inducing a balanced Th1/Th2 CD4+ T cell response may be an obstacle for initiating clinical trials. Moreover, triggering the newly identified cytoplasmic pattern recognition receptor STING is an interesting alternative for therapeutic vaccination. Therefore, we aimed to investigate the efficacy of c-di-AMP as a potential new adjuvant for a therapeutic hepatitis B vaccine. To this purpose, groups of middle and high antigenemic HBVtg mice (n=7) mice received two protein primes and a MVA boost immunization. Particulate HBsAg and HBcAg for protein priming were combined and adjuvanted with c-di-AMP or a previously established combination of CpG with polyphosphazenes (PCEP). On day 28, mice were boosted with mixture of MVA-S/core (FIG. 30A). HBVtg mice (n=4) that received c-di-AMP injection and 'empty' MVA (MVAwt) were used as controls. The efficacy of the vaccine formulations to induce humoral and cellular immune responses was compared at day 34 (6 days after the boost).

Neither c-di-AMP nor CpG/PCEP immunization protocol had an impact on serum HBeAg levels in high antigenemic HBVtg mice (FIG. 30C). Both tested vaccine formulations induced significant anti-HBc responses. However, immunization with c-di-AMP induced significantly higher titers of anti-HBc antibodies, as compared to CpG/PCEP regimen (p<0.05) (FIG. 30C). Interestingly, both immunization protocols resulted in HBsAg to anti-HBs seroconversion in all examined HBVtg mice (FIG. 30D). High levels of anti-HBs antibodies elicited by the c-di-AMP- or CpG/PCEP-adjuvanted vaccines complexed circulating HBsAg and removed it from the serum of the mice. By contrast, HBVtg mice that received c-di-AMP only followed by MVAwt boost did not develop any anti-HBs, and the levels of HBsAg in the serum of these mice remained unchanged. Importantly, both vaccine formulations induced significant HBsAg-specific (s208) and HBcAg-specific (c93) CD8+ T− cell responses detectable in spleen (p<0.05) and, in particular, liver-associated lymphocytes in the HBVtg mice (p<0.05) (FIG. 30E), accompanied by mild T-cell-induced liver damage due to an increase in ALT (FIG. 30B). There was no statistically significant difference in the magnitude of HBV-specific CD8+ T cell responses elicited by c-di-AMP or CpG/PCEP regimens.

In view of these data, c-di-AMP is considered being a potent adjuvant for therapeutic protein prime-MVA boost vaccination even in high antigenemic HBVtg mice.

Example 11: Estimation of Optimal Delivery Route for Various Adjuvants: c-Di-AMP, Poly-LCIC and RIG-I Ligand For an appropriate adjuvant for the protein priming for the therapeutic heterologous protein-prime/MVA-boost vaccination the screening expanded. Our objective was to compare the efficacy of c-di-AMP to two potential new adjuvants for a therapeutic hepatitis B vaccine: poly-LCIC and RIG-I ligand. Moreover, we examined the various immunization protocols to find the most efficacious application route. To this purpose, groups of low and middle antigenemic HBVtg mice (n=5) received two protein primes and a MVA boost immunization (FIG. 30A). Particulate HBsAg and HBcAg for protein priming were combined and adjuvanted with c-di-AMP, poly-LCIC, or RIG-I ligand. On day 28, mice were boosted with mixture of MVA-sAg and MVA-core. Immunizations were performed either exclusively by intramuscular (i.m.) route, or protein priming was administered subcutaneously (s.c.) followed by intraperitoneal (i.p.) boost. The efficacy of the different vaccine formulations and application routes were compared with respect to inducing humoral and cellular immune responses at day 34 (6 days after the boost).

Figure 31:
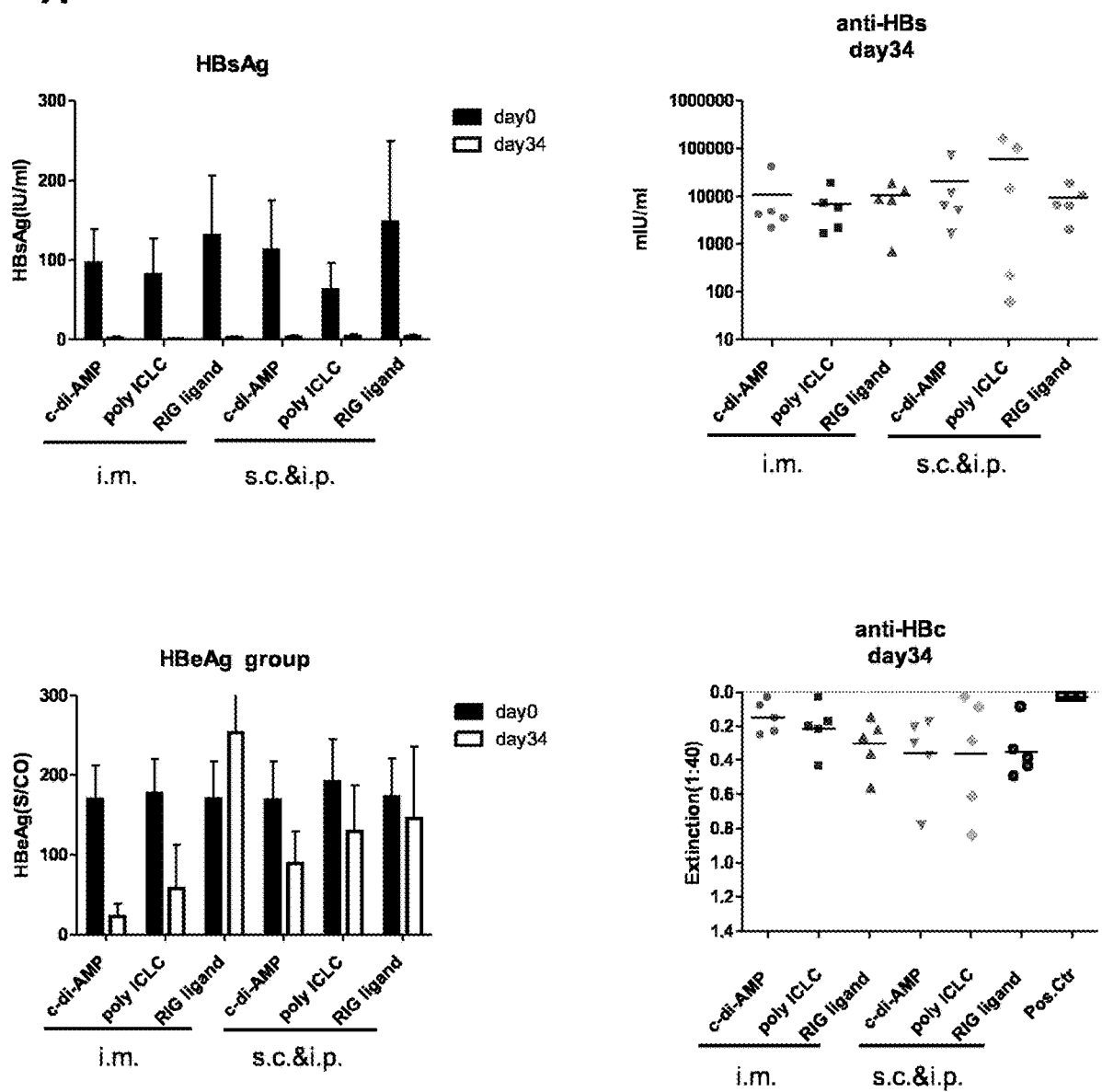
FIG. 31: Estimation of optimal delivery route for various adjuvants: c-di-AMP, poly-IC and RIG-I ligand. HBVtg mice of low and medium antigenemia were grouped according to serum HBeAg levels. (A) Groups of HBVtg mice (n=5) were immunized in two weeks' intervals with mixture of 15 µg of particulate HBsAg and 15 µg of HBcAg adjuvanted with c-di-AMP, poly-IC, or RIG-I ligand. On day 28, mice were boosted with $6 \times 10^7$ MVA-S/core. Immunizations were performed either exclusively by intramuscular route, or protein priming was administered subcutaneously followed by intraperitoneal boost. Sera of mice from day 0 and 34 (day 6 post boost) were analysed for HBsAg, HBeAg, anti-HBs and anti-HBc antibodies (A). The weight of HBVtg mice was monitored weekly over the experiment (B). (C) On day 34 splenocytes and liver-associated lymphocytes of HBVtg mice were isolated and stimulated with MVA-derived peptide B8R, HBsAg-derived peptide s208, or HBcAg-derived peptide c93. Cells were then analyzed for IFNγ-expressing CD8+ T-cells by intracellular cytokine staining. Frequencies of IFNγ-producing T-cells shown are background subtracted. i.m., s.c., i.p.—intramuscular, subcutaneous, intraperitoneal immunization, respectively; S/CO—signal to cutoff; PFU—plague forming units; IU-international units.
Figure 31:
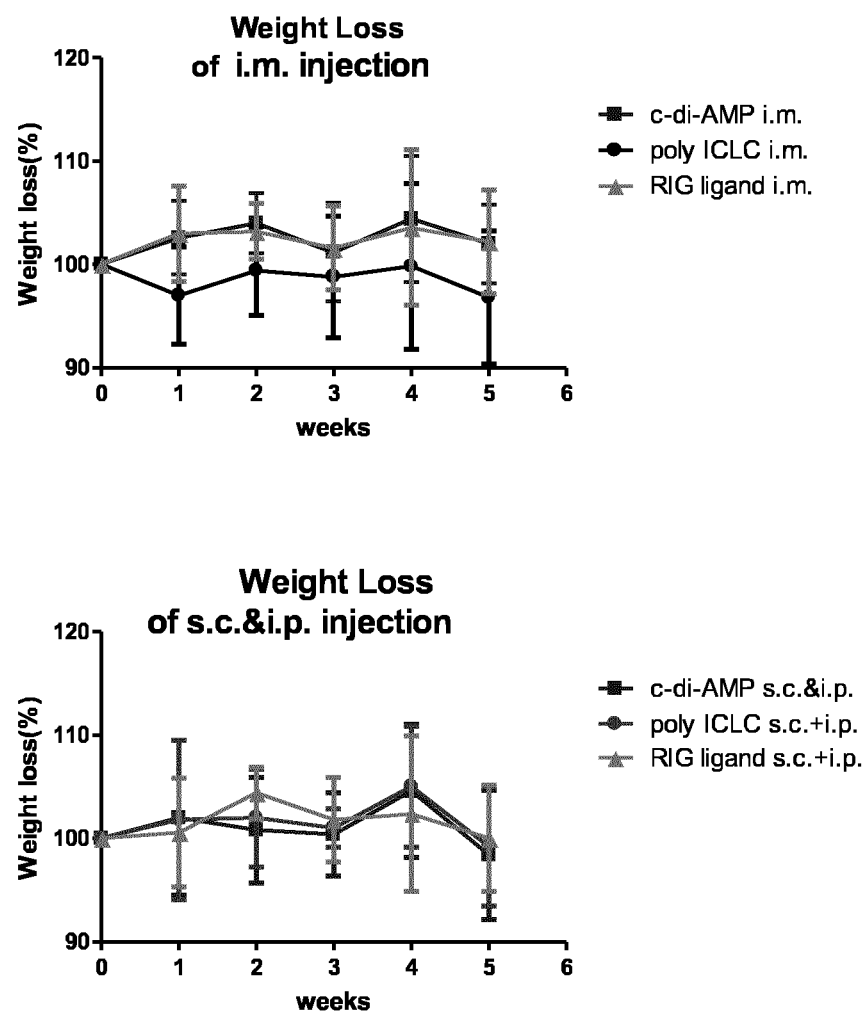
Figure 31:
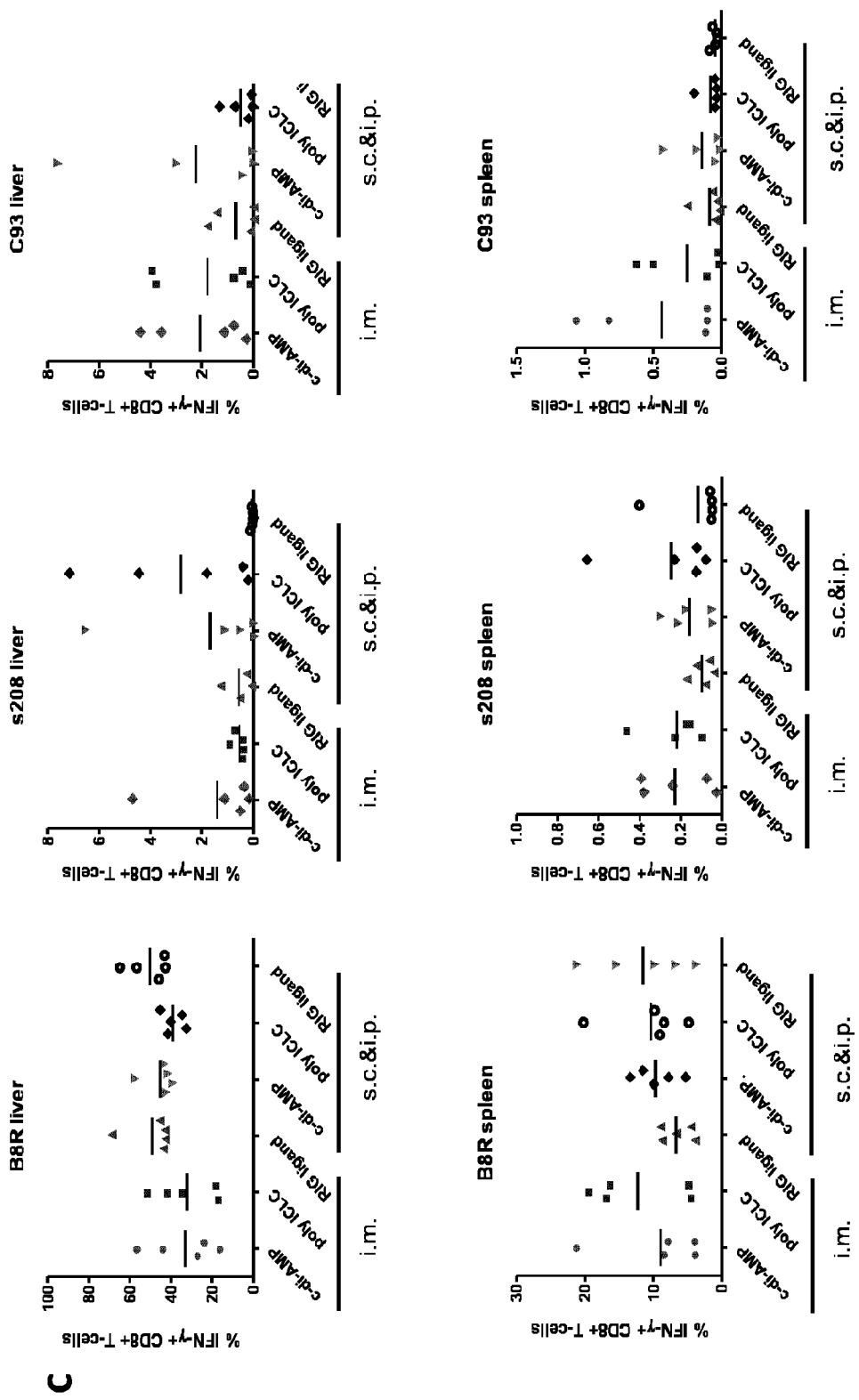

All vaccination protocols potently reduced HBsAg levels in the sera of HBVtg mice. This was due to the fact, that all examined adjuvants and delivery routes could elicit high titers of anti-HBs antibodies that complexed HBsAg in the blood of mice. Similarly, the levels of induced anti-HBc antibodies was comparable between the groups of mice, with a slight tendency that intramuscular immunization route was more potent in induction anti-HBc. Nevertheless, lower HBV replication, detected indirectly by HBeAg levels, was observed only in the groups of HBVtg mice that received c-di-AMP via i.m. or s.c./i.p. routes, or poly-LCIC via i.m. route (FIG. 31A). Unfortunately, immunization with poly-LCIC in intramuscular manner was the only examined protocol that resulted in considerable body weight loss in HBVtg mice (FIG. 31B). C-di-AMP can be considered as being also superior in inducing both HBcAg-specific (c93) and HBsAg-specific (s208) CD8+ T cell responses in the spleens and especially in the livers of immunized HBVtg mice, independently which administration route was used (FIG. 31C). Interestingly poly-LCIC resulted in vigorous intrahepatic HBcAg-specific CD8+ T cell response when delivered intramuscularly, whereas when delivered in s.c./i.p. route predominantly elicited HBsAg-specific (s208) CD8+ T cell responses. RIG-I ligand was able to induce HBV-specific humoral responses, but failed to induce prime HBV-specific CD8+ T cell responses. MVA-specific CD8+ T cell responses, used as controls, were comparable in all immunized groups in spleen and liver, indicating equal vaccination efficiency.

These data demonstrate that c-di-AMP is very potent adjuvant, poly-LCIC shows intermediate efficacy, and RIG-I ligand is not effective enough for therapeutic protein prime-MVA boost vaccination. C-di-AMP was equally effective in both i.m. and s.c./i.p. application routes.

Example 12: Evaluation of the New MVA Construct (MVA-HBVvac) in C57BL/6 Mice

Figure 32:
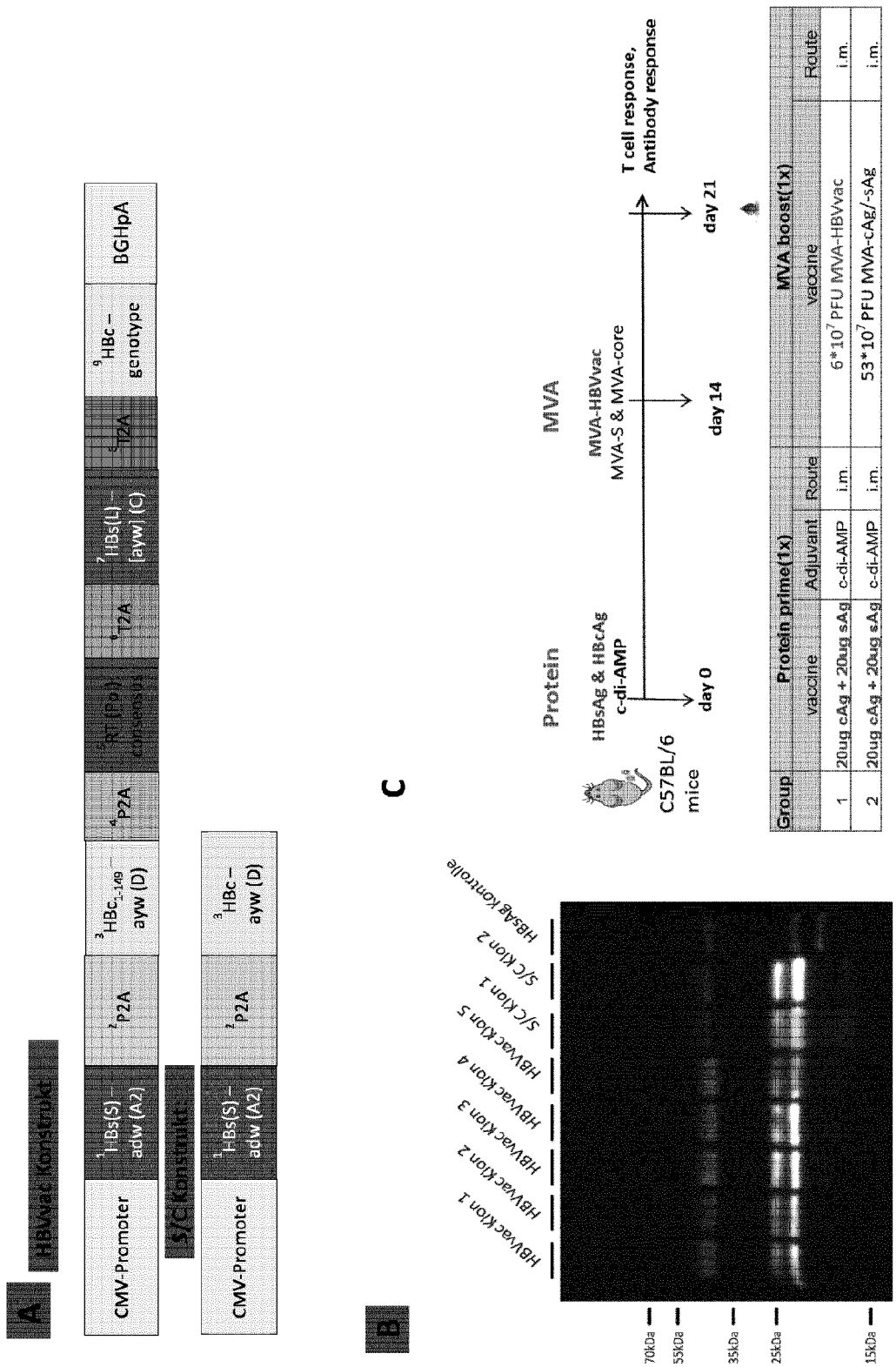
FIG. 32: Evaluation of the new MVA construct (MVA HBVvac) in C57BL/6 mice. (A) Schematic depiction of MVA-S/core and MVA-HBVVac. B) Western blot analysis of lysates from cells producing indicated MVA-clones. Staining for non-glycosylated and glycosylated S using polyclonal antibodies. (C) Groups of C57BL/6 mice (n=5) were primed once with mixture of 20 µg of particulate HBsAg and 20 µg of HBcAg adjuvanted with c-di-AMP. Two weeks later, mice were boosted with either $6 \times 10^7$ MVA-S/core, or with $6 \times 10^7$ MVA-HBVvac, expressing HBsAg, HBcAg and RT domain of HBV polymerase. (D) Sera of mice from day 0 and 21 (day 7 post boost) were analysed for anti-HBs and anti-HBc antibodies. (E) On day 21 splenocytes isolated and stimulated with MVA-derived peptide B8R, HBsAg-, HBcAg- and HBV RT-specific peptides and peptide pools. Ovalbumine-derived peptide SIINFEKL served as negative control. Cells were then analyzed for IFNγ-expressing CD8+ T-cells by intracellular cytokine staining. Red arrows indicate positive RT-specific CD8+ T cell responses. i.m.—intramuscular immunization, respectively; S/CO—signal to cutoff; PFU—plague forming units; IU-international units.
Figure 32:
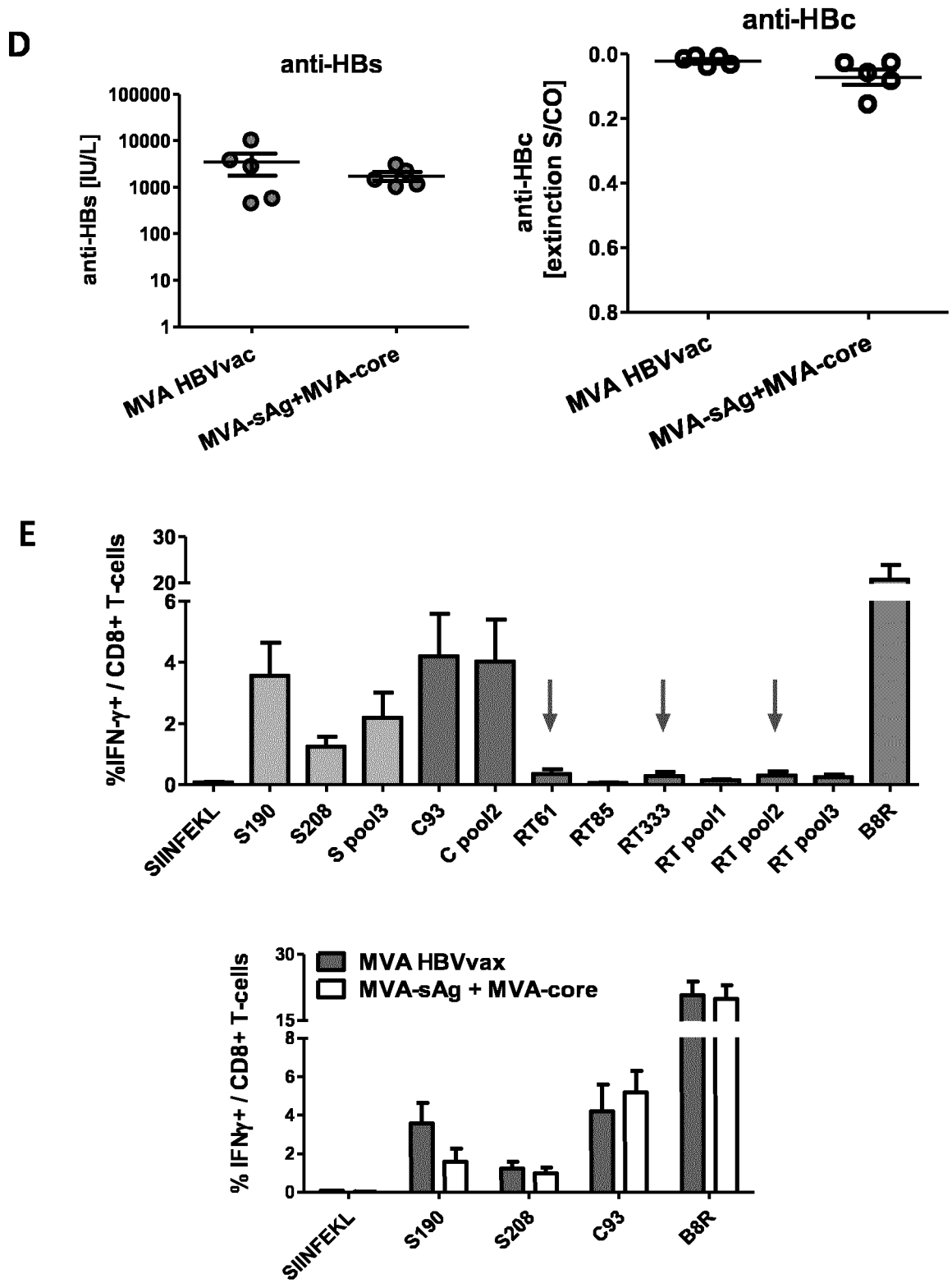

Further, in vivo immunogenicity of the newly constructed polycistronic MVA expressing HBsAg, HBcAg (sequences covering the main HBV genotypes A, B, C, D) and RT domain of HBV polymerase (MVA-HBVvac) was evaluated. Schematic depiction of the two polycystronic vaccination constructs was generated: HBVVac covering HBV core and S of all major HBV genotypes as well as the RT domain of HBV polymerase, and C/S (C/S) expressing HBV core and S (FIG. 32A). Protein expression was confirmed by Western blotting. FIG. 32B shows S-expression by different recombinant MVA-clones expressing either HBVVAc or S/C.

Groups of C57BL/6 mice (n=5) were primed once with mixture of particulate HBsAg and HBcAg adjuvanted with c-di-AMP. Two weeks later, mice were boosted with either mixture of MVA-S and MVA-core, or with equal amount of the new MVA-HBVvac. Mice were sacrificed at day 21 to evaluate HBV-specific humoral and cellular immune responses (FIG. 32C).

The new polycistronic MVA did elicit significant anti-HBs and anti-HBc antibody responses, comparable to the mixture of a combination of MVA-S and MVA-core constructs (FIG. 32D). Moreover, immunization with MVA-HBVvac elicited vigorous HBsAg-specific (s190, s208 and Spool) and HBcAg-specific (c93, Cpool) CD8+ T cell responses (determined by analysing splenocytes) that were similar in magnitude to these induced by the mixture of MVA-S and MVA-core (FIG. 32E). In addition, immunization with MVA-HBVvac resulted in the detection of RT-specific CD8+ T cell responses for peptides RT61, RT333 and RT peptide pool 2 (marked with arrows) at low levels, even though no RT protein was used for priming.

These data showed that the polycistronic MVA (MVA-HBVvac) expressed all proteins expected and showed excellent in vivo immunogenicity in C57BL/6 mice.

Example 13: Increasing Immunogenicity of MVA Constructs by Coexpression of CD70

Figure 34:
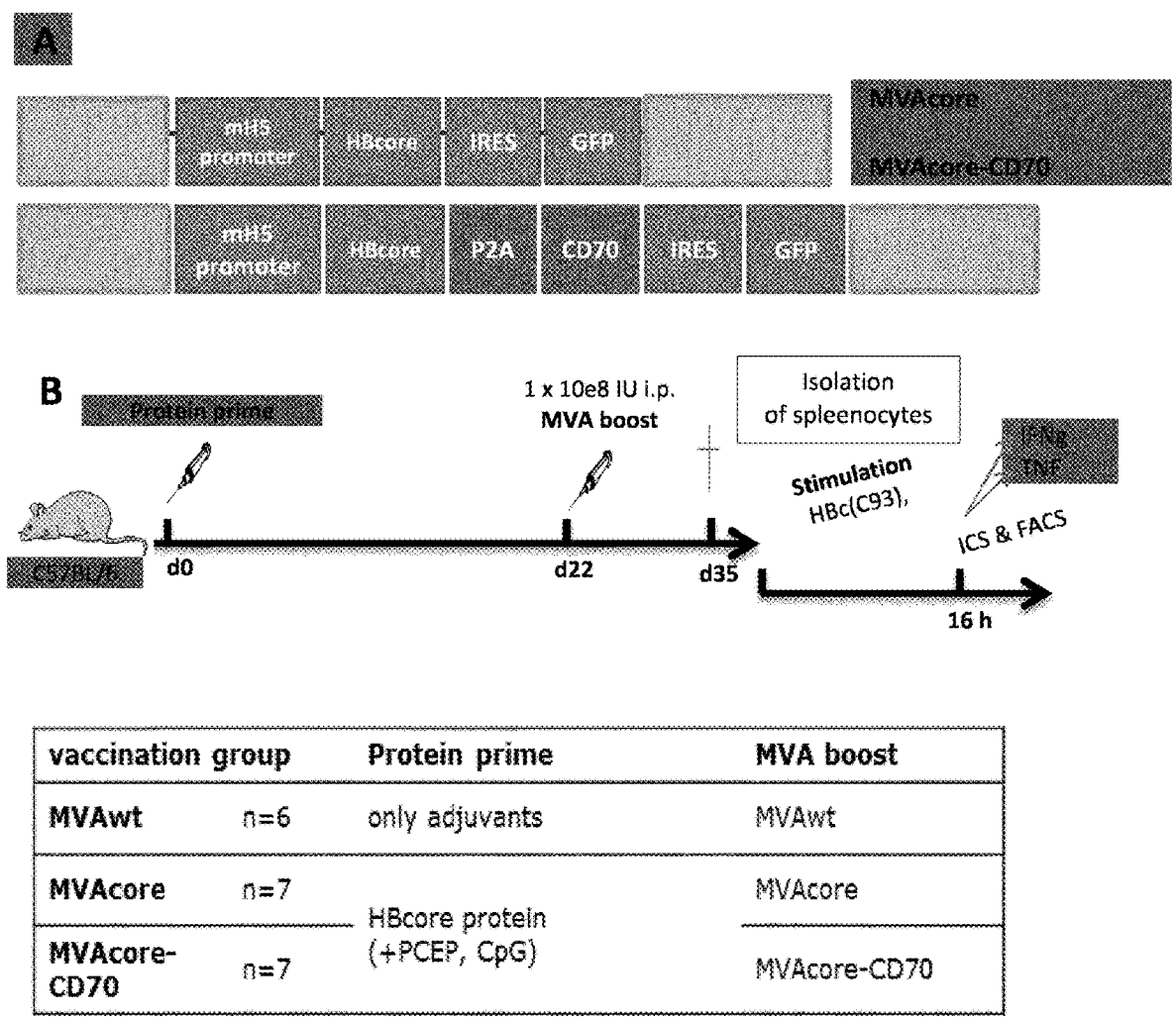
FIG. 34: Evaluation of MVA expressing CD70 in C57BL/6 mice. (A) Schematic depiction of MVAcore and MVAcore-CD70. Both vectors express the HBV core genotype D sequence and GFP to allow easier purification. MVAcore-CD70 expresses in addition a CD70 gene. (B) Groups of C57BL/6 mice (n=6-7) were primed once intramuscularly with 20 µg particulate HBcAg adjuvanted with PCEP and CpG. Three weeks later, mice were boosted with either $10^8$ i.u. MVAcore or $10^8$ MVAcore-CD70 or $10^8$ MVA-wildtype (MVAwt) injected intraperitoneally. (C) On day 35 splenocytes were isolated and stimulated with MVA-derived peptide B8R, or core-peptide C93. Ovalbumine-derived peptide SIINFEKL served as negative control. Cells were then analyzed for IFNγ-expressing CD8+ T-cells by intracellular cytokine staining. Data are given as mean±SD per group. Dots indicate values determined in individual mice. i.u.—infectious units.

To improve in vivo immunogenicity of MVA-based vaccine vectors, a MVA vector that expresses CD70 in a bicistronic fashion was constructed (FIG. 34A).

Groups of C57BL/6 mice (n=6-7) were primed once with particulate HBcAg adjuvanted with CpG and PCEP. Two weeks later, mice were boosted with either MVA-core or with an equal amount MVAcore-CD70 expressing CD70 in addition or a wild type MVA as control (FIG. 34B). Mice were sacrificed at day 35 to evaluate HBV-specific humoral and cellular immune responses. While humoral immune responses were identical after MVAcore and MVAcore-CD70 boost, CD8+ T cell responses against the MVA(B8R)-specific cytokine were slightly and against HBV(C93)-specific cytokine were significantly increased in mice boosted with MVAcore-CD70 (FIG. 34C). A repeat experiment gave identical results.

Figure 35:
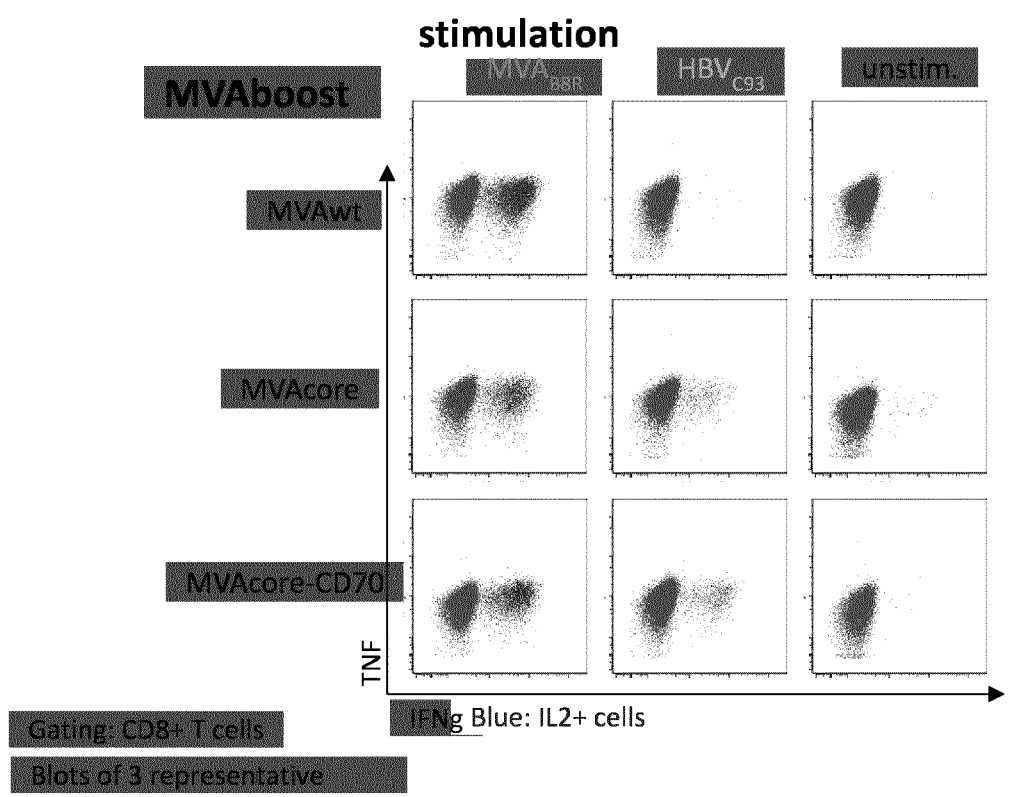
FIG. 35: Evaluation of MVA expressing CD70 in HBV transgenic mice. (A) Schematic depiction of MVAcore and MVAcore-CD70. Both vectors express the HBV core genotype D sequence and GFP to allow easier purification. MVAcore-CD70 expresses in addition a CD70 gene. (B) Groups of transgenic mice carrying a 1.3-fold overlength genome (n=5-6) were primed once intramuscularly with 20 µg particulate HBcAg adjuvanted with PCEP and CpG and three weeks later, boosted with either $10^8$ i.u. MVAcore or $10^8$ MVAcore-CD70 injected intraperitoneally. 2 mice treated accordingly with $10^8$ MVA-wildtype (MVAwt) served as control. (C) On day 35 liver-associated lymphocytes (LAL) were isolated and stimulated with MVA-derived peptide B8R, or core-peptide C93. Unstimulated cells served as negative control. Cells were analyzed by flow cytometry after intracellular cytokine staining for IFNγ (red) and IL-2 (blue). FACS plots for three representative animals are shown.

In a third experiment, groups of HBV-transgenic mice bread on a C57BL/6 background (n=5-6) were vaccinated. In these animals, immune tolerance can be broken upon therapeutic vaccination. After priming once with particulate HBcAg adjuvanted with CpG and PCEP, mice were boosted with either MVA-core or with an equal amount MVAcore-CD70 expressing CD70 (FIGS. 35A and B). Mice vaccinated with a wild type MVA served as control. Mice were sacrificed at day 35 to evaluate MVA- and HBV-specific T cell responses. CD8+ T cells gated onto in liver associated lymphocytes showed a more pronounced secretion of IFNg and IL2 upon re-stimulation with MVA- and HBVcore-specific peptides, respectively, when mice had been vaccinated MVAcore-CD70 compared to mice vaccinated with MVAcore. In mice boosted with MVAwt, MVA-specific, but no HBV-specific T cell responses were detected (FIG. 35C).

Concerning the results above it can be concluded that coexpression of CD70 with an HBV-specific antigen increased MVA—as HBV-specific T cell responses in vivo significantly.

The invention illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The content of all documents and patent documents cited herein is incorporated by reference in their entirety.

The invention claimed is:

1. A recombinant vaccination vector expressing
   (a) an envelope protein (HBs-antigen) from hepatitis B virus serotype adw, wherein the envelope protein is preferably a small or large envelope protein from hepatitis B virus genotype A serotype adw, wherein the small or large envelope protein is preferably a small envelope protein; and
   (b) a core protein (HBc-antigen) from hepatitis B virus serotype ayw, wherein the core protein is preferably from hepatitis B virus genotype D serotype ayw;

and at least one of the following:
   (c) an immunogenic envelope protein (HBs-antigen) from hepatitis B virus having at least 90% sequence identity to the amino acid sequence set forth in SEQ ID NO: 1; and/or
   (d) an immunogenic core protein (HBc-antigen) from hepatitis B virus having at least 90% sequence identity to the amino acid sequence set forth in SEQ ID NO: 2; and/or
   (e) an immunogenic RT domain of a polymerase from hepatitis B virus having at least 90% sequence identity to the amino acid sequence set forth in SEQ ID NO: 3.

2. The recombinant vaccination vector of claim 1, wherein the HBs-antigen in (c) and/or the HBc-antigen in (d) is/are from hepatitis B virus genotype C.

3. The recombinant vaccination vector of claim 1, wherein the immunogenic HBs-antigen in (c) has at least 90% sequence identity to the amino acid sequence set forth in SEQ ID NO: 4 and/or the immunogenic HBc-antigen in (d) has at least 90% sequence identity to the amino acid sequence set forth in SEQ ID NO: 5 and/or the immunogenic RT domain of a polymerase in (e) has at least 90% sequence identity to the amino acid sequence set forth in SEQ ID NO: 6.

4. The recombinant vaccination vector of claim 1, wherein the core protein from hepatitis B virus serotype ayw in (b) is a C-terminally truncated core protein comprising or consisting of amino acids 1-149 of the HBc-antigen from hepatitis B virus genotype D serotype ayw.

5. The recombinant vaccination vector of claim 1, further expressing
(f) a CD70.

6. The recombinant vaccination vector of claim 1, wherein the recombinant vaccination vector is a virus, a virus like particle or a bacterium.

7. The recombinant vaccination vector of claim 1, wherein the recombinant vaccination vector is a MVA virus.

8. The recombinant vaccination vector of claim 1, wherein the recombinant vector is an attenuated *Salmonella* strain, a CMV-, a VSV-based vector, an Adenoviral vector or a Measles vector.

9. A vaccination method against hepatitis B, wherein the method comprises:
(i) administering to a subject
  (a') an envelope protein from hepatitis B virus serotype adw, wherein the envelope protein is preferably a small or large envelope protein from hepatitis B virus genotype A serotype adw, wherein the small or large envelope protein is preferably a small envelope protein; and/or
  (b') a core protein (HBc-antigen) from hepatitis B virus serotype ayw, wherein the core protein is preferably from hepatitis B virus genotype D serotype ayw; and
(ii) administering to the subject a MVA virus expressing
  (a) an envelope protein (HBs-antigen) from hepatitis B virus serotype adw, wherein the envelope protein is preferably a small or large envelope protein from hepatitis B virus genotype A serotype adw, wherein the small or large envelope protein is preferably a small envelope protein;
  and a MVA virus expressing
  (b) a core protein (HBc-antigen) from hepatitis B virus serotype ayw, wherein the core protein is preferably from hepatitis B virus genotype D serotype ayw.

10. A vaccination method against hepatitis B, wherein the method comprises:
(i) administering a subject
  (a') an envelope protein from hepatitis B virus serotype adw, wherein the envelope protein is preferably a small or large envelope protein from hepatitis B virus genotype A serotype adw, wherein the small or large envelope protein is preferably a small envelope protein; and/or
  (b') a core protein (HBc-antigen) from hepatitis B virus serotype ayw, wherein the core protein is preferably from hepatitis B virus genotype D serotype ayw; and
(ii) administering to the subject a MVA virus expressing
  (a) an envelope protein (HBs-antigen) from hepatitis B virus serotype adw, wherein the envelope protein is preferably a small or large envelope protein from hepatitis B virus genotype A serotype adw, wherein the small or large envelope protein is preferably a small envelope protein; and
  (b) a core protein (HBc-antigen) from hepatitis B virus serotype ayw, wherein the core protein is preferably from hepatitis B virus genotype D serotype ayw.

11. The method according to claim 10, wherein the vaccination method is preferably a method for therapeutic vaccination.

12. The method according to claim 10, wherein (i) of the vaccination method is a priming step and (ii) of the vaccination method is a boosting step.

13. The method according to claim 10, wherein the envelope protein and/or the core protein in (i) is co-administered with at least one adjuvant, wherein the adjuvant is preferably selected from the group consisting of poly[di(sodium carboxylatoethylphenoxy)]phosphazene (PCEP), an immune stimulatory oligonucleotide, a toll like receptor (TLR) agonist, a saponin or combinations thereof, wherein the TLR agonist is preferably a TLR 3 agonist, a TLR 4 agonist, a TLR 7 agonist, a TLR 8 agonist, or a TLR 9 agonist, and wherein the immune stimulatory oligonucleotide is preferably poly I/C, CpG, a RIG-I ligand, a STING ligand, cyclic di-AMP, cyclic di-CMP, cyclic di-GMP, a TLR 7 agonist, a TLR 8 agonist, CTA1DD, or dmLT.

14. The method according to claim 10, wherein (i) is conducted at least about 1 day before conducting (ii), preferably at least about 5 days, preferably at least about 1 week, preferably about 1 week to about 8 weeks, preferably about 2 weeks to about 5 weeks, preferably about 3 weeks to about 4 weeks.

15. The method according to claim 10, wherein the vaccination method further comprises after (i) and prior to (ii):
(i') administering to a subject
  (a') an envelope protein from hepatitis B virus genotype A, wherein the envelope protein is preferably a small or large envelope protein from hepatitis B virus genotype A serotype adw, wherein the small or large envelope protein is preferably a small envelope protein; and/or
  (b') a core protein (HBc-antigen) from hepatitis B virus genotype D, wherein the core protein is preferably from hepatitis B virus genotype D serotype ayw,
wherein (i') is preferably a boosting step.

16. The method of claim 10, wherein administration is by a parenteral or mucosal route.

17. A vaccine or a pharmaceutical composition comprising the recombinant vaccination vector of claim 1.

18. The vaccine of claim 17, wherein the recombinant vaccination vector is a MVA virus or a *Salmonella* strain.

19. The vaccine of claim 17, wherein the vaccine is a parenteral or mucosal vaccine.

20. A kit comprising:
(i) a protein composition comprising:
  (a) an envelope protein from hepatitis B virus genotype A, wherein the envelope protein is preferably a small or large envelope protein from hepatitis B virus genotype A serotype adw, wherein the small or large envelope protein is preferably a small envelope protein; and/or
  (b) a core protein (HBc-antigen) from hepatitis B virus genotype D, wherein the core protein is preferably from hepatitis B virus genotype D serotype ayw;
(ii) the vaccine of claim 17.

21. An expression cassette comprising nucleic acids encoding:

(a) an envelope protein (HBs-antigen) from hepatitis B virus serotype adw, wherein the envelope protein is preferably a small or large envelope protein from hepatitis B virus genotype A serotype adw, wherein the small or large envelope protein is preferably a small envelope protein; and (b) a core protein (HBc-antigen) from hepatitis B virus serotype ayw, wherein the core protein is preferably from hepatitis B virus genotype D serotype ayw;

and at least one of the following:

(c) an immunogenic envelope protein (HBs-antigen) from hepatitis B virus having at least 90% sequence identity to the amino acid sequence set forth in SEQ ID NO: 1; and/or (d) an immunogenic core protein (HBc-antigen) from hepatitis B virus having at least 90% sequence identity to the amino acid sequence set forth in SEQ ID NO: 2; and/or (e) an immunogenic RT domain of a polymerase from hepatitis B virus having at least 90% sequence identity to the amino acid sequence set forth in SEQ ID NO: 3.

* * * * *

SEQUENCE LISTING

<160> NUMBER OF SEQ ID NOS: 27

<210> SEQ ID NO 1
<211> LENGTH: 400
<212> TYPE: PRT
<213> ORGANISM: Artificial Sequence
<220> FEATURE:
<223> OTHER INFORMATION: HBV genotype C large envelope protein consensus sequence

<400> SEQUENCE: 1

```
Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly Ala Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Val Pro Ala Ala Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Ala Leu Leu Asp Pro Arg Val Arg Gly Leu Tyr Phe Pro Ala Gly
    130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn Met Glu
                165                 170                 175

Asn Thr Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ala Pro Thr Cys Pro Gly
    210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Leu Pro Gly Thr Ser
        275                 280                 285

Thr Thr Ser Thr Gly Pro Cys Lys Thr Cys Thr Ile Pro Ala Gln Gly
    290                 295                 300

Thr Ser Met Phe Pro Ser Cys Cys Cys Thr Lys Pro Ser Asp Gly Asn
305                 310                 315                 320

Cys Thr Cys Ile Pro Ile Pro Ser Ser Trp Ala Phe Ala Arg Phe Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Val
        355                 360                 365

Ile Trp Met Met Trp Tyr Trp Gly Pro Ser Leu Tyr Asn Ile Leu Ser
    370                 375                 380

Pro Phe Leu Pro Leu Leu Pro Ile Phe Phe Cys Leu Trp Val Tyr Ile
385                 390                 395                 400
```

<210> SEQ ID NO 2

<211> LENGTH: 183
<212> TYPE: PRT
<213> ORGANISM: Artificial Sequence
<220> FEATURE:
<223> OTHER INFORMATION: HBV genotype C core protein consensus sequence

<400> SEQUENCE: 2

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 3
<211> LENGTH: 343
<212> TYPE: PRT
<213> ORGANISM: Artificial Sequence
<220> FEATURE:
<223> OTHER INFORMATION: HBV RT domain of polymerase consensus sequence

<400> SEQUENCE: 3

```
Glu Asp Trp Gly Pro Cys Thr Glu His Gly Glu His His Ile Arg Ile
1               5                   10                  15

Pro Arg Thr Pro Ala Arg Val Thr Gly Gly Val Phe Leu Val Asp Lys
                20                  25                  30

Asn Pro His Asn Thr Ala Glu Ser Arg Leu Val Val Asp Phe Ser Gln
            35                  40                  45

Phe Ser Arg Gly Asn Thr Arg Val Ser Trp Pro Lys Phe Ala Val Pro
        50                  55                  60

Asn Leu Gln Ser Leu Thr Asn Leu Leu Ser Ser Asn Leu Ser Trp Leu
65                  70                  75                  80

Ser Leu Asp Val Ser Ala Ala Phe Tyr His Leu Pro Leu His Pro Ala
                85                  90                  95

Ala Met Pro His Leu Leu Val Gly Ser Ser Gly Leu Ser Arg Tyr Val
            100                 105                 110

Ala Arg Leu Ser Ser Asn Ser Arg Ile Ile Asn His Gln His Gly Thr
        115                 120                 125

Met Gln Asn Leu His Asp Ser Cys Ser Arg Asn Leu Tyr Val Ser Leu
```

```
                130                 135                 140
Leu Leu Leu Tyr Lys Thr Phe Gly Arg Lys Leu His Leu Tyr Ser His
145                 150                 155                 160

Pro Ile Ile Leu Gly Phe Arg Lys Ile Pro Met Gly Val Gly Leu Ser
                165                 170                 175

Pro Phe Leu Leu Ala Gln Phe Thr Ser Ala Ile Cys Ser Val Val Arg
                180                 185                 190

Arg Ala Phe Pro His Cys Leu Ala Phe Ser Tyr Met Asp Asp Val Val
                195                 200                 205

Leu Gly Ala Lys Ser Val Gln His Leu Glu Ser Leu Tyr Thr Ala Val
                210                 215                 220

Thr Asn Phe Leu Leu Ser Leu Gly Ile His Leu Asn Pro Asn Lys Thr
225                 230                 235                 240

Lys Arg Trp Gly Tyr Ser Leu Asn Phe Met Gly Tyr Val Ile Gly Ser
                245                 250                 255

Trp Gly Thr Leu Pro Gln Glu His Ile Val Gln Lys Ile Lys Gln Cys
                260                 265                 270

Phe Arg Lys Leu Pro Val Asn Arg Pro Ile Asp Trp Lys Val Cys Gln
                275                 280                 285

Arg Ile Val Gly Leu Leu Gly Phe Ala Ala Pro Phe Thr Gln Cys Gly
                290                 295                 300

Tyr Pro Ala Leu Met Pro Leu Tyr Ala Cys Ile Gln Ala Lys Gln Ala
305                 310                 315                 320

Phe Thr Phe Ser Pro Thr Tyr Lys Ala Phe Leu Cys Lys Gln Tyr Leu
                325                 330                 335

Asn Leu Tyr Pro Val Ala Arg
                340

<210> SEQ ID NO 4
<211> LENGTH: 400
<212> TYPE: PRT
<213> ORGANISM: Artificial Sequence
<220> FEATURE:
<223> OTHER INFORMATION: HBV large envelope protein

<400> SEQUENCE: 4

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Gly Ala Asn Ser Asn Asn Pro Asp Trp Asp Phe Asn Pro Asn
                35                  40                  45

Lys Asp His Trp Pro Glu Ala Asn Gln Val Gly Ala Gly Ala Phe Gly
                50                  55                  60

Pro Gly Phe Thr Pro Pro His Gly Gly Leu Leu Gly Trp Ser Pro Gln
65                  70                  75                  80

Ala Gln Gly Ile Leu Thr Thr Val Pro Ala Ala Pro Pro Pro Ala Ser
                85                  90                  95

Thr Asn Arg Gln Ser Gly Arg Gln Pro Thr Pro Ile Ser Pro Pro Leu
                100                 105                 110

Arg Asp Ser His Pro Gln Ala Met Gln Trp Asn Ser Thr Thr Phe His
                115                 120                 125

Gln Ala Leu Leu Asp Pro Arg Val Arg Gly Leu Tyr Phe Pro Ala Gly
                130                 135                 140

Gly Ser Ser Ser Gly Thr Val Asn Pro Val Pro Thr Thr Ala Ser Pro
```

```
             145                 150                 155                 160
Ile Ser Ser Ile Phe Ser Arg Thr Gly Asp Pro Ala Pro Asn Met Glu
                    165                 170                 175

Asn Thr Thr Ser Gly Phe Leu Gly Pro Leu Val Leu Gln Ala Gly
            180                 185                 190

Phe Leu Leu Leu Thr Arg Ile Leu Thr Ile Pro Gln Ser Leu Asp Ser
                195                 200                 205

Trp Trp Thr Ser Leu Asn Phe Leu Gly Gly Ala Pro Thr Cys Pro Gly
        210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
                260                 265                 270

Asp Tyr Gln Gly Met Leu Pro Val Cys Pro Leu Leu Pro Gly Thr Ser
                275                 280                 285

Thr Thr Ser Thr Gly Pro Cys Arg Thr Cys Thr Ile Pro Ala Gln Gly
290                 295                 300

Thr Ser Met Phe Pro Ser Cys Cys Cys Thr Lys Pro Ser Asp Gly Asn
305                 310                 315                 320

Cys Thr Cys Ile Pro Ile Pro Ser Ser Trp Ala Phe Ala Lys Phe Leu
                325                 330                 335

Trp Glu Trp Ala Ser Val Arg Phe Ser Trp Leu Ser Leu Leu Val Pro
                340                 345                 350

Phe Val Gln Trp Phe Val Gly Leu Ser Pro Thr Val Trp Leu Ser Val
                355                 360                 365

Ile Trp Met Met Trp Tyr Trp Gly Pro Ser Leu Tyr Asn Ile Leu Ser
                370                 375                 380

Pro Phe Leu Pro Leu Leu Pro Ile Phe Phe Cys Leu Trp Val Tyr Ile
385                 390                 395                 400

<210> SEQ ID NO 5
<211> LENGTH: 183
<212> TYPE: PRT
<213> ORGANISM: Artificial Sequence
<220> FEATURE:
<223> OTHER INFORMATION: HBV core protein

<400> SEQUENCE: 5

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
```

```
                115                 120                 125
Pro Pro Ala Tyr Arg Pro Pro Asn Ala Pro Ile Leu Ser Thr Leu Pro
            130                 135                 140
Glu Thr Thr Val Val Arg Arg Gly Arg Ser Pro Arg Arg Arg Thr
145                 150                 155                 160
Pro Ser Pro Arg Arg Arg Ser Gln Ser Pro Arg Arg Arg Ser
                165                 170                 175
Gln Ser Arg Glu Ser Gln Cys
            180
```

<210> SEQ ID NO 6
<211> LENGTH: 344
<212> TYPE: PRT
<213> ORGANISM: Artificial Sequence
<220> FEATURE:
<223> OTHER INFORMATION: HBV RT domain of polymerase

<400> SEQUENCE: 6

```
Glu Asp Trp Gly Pro Cys Ala Glu His Gly Glu His His Ile Arg Ile
1               5                   10                  15
Pro Arg Thr Pro Ala Arg Val Thr Gly Gly Val Phe Leu Val Asp Lys
            20                  25                  30
Asn Pro His Asn Thr Ala Glu Ser Arg Leu Val Val Asp Phe Ser Gln
        35                  40                  45
Phe Ser Arg Gly Lys Thr Arg Val Ser Trp Pro Lys Phe Ala Val Pro
50                  55                  60
Asn Leu Gln Ser Leu Thr Asn Leu Leu Ser Ser Asn Leu Ser Trp Leu
65                  70                  75                  80
Ser Leu Asp Val Ser Ala Ala Phe Tyr His Ile Pro Leu His Pro Ala
                85                  90                  95
Ala Met Pro His Leu Leu Val Gly Ser Ser Gly Leu Ser Arg Tyr Val
            100                 105                 110
Ala Arg Leu Ser Ser Asn Ser Arg Ile Phe Asn His Gln His Gly Asn
        115                 120                 125
Leu Gln Asn Leu His Asp Ser Cys Ser Arg Asn Leu Tyr Val Ser Leu
130                 135                 140
Leu Leu Leu Tyr Lys Thr Phe Gly Arg Lys Leu His Leu Tyr Ser His
145                 150                 155                 160
Pro Ile Ile Leu Gly Phe Arg Lys Ile Pro Met Gly Val Gly Leu Ser
                165                 170                 175
Pro Phe Leu Leu Ala Gln Phe Thr Ser Ala Ile Cys Ser Val Val Arg
            180                 185                 190
Arg Ala Phe Pro His Cys Leu Ala Phe Ser Tyr Met Asp Asp Val Val
        195                 200                 205
Leu Gly Ala Lys Ser Val Gln His Leu Glu Ser Leu Phe Thr Ala Val
210                 215                 220
Thr Asn Phe Leu Leu Ser Leu Gly Ile His Leu Asn Pro Asn Lys Thr
225                 230                 235                 240
Lys Arg Trp Gly Tyr Ser Leu Asn Phe Met Gly Tyr Val Ile Gly Ser
                245                 250                 255
Trp Gly Thr Leu Pro Gln Glu His Ile Val Gln Lys Ile Lys Gln Cys
            260                 265                 270
Phe Arg Lys Leu Pro Val Asn Arg Pro Ile Asp Trp Lys Val Cys Gln
        275                 280                 285
Arg Ile Val Gly Leu Leu Gly Phe Ala Ala Pro Phe Thr Gln Cys Gly
```

```
                   290                 295                 300
Tyr Pro Ala Leu Met Pro Leu Tyr Ala Cys Ile Gln Ser Lys Gln Ala
305                 310                 315                 320

Phe Thr Phe Ser Pro Thr Tyr Lys Ala Phe Leu Cys Lys Gln Tyr Leu
                325                 330                 335

Asn Leu Tyr Pro Val Ala Arg Gln
                340
```

<210> SEQ ID NO 7
<211> LENGTH: 1388
<212> TYPE: PRT
<213> ORGANISM: Artificial Sequence
<220> FEATURE:
<223> OTHER INFORMATION: fusion polypeptide

<400> SEQUENCE: 7

```
Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
                20                  25                  30

Asp Ser Trp Trp Thr Ser Leu Asn Phe Leu Gly Gly Ser Pro Val Cys
            35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
                100                 105                 110

Ser Thr Thr Thr Ser Thr Gly Pro Cys Lys Thr Cys Thr Thr Pro Ala
            115                 120                 125

Gln Gly Asn Ser Met Phe Pro Ser Cys Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
                180                 185                 190

Ser Ala Ile Trp Met Met Trp Tyr Trp Gly Pro Ser Leu Tyr Ser Ile
            195                 200                 205

Val Ser Pro Phe Ile Pro Leu Leu Pro Ile Phe Phe Cys Leu Trp Val
    210                 215                 220

Tyr Ile Gly Ser Gly Ala Thr Asn Phe Ser Leu Leu Lys Gln Ala Gly
225                 230                 235                 240

Asp Val Glu Glu Asn Pro Gly Pro Met Asp Ile Asp Pro Tyr Lys Glu
                245                 250                 255

Phe Gly Ala Thr Val Glu Leu Leu Ser Phe Leu Pro Ser Asp Phe Phe
                260                 265                 270

Pro Ser Val Arg Asp Leu Leu Asp Thr Ala Ser Ala Leu Tyr Arg Glu
            275                 280                 285

Ala Leu Glu Ser Pro Glu His Cys Ser Pro His His Thr Ala Leu Arg
    290                 295                 300

Gln Ala Ile Leu Cys Trp Gly Glu Leu Met Thr Leu Ala Thr Trp Val
```

```
            305                 310                 315                 320
Gly Val Asn Leu Glu Asp Pro Ala Ser Arg Asp Leu Val Ser Tyr
                325                 330                 335
Val Asn Thr Asn Met Gly Leu Lys Phe Arg Gln Leu Leu Trp Phe His
                340                 345                 350
Ile Ser Cys Leu Thr Phe Gly Arg Glu Thr Val Ile Glu Tyr Leu Val
                355                 360                 365
Ser Phe Gly Val Trp Ile Arg Thr Pro Pro Ala Tyr Arg Pro Pro Asn
        370                 375                 380
Ala Pro Ile Leu Ser Thr Leu Pro Glu Thr Thr Val Val Gly Ser Gly
385                 390                 395                 400
Ala Thr Asn Phe Ser Leu Leu Lys Gln Ala Gly Asp Val Glu Glu Asn
                405                 410                 415
Pro Gly Pro Glu Asp Trp Gly Pro Cys Ala Glu His Gly Glu His His
                420                 425                 430
Ile Arg Ile Pro Arg Thr Pro Ala Arg Val Thr Gly Gly Val Phe Leu
        435                 440                 445
Val Asp Lys Asn Pro His Asn Thr Ala Glu Ser Arg Leu Val Val Asp
    450                 455                 460
Phe Ser Gln Phe Ser Arg Gly Lys Thr Arg Val Ser Trp Pro Lys Phe
465                 470                 475                 480
Ala Val Pro Asn Leu Gln Ser Leu Thr Asn Leu Leu Ser Ser Asn Leu
                485                 490                 495
Ser Trp Leu Ser Leu Asp Val Ser Ala Ala Phe Tyr His Ile Pro Leu
        500                 505                 510
His Pro Ala Ala Met Pro His Leu Leu Val Gly Ser Ser Gly Leu Ser
        515                 520                 525
Arg Tyr Val Ala Arg Leu Ser Ser Asn Ser Arg Ile Phe Asn His Gln
    530                 535                 540
His Gly Asn Leu Gln Asn Leu His Asp Ser Cys Ser Arg Asn Leu Tyr
545                 550                 555                 560
Val Ser Leu Leu Leu Leu Tyr Lys Thr Phe Gly Arg Lys Leu His Leu
                565                 570                 575
Tyr Ser His Pro Ile Ile Leu Gly Phe Arg Lys Ile Pro Met Gly Val
        580                 585                 590
Gly Leu Ser Pro Phe Leu Leu Ala Gln Phe Thr Ser Ala Ile Cys Ser
        595                 600                 605
Val Val Arg Arg Ala Phe Pro His Cys Leu Ala Phe Ser Tyr Met Asp
    610                 615                 620
Asp Val Val Leu Gly Ala Lys Ser Val Gln His Leu Glu Ser Leu Phe
625                 630                 635                 640
Thr Ala Val Thr Asn Phe Leu Leu Ser Leu Gly Ile His Leu Asn Pro
                645                 650                 655
Asn Lys Thr Lys Arg Trp Gly Tyr Ser Leu Asn Phe Met Gly Tyr Val
                660                 665                 670
Ile Gly Ser Trp Gly Thr Leu Pro Gln Glu His Ile Val Gln Lys Ile
        675                 680                 685
Lys Gln Cys Phe Arg Lys Leu Pro Val Asn Arg Pro Ile Asp Trp Lys
        690                 695                 700
Val Cys Gln Arg Ile Val Gly Leu Leu Gly Phe Ala Ala Pro Phe Thr
705                 710                 715                 720
Gln Cys Gly Tyr Pro Ala Leu Met Pro Leu Tyr Ala Cys Ile Gln Ser
                725                 730                 735
```

```
Lys Gln Ala Phe Thr Phe Ser Pro Thr Tyr Lys Ala Phe Leu Cys Lys
            740                 745                 750

Gln Tyr Leu Asn Leu Tyr Pro Val Ala Arg Gln Gly Ser Gly Glu Gly
            755                 760                 765

Arg Gly Ser Leu Leu Thr Cys Gly Asp Val Glu Glu Asn Pro Gly Pro
            770                 775                 780

Met Gly Gly Trp Ser Ser Lys Pro Arg Gln Gly Met Gly Thr Asn Leu
785                 790                 795                 800

Ser Val Pro Asn Pro Leu Gly Phe Phe Pro Asp His Gln Leu Asp Pro
            805                 810                 815

Ala Phe Gly Ala Asn Ser Asn Asn Pro Asp Trp Asp Phe Asn Pro Asn
            820                 825                 830

Lys Asp His Trp Pro Glu Ala Asn Gln Val Gly Ala Gly Ala Phe Gly
            835                 840                 845

Pro Gly Phe Thr Pro Pro His Gly Gly Leu Leu Gly Trp Ser Pro Gln
            850                 855                 860

Ala Gln Gly Ile Leu Thr Thr Val Pro Ala Ala Pro Pro Pro Ala Ser
865                 870                 875                 880

Thr Asn Arg Gln Ser Gly Arg Gln Pro Thr Pro Ile Ser Pro Pro Leu
            885                 890                 895

Arg Asp Ser His Pro Gln Ala Met Gln Trp Asn Ser Thr Thr Phe His
            900                 905                 910

Gln Ala Leu Leu Asp Pro Arg Val Arg Gly Leu Tyr Phe Pro Ala Gly
            915                 920                 925

Gly Ser Ser Ser Gly Thr Val Asn Pro Val Pro Thr Thr Ala Ser Pro
            930                 935                 940

Ile Ser Ser Ile Phe Ser Arg Thr Gly Asp Pro Ala Pro Asn Met Glu
945                 950                 955                 960

Asn Thr Thr Ser Gly Phe Leu Gly Pro Leu Leu Val Leu Gln Ala Gly
            965                 970                 975

Phe Leu Leu Leu Thr Arg Ile Leu Thr Ile Pro Gln Ser Leu Asp Ser
            980                 985                 990

Trp Trp Thr Ser Leu Asn Phe Leu Gly Gly Ala Pro Thr Cys Pro Gly
            995                 1000                1005

Gln Asn Ser Gln Ser Pro Thr Ser Asn His Ser Pro Thr Ser Cys
            1010                1015                1020

Pro Pro Ile Cys Pro Gly Tyr Arg Trp Met Cys Leu Arg Arg Phe
            1025                1030                1035

Ile Ile Phe Leu Phe Ile Leu Leu Leu Cys Leu Ile Phe Leu Leu
            1040                1045                1050

Val Leu Leu Asp Tyr Gln Gly Met Leu Pro Val Cys Pro Leu Leu
            1055                1060                1065

Pro Gly Thr Ser Thr Thr Ser Thr Gly Pro Cys Arg Thr Cys Thr
            1070                1075                1080

Ile Pro Ala Gln Gly Thr Ser Met Phe Pro Ser Cys Cys Cys Thr
            1085                1090                1095

Lys Pro Ser Asp Gly Asn Cys Thr Cys Ile Pro Ile Pro Ser Ser
            1100                1105                1110

Trp Ala Phe Ala Lys Phe Leu Trp Glu Trp Ala Ser Val Arg Phe
            1115                1120                1125

Ser Trp Leu Ser Leu Leu Val Pro Phe Val Gln Trp Phe Val Gly
            1130                1135                1140
```

```
Leu Ser Pro Thr Val Trp Leu Ser Val Ile Trp Met Met Trp Tyr
    1145                1150                1155

Trp Gly Pro Ser Leu Tyr Asn Ile Leu Ser Pro Phe Leu Pro Leu
    1160                1165                1170

Leu Pro Ile Phe Phe Cys Leu Trp Val Tyr Ile Gly Ser Gly Glu
    1175                1180                1185

Gly Arg Gly Ser Leu Leu Thr Cys Gly Asp Val Glu Glu Asn Pro
    1190                1195                1200

Gly Pro Met Asp Ile Asp Pro Tyr Lys Glu Phe Gly Ala Ser Val
    1205                1210                1215

Glu Leu Leu Ser Phe Leu Pro Ser Asp Phe Phe Pro Ser Ile Arg
    1220                1225                1230

Asp Leu Leu Asp Thr Ala Ser Ala Leu Tyr Arg Glu Ala Leu Glu
    1235                1240                1245

Ser Pro Glu His Cys Ser Pro His His Thr Ala Leu Arg Gln Ala
    1250                1255                1260

Ile Leu Cys Trp Gly Glu Leu Met Asn Leu Ala Thr Trp Val Gly
    1265                1270                1275

Ser Asn Leu Glu Asp Pro Ala Ser Arg Glu Leu Val Val Ser Tyr
    1280                1285                1290

Val Asn Val Asn Met Gly Leu Lys Ile Arg Gln Leu Leu Trp Phe
    1295                1300                1305

His Ile Ser Cys Leu Thr Phe Gly Arg Glu Thr Val Leu Glu Tyr
    1310                1315                1320

Leu Val Ser Phe Gly Val Trp Ile Arg Thr Pro Pro Ala Tyr Arg
    1325                1330                1335

Pro Pro Asn Ala Pro Ile Leu Ser Thr Leu Pro Glu Thr Thr Val
    1340                1345                1350

Val Arg Arg Arg Gly Arg Ser Pro Arg Arg Thr Pro Ser Pro
    1355                1360                1365

Arg Arg Arg Arg Ser Gln Ser Pro Arg Arg Arg Ser Gln Ser
    1370                1375                1380

Arg Glu Ser Gln Cys
    1385

<210> SEQ ID NO 8
<211> LENGTH: 226
<212> TYPE: PRT
<213> ORGANISM: Artificial Sequence
<220> FEATURE:
<223> OTHER INFORMATION: HBV small envelope protein

<400> SEQUENCE: 8

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
                20                  25                  30

Asp Ser Trp Trp Thr Ser Leu Asn Phe Leu Gly Gly Ser Pro Val Cys
            35                  40                  45

Leu Gly Gln Asn Ser Gln Ser Pro Thr Ser Asn His Ser Pro Thr Ser
        50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95
```

```
Leu Leu Asp Tyr Gln Gly Met Leu Pro Val Cys Pro Leu Ile Pro Gly
            100                 105                 110

Ser Thr Thr Thr Ser Thr Gly Pro Cys Lys Thr Cys Thr Thr Pro Ala
        115                 120                 125

Gln Gly Asn Ser Met Phe Pro Ser Cys Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Ser Ile
        195                 200                 205

Val Ser Pro Phe Ile Pro Leu Leu Pro Ile Phe Phe Cys Leu Trp Val
    210                 215                 220

Tyr Ile
225

<210> SEQ ID NO 9
<211> LENGTH: 21
<212> TYPE: PRT
<213> ORGANISM: Artificial Sequence
<220> FEATURE:
<223> OTHER INFORMATION: P2A cleavage fragment

<400> SEQUENCE: 9

Gly Ser Gly Ala Thr Asn Phe Ser Leu Leu Lys Gln Ala Gly Asp Val
1               5                   10                  15

Glu Glu Asn Pro Gly
            20

<210> SEQ ID NO 10
<211> LENGTH: 247
<212> TYPE: PRT
<213> ORGANISM: Artificial sequence
<220> FEATURE:
<223> OTHER INFORMATION: HBV small envelope protein

<400> SEQUENCE: 10

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ser Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Ser Thr Gly Pro Cys Lys Thr Cys Thr Thr Pro Ala
        115                 120                 125

Gln Gly Asn Ser Met Phe Pro Ser Cys Cys Cys Thr Lys Pro Thr Asp
    130                 135                 140
```

```
Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Ser Ile
        195                 200                 205

Val Ser Pro Phe Ile Pro Leu Leu Pro Ile Phe Phe Cys Leu Trp Val
    210                 215                 220

Tyr Ile Gly Ser Gly Ala Thr Asn Phe Ser Leu Leu Lys Gln Ala Gly
225                 230                 235                 240

Asp Val Glu Glu Asn Pro Gly
                245

<210> SEQ ID NO 11
<211> LENGTH: 149
<212> TYPE: PRT
<213> ORGANISM: Artificial Sequence
<220> FEATURE:
<223> OTHER INFORMATION: HBV core protein amino acids 1-149

<400> SEQUENCE: 11

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 12
<211> LENGTH: 171
<212> TYPE: PRT
<213> ORGANISM: Artificial Sequence
<220> FEATURE:
<223> OTHER INFORMATION: HBV core protein amino acids 1-149

<400> SEQUENCE: 12

Pro Met Asp Ile Asp Pro Tyr Lys Glu Phe Gly Ala Thr Val Glu Leu
1               5                   10                  15

Leu Ser Phe Leu Pro Ser Asp Phe Phe Pro Ser Val Arg Asp Leu Leu
            20                  25                  30

Asp Thr Ala Ser Ala Leu Tyr Arg Glu Ala Leu Glu Ser Pro Glu His
```

```
             35                  40                  45
Cys Ser Pro His His Thr Ala Leu Arg Gln Ala Ile Leu Cys Trp Gly
 50                  55                  60

Glu Leu Met Thr Leu Ala Thr Trp Val Gly Val Asn Leu Glu Asp Pro
 65                  70                  75                  80

Ala Ser Arg Asp Leu Val Val Ser Tyr Val Asn Thr Asn Met Gly Leu
                 85                  90                  95

Lys Phe Arg Gln Leu Leu Trp Phe His Ile Ser Cys Leu Thr Phe Gly
                100                 105                 110

Arg Glu Thr Val Ile Glu Tyr Leu Val Ser Phe Gly Val Trp Ile Arg
                115                 120                 125

Thr Pro Pro Ala Tyr Arg Pro Pro Asn Ala Pro Ile Leu Ser Thr Leu
130                 135                 140

Pro Glu Thr Thr Val Val Gly Ser Gly Ala Thr Asn Phe Ser Leu Leu
145                 150                 155                 160

Lys Gln Ala Gly Asp Val Glu Glu Asn Pro Gly
                165                 170

<210> SEQ ID NO 13
<211> LENGTH: 20
<212> TYPE: PRT
<213> ORGANISM: Artificial Sequence
<220> FEATURE:
<223> OTHER INFORMATION: T2A cleavage fragment

<400> SEQUENCE: 13

Gly Ser Gly Glu Gly Arg Gly Ser Leu Leu Thr Cys Gly Asp Val Glu
 1               5                  10                  15

Glu Asn Pro Gly
             20

<210> SEQ ID NO 14
<211> LENGTH: 421
<212> TYPE: PRT
<213> ORGANISM: Artificial Sequence
<220> FEATURE:
<223> OTHER INFORMATION: HBV large envelope protein

<400> SEQUENCE: 14

Pro Met Gly Gly Trp Ser Ser Lys Pro Arg Gln Gly Met Gly Thr Asn
 1               5                  10                  15

Leu Ser Val Pro Asn Pro Leu Gly Phe Phe Pro Asp His Gln Leu Asp
                 20                  25                  30

Pro Ala Phe Gly Ala Asn Ser Asn Pro Asp Trp Asp Phe Asn Pro
             35                  40                  45

Asn Lys Asp His Trp Pro Glu Ala Asn Gln Val Gly Ala Gly Ala Phe
 50                  55                  60

Gly Pro Gly Phe Thr Pro Pro His Gly Gly Leu Leu Gly Trp Ser Pro
 65                  70                  75                  80

Gln Ala Gln Gly Ile Leu Thr Thr Val Pro Ala Ala Pro Pro Pro Ala
                 85                  90                  95

Ser Thr Asn Arg Gln Ser Gly Arg Gln Pro Thr Pro Ile Ser Pro Pro
                100                 105                 110

Leu Arg Asp Ser His Pro Gln Ala Met Gln Trp Asn Ser Thr Thr Phe
                115                 120                 125

His Gln Ala Leu Leu Asp Pro Arg Val Arg Gly Leu Tyr Phe Pro Ala
                130                 135                 140
```

```
Gly Gly Ser Ser Ser Gly Thr Val Asn Pro Val Pro Thr Thr Ala Ser
145                 150                 155                 160

Pro Ile Ser Ser Ile Phe Ser Arg Thr Gly Asp Pro Ala Pro Asn Met
            165                 170                 175

Glu Asn Thr Thr Ser Gly Phe Leu Gly Pro Leu Leu Val Leu Gln Ala
                180                 185                 190

Gly Phe Leu Leu Leu Thr Arg Ile Leu Thr Ile Pro Gln Ser Leu Asp
        195                 200                 205

Ser Trp Trp Thr Ser Leu Asn Phe Leu Gly Gly Ala Pro Thr Cys Pro
    210                 215                 220

Gly Gln Asn Ser Gln Ser Pro Thr Ser Asn His Ser Pro Thr Ser Cys
225                 230                 235                 240

Pro Pro Ile Cys Pro Gly Tyr Arg Trp Met Cys Leu Arg Arg Phe Ile
            245                 250                 255

Ile Phe Leu Phe Ile Leu Leu Leu Cys Leu Ile Phe Leu Leu Val Leu
                260                 265                 270

Leu Asp Tyr Gln Gly Met Leu Pro Val Cys Pro Leu Leu Pro Gly Thr
        275                 280                 285

Ser Thr Thr Ser Thr Gly Pro Cys Arg Thr Cys Thr Ile Pro Ala Gln
    290                 295                 300

Gly Thr Ser Met Phe Pro Ser Cys Cys Cys Thr Lys Pro Ser Asp Gly
305                 310                 315                 320

Asn Cys Thr Cys Ile Pro Ile Pro Ser Ser Trp Ala Phe Ala Lys Phe
            325                 330                 335

Leu Trp Glu Trp Ala Ser Val Arg Phe Ser Trp Leu Ser Leu Leu Val
                340                 345                 350

Pro Phe Val Gln Trp Phe Val Gly Leu Ser Pro Thr Val Trp Leu Ser
        355                 360                 365

Val Ile Trp Met Met Trp Tyr Trp Gly Pro Ser Leu Tyr Asn Ile Leu
    370                 375                 380

Ser Pro Phe Leu Pro Leu Leu Pro Ile Phe Phe Cys Leu Trp Val Tyr
385                 390                 395                 400

Ile Gly Ser Gly Glu Gly Arg Gly Ser Leu Leu Thr Cys Gly Asp Val
            405                 410                 415

Glu Glu Asn Pro Gly
            420

<210> SEQ ID NO 15
<211> LENGTH: 184
<212> TYPE: PRT
<213> ORGANISM: Artificial Sequence
<220> FEATURE:
<223> OTHER INFORMATION: HBV core protein

<400> SEQUENCE: 15

Pro Met Asp Ile Asp Pro Tyr Lys Glu Phe Gly Ala Ser Val Glu Leu
1               5                   10                  15

Leu Ser Phe Leu Pro Ser Asp Phe Phe Pro Ser Ile Arg Asp Leu Leu
            20                  25                  30

Asp Thr Ala Ser Ala Leu Tyr Arg Glu Ala Leu Glu Ser Pro Glu His
        35                  40                  45

Cys Ser Pro His His Thr Ala Leu Arg Gln Ala Ile Leu Cys Trp Gly
    50                  55                  60

Glu Leu Met Asn Leu Ala Thr Trp Val Gly Ser Asn Leu Glu Asp Pro
65                  70                  75                  80
```

```
Ala Ser Arg Glu Leu Val Val Ser Tyr Val Asn Val Asn Met Gly Leu
                85                  90                  95

Lys Ile Arg Gln Leu Leu Trp Phe His Ile Ser Cys Leu Thr Phe Gly
        100                 105                 110

Arg Glu Thr Val Leu Glu Tyr Leu Val Ser Phe Gly Val Trp Ile Arg
            115                 120                 125

Thr Pro Pro Ala Tyr Arg Pro Pro Asn Ala Pro Ile Leu Ser Thr Leu
130                 135                 140

Pro Glu Thr Thr Val Val Arg Arg Arg Gly Arg Ser Pro Arg Arg Arg
145                 150                 155                 160

Thr Pro Ser Pro Arg Arg Arg Ser Gln Ser Pro Arg Arg Arg Arg
                165                 170                 175

Ser Gln Ser Arg Glu Ser Gln Cys
                180
```

<210> SEQ ID NO 16
<211> LENGTH: 365
<212> TYPE: PRT
<213> ORGANISM: Artificial Sequence
<220> FEATURE:
<223> OTHER INFORMATION: HBV RT domain of polymerase

<400> SEQUENCE: 16

```
Pro Glu Asp Trp Gly Pro Cys Ala Glu His Gly Glu His His Ile Arg
1               5                   10                  15

Ile Pro Arg Thr Pro Ala Arg Val Thr Gly Gly Val Phe Leu Val Asp
            20                  25                  30

Lys Asn Pro His Asn Thr Ala Glu Ser Arg Leu Val Val Asp Phe Ser
        35                  40                  45

Gln Phe Ser Arg Gly Lys Thr Arg Val Ser Trp Pro Lys Phe Ala Val
    50                  55                  60

Pro Asn Leu Gln Ser Leu Thr Asn Leu Leu Ser Ser Asn Leu Ser Trp
65                  70                  75                  80

Leu Ser Leu Asp Val Ser Ala Ala Phe Tyr His Ile Pro Leu His Pro
                85                  90                  95

Ala Ala Met Pro His Leu Leu Val Gly Ser Ser Gly Leu Ser Arg Tyr
            100                 105                 110

Val Ala Arg Leu Ser Ser Asn Ser Arg Ile Phe Asn His Gln His Gly
        115                 120                 125

Asn Leu Gln Asn Leu His Asp Ser Cys Ser Arg Asn Leu Tyr Val Ser
    130                 135                 140

Leu Leu Leu Leu Tyr Lys Thr Phe Gly Arg Lys Leu His Leu Tyr Ser
145                 150                 155                 160

His Pro Ile Ile Leu Gly Phe Arg Lys Ile Pro Met Gly Val Gly Leu
                165                 170                 175

Ser Pro Phe Leu Leu Ala Gln Phe Thr Ser Ala Ile Cys Ser Val Val
            180                 185                 190

Arg Arg Ala Phe Pro His Cys Leu Ala Phe Ser Tyr Met Asp Asp Val
        195                 200                 205

Val Leu Gly Ala Lys Ser Val Gln His Leu Glu Ser Leu Phe Thr Ala
    210                 215                 220

Val Thr Asn Phe Leu Leu Ser Leu Gly Ile His Leu Asn Pro Asn Lys
225                 230                 235                 240

Thr Lys Arg Trp Gly Tyr Ser Leu Asn Phe Met Gly Tyr Val Ile Gly
                245                 250                 255
```

-continued

```
Ser Trp Gly Thr Leu Pro Gln Glu His Ile Val Gln Lys Ile Lys Gln
            260                 265                 270

Cys Phe Arg Lys Leu Pro Val Asn Arg Pro Ile Asp Trp Lys Val Cys
        275                 280                 285

Gln Arg Ile Val Gly Leu Leu Gly Phe Ala Ala Pro Phe Thr Gln Cys
    290                 295                 300

Gly Tyr Pro Ala Leu Met Pro Leu Tyr Ala Cys Ile Gln Ser Lys Gln
305                 310                 315                 320

Ala Phe Thr Phe Ser Pro Thr Tyr Lys Ala Phe Leu Cys Lys Gln Tyr
                325                 330                 335

Leu Asn Leu Tyr Pro Val Ala Arg Gln Gly Ser Gly Glu Gly Arg Gly
            340                 345                 350

Ser Leu Leu Thr Cys Gly Asp Val Glu Glu Asn Pro Gly
        355                 360                 365

<210> SEQ ID NO 17
<211> LENGTH: 102
<212> TYPE: DNA
<213> ORGANISM: Artificial Sequence
<220> FEATURE:
<223> OTHER INFORMATION: P7.5 promoter

<400> SEQUENCE: 17
tccaaaccca cccgcttttt atagtaagtt tttcaccata ataataaat aaataattaa    60 tttctcgtaa aagtagaaaa tatattctaa tttattgcac gg                      102

<210> SEQ ID NO 18
<211> LENGTH: 138
<212> TYPE: DNA
<213> ORGANISM: Artificial Sequence
<220> FEATURE:
<223> OTHER INFORMATION: PH5 promoter

<400> SEQUENCE: 18
taatcgtgtc atattagtat aaaaagtgat ttatttttac aaaattatgt attttgttct    60
atcaactacc tataaaactt tccctgcagg tcagcttaaa aattgaaatt ttattttttt   120
tttttggaat ataaataa                                                  138

<210> SEQ ID NO 19
<211> LENGTH: 8
<212> TYPE: PRT
<213> ORGANISM: Artificial Sequence
<220> FEATURE:
<223> OTHER INFORMATION: S190 peptide

<400> SEQUENCE: 19

Val Trp Leu Ser Val Ile Trp Met
1               5

<210> SEQ ID NO 20
<211> LENGTH: 8
<212> TYPE: PRT
<213> ORGANISM: Artificial Sequence
<220> FEATURE:
<223> OTHER INFORMATION: MVA B8R peptide

<400> SEQUENCE: 20

Thr Ser Tyr Lys Phe Glu Ser Val
1               5

<210> SEQ ID NO 21
```

```
<211> LENGTH: 8
<212> TYPE: PRT
<213> ORGANISM: Artificial Sequence
<220> FEATURE:
<223> OTHER INFORMATION: S208 peptide

<400> SEQUENCE: 21

Ile Leu Ser Pro Phe Leu Pro Leu
1               5

<210> SEQ ID NO 22
<211> LENGTH: 8
<212> TYPE: PRT
<213> ORGANISM: Artificial Sequence
<220> FEATURE:
<223> OTHER INFORMATION: S208 adw peptide

<400> SEQUENCE: 22

Ile Val Ser Pro Phe Ile Pro Leu
1               5

<210> SEQ ID NO 23
<211> LENGTH: 226
<212> TYPE: PRT
<213> ORGANISM: Artificial Sequence
<220> FEATURE:
<223> OTHER INFORMATION: S Pool peptide

<400> SEQUENCE: 23

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Thr Thr Val Cys
        35                  40                  45

Leu Gly Gln Asn Ser Gln Ser Pro Thr Ser Asn His Ser Pro Thr Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Met Thr Thr Ala
        115                 120                 125

Gln Gly Thr Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Ser Ile
        195                 200                 205

Leu Ser Pro Phe Leu Pro Leu Pro Ile Phe Phe Cys Leu Trp Val
    210                 215                 220

Tyr Ile
225
```

```
<210> SEQ ID NO 24
<211> LENGTH: 8
<212> TYPE: PRT
<213> ORGANISM: Artificial Sequence
<220> FEATURE:
<223> OTHER INFORMATION: C93 peptide

<400> SEQUENCE: 24

Met Gly Leu Lys Phe Arg Gln Leu
1               5

<210> SEQ ID NO 25
<211> LENGTH: 8
<212> TYPE: PRT
<213> ORGANISM: Artificial Sequence
<220> FEATURE:
<223> OTHER INFORMATION: beta-Gal96 peptide

<400> SEQUENCE: 25

Asp Ala Pro Ile Tyr Thr Asn Val
1               5

<210> SEQ ID NO 26
<211> LENGTH: 193
<212> TYPE: PRT
<213> ORGANISM: Homo sapiens

<400> SEQUENCE: 26

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
                20                  25                  30

Cys Leu Val Val Cys Ile Gln Arg Phe Ala Gln Ala Gln Gln Gln Leu
            35                  40                  45

Pro Leu Glu Ser Leu Gly Trp Asp Val Ala Glu Leu Gln Leu Asn His
        50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro

<210> SEQ ID NO 27
<211> LENGTH: 6512
<212> TYPE: DNA
<213> ORGANISM: Artificial Sequence
<220> FEATURE:
<223> OTHER INFORMATION: vaccination vector
```

<400> SEQUENCE: 27

```
cctgggacat acgtatattt ctatgatctg tcttatatga agtctataca gcgaatagat    60
tcagaatttc tacataatta tatattgtac gctaataagt ttaatctaac actccccgaa   120
gatttgttta taatccctac aaatttggat attctatggc gtacaaagga atatatagac   180
tcgttcgata ttagtacaga aacatggaat aaattattat ccaattatta tatgaagatg   240
atagagtatg ctaaacttta tgtactaagt cctattctcg ctgaggagtt ggataatttt   300
gagaggacgg gagaattaac tcgaggccgc tggtacccaa cctaaaaatt gaaaataaat   360
acaaaggttc ttgagggttg tgttaaattg aaagcgagaa ataatcataa ataagcccgg   420
ggatcaacca tggacatcga cccttataaa gaatttggag ctactgtgga gttactctcg   480
tttttgcctt ctgacttctt tccttcagta cgagatcttc tagataccgc tcagctctg    540
tatcgggaag ccttagagtc tcctgagcat tgttcacctc accatactgc actcaggcaa   600
gcaattcttt gctgggggga actaatgact ctagctacct gggtgggtgt taatttggaa   660
gatccagcgt ctagagacct agtagtcagt tatgtcaaca ctaatatggg cctaaagttc   720
aggcaactct tgtggtttca catttcttgt ctcacttttg gaagagaaac agttatagag   780
tatttggtgt ctttcggagt gtggattcgc actcctccag cttatagacc accaaatgcc   840
cctatcctat caacacttcc ggagactact gttgttagac gacgaggcag gtccctaga   900
agaagaactc cctcgcctcg cagacgaagg tctcaatcgc cgcgtcgcag aagatctcaa   960
tctcgggaat ctcaatgtgg ctccggagcc accaacttct ccctgctgaa gcaggccggc  1020
gacgtggagg agaaccccgg cccttgctgg aattcgccct tatcgaccca agtaccgcca  1080
cctaaggcga tgccgaggga gggttcgggc tgctcggtgc ggcgcaggcc ctatgggtgc  1140
gtcctgcggg ctgctttggt cccattggtc gcgggcttgg tgatctgcct cgtggtgtgc  1200
atccagcgct tcgcacaggc tcagcagcag ctgccgctcg agtcacttgg gtgggacgta  1260
gctgagctgc agctgaatca cacaggacct cagcaggacc ccaggctata ctggcagggg  1320
ggcccagcac tgggccgctc cttcctgcat ggaccagagc tggacaaggg gcagctacgt  1380
atccatcgtg atggcatcta catggtacac atccaggtga cgctggccat ctgctcctcc  1440
acgacggcct ccaggcacca ccccaccacc ctggccgtgg gaatctgctc tcccgcctcc  1500
cgtagcatca gcctgctgcg tctcagcttc accaaggtt gtaccattgc ctcccagcgc  1560
ctgacgcccc tggcccgagg ggacacactc tgcaccaacc tcactgggac actttttgcct  1620
tcccgaaaca ctgatgagac cttctttgga gtgcagtggg tgcgccctg attgacccgc   1680
gggcccggga tccgcccctc tccctccccc cccctaacg ttactggccg aagccgcttg  1740
gaataaggcc ggtgtgcgtt tgtctatatg ttatttttcca ccatattgcc gtcttttggc  1800
aatgtgaggg cccggaaacc tggccctgtc ttcttgacga gcattcctag gggtcttttcc  1860
cctctcgcca aaggaatgca aggtctgttg aatgtcgtga aggaagcagt tcctctggaa  1920
gcttcttgaa gacaaacaac gtctgtagcg accctttgca ggcagcggaa ccccccacct  1980
ggcgacaggt gcctctgcgg ccaaaagcca cgtgtataag atacacctgc aaaggcggca  2040
caaccccagt gccacgttgt gagttggata ttgtgaaa gagtcaaatg gctctcctca  2100
agcgtattca caaggggct gaaggatgcc cagaaggtac cccattgtat gggatctgat  2160
ctggggcctc ggtgcacatg ctttacatgt gtttagtcga ggttaaaaaa acgtctaggc  2220
ccccccgaacc acgggggacgt ggttttcctt tgaaaaacac gatgataata tggccacaac  2280
```

```
catggtgagc aagggcgagg agctgttcac cggggtggtg cccatcctgg tcgagctgga    2340
cggcgacgta acggccaca agttcagcgt gtccggcgag ggcgagggcg atgccaccta    2400
cggcaagctg accctgaagt tcatctgcac caccggcaag ctgcccgtgc cctggcccac    2460
cctcgtgacc accctgacct acggcgtgca gtgcttcagc cgctaccccg accacatgaa    2520
gcagcacgac ttcttcaagt ccgccatgcc cgaaggctac gtccaggagc gcaccatctt    2580
cttcaaggac gacggcaact acaagacccg cgccgaggtg aagttcgagg gcgacaccct    2640
ggtgaaccgc atcgagctga agggcatcga cttcaaggag gacggcaaca tcctggggca    2700
caagctggag tacaactaca acagccacaa cgtctatatc atggccgaca gcagaagaa    2760 cggcatcaag gtgaacttca agatccgcca caacatcgag gacggcagcg tgcagctcgc    2820
cgaccactac cagcagaaca cccccatcgg cgacggcccc gtgctgctgc ccgacaacca    2880
ctacctgagc acccagtccg ccctgagcaa agaccccaac gagaagcgcg atcacatggt    2940
cctgctggag ttcgtgaccg ccgccgggat cactctcggc atggacgagc tgtacaagta    3000
aagcggccgc gactctagat cataatcagc catacccact tgtagaggt tttacttgct    3060 ttaaaaaacc tcccacacct cccctgaac ctgaaacata aatgaatgc aattgttgtt    3120 gttaacttgt ttattgcagc ttataatggt tacaaataaa gcaatagcat cacaaatttc    3180
acaaataaag catttttttc actgcattct agttgtggtt tgtcgtcgac ctgcagtcaa    3240
actctaatga ccacatcttt ttttagagat gaaaattt ccacatctcc ttttgtagac    3300
acgactaaac attttgcaga aaaagttta ttagtgttta gataatcgta tacttcatca    3360
gtgtagatag taaatgtgaa cagataaag gtattcttgc tcaatagatt ggtaaattcc    3420
atagaatata ttaatccttt cttcttgaga tcccacatca tttcaaccag agacgtttta    3480
tccaatgatt tacctcgtac tataccacat acaaaactag attttgcagt gacgtcgtat    3540
ctggtattcc taccaaacaa aattttactt ttagttcttt tagaaaattc taaggtagaa    3600
tctctatttg ccaatatgtc atctatggaa ttaccactag caaaaaatga tagaaatata    3660
tattgataca tcgcagctgg ttttgatcta ctatacttta aaaacgaatc agattccata    3720
attgcctgta tcatcagc tgaaaaacta tgttttacac gtattccttc ggcatttctt    3780
tttaatgata tatcttgttt agacaatgat aaagttatca tgtccatgag agacgcgtct    3840
ccgtatcgta taaatatttc attagatgtt agacgcttca ttaggggtat acttctataa    3900
ggtttcttaa tcagtccatc attggttgcg tcaagaacta ctatcggatg ttgttgggta    3960
tctctagtgt tacacatggc cttactaaag tttgggtaaa taactatgat atctctatta    4020
attatagatg catatatttc atttgtcaag gatattagta tcgacttgct atcgtcatta    4080
atacgtgtaa tgtaatcata taatcatgc gatagccaag gaaaatttaa atagatgttc    4140
atcatataat cgtcgctata attcatatta atacgttgac attgactaat ttgtaatata    4200
gcctcgccac gaagaaagct ctcgtattca gtttcatcga taaggatac cgttaaatat    4260 aactggttgc cgatagtctc atagtctatt aagtggtaag tttcgtacaa atacagaatc    4320
cctaaaatat tatctaatgt tggattaatc tttaccataa ctgtataaaa tggagacgga    4380
gtcataacta ttttaccgtt tgtacttact ggaatagcg aaggaataat ctccggacat    4440
gctggtaaag acccaaatgt ctgtttgaag aaatccaatg ttccaggtcc taatctctta    4500
acaaaaatta cgatattcga tcccgatatc ctttgcattc tatttaccag catatcacga    4560
actatattaa gattatctat catgtctatt ctcccaccgt tatataaatc gcctccgcta    4620
agaaacgtta gtatatccat acaatggaat acttcatttc taaaatagta ttcgtttct    4680
```

-continued

```
aattctttaa tgtgaaatcg tatactagaa agggaaaaat tatctttgag ttttccgtta    4740
gaaaagaacc acgaaactaa tgttctgatt gcgtccgatt ccgttgctga attaatggat    4800
ttacaccaaa aactcatata acttctagat gtagaagcat tcgctaaaaa attagtagaa    4860
tcaaaggata taagtagatg ttccaacaag tgagcaattc ccaagatttc atctatatca    4920
ttctcgaatc cgaaattaga aattcccaag tagatatcct tttttcatccg atcgttgatg   4980
aaaatacgaa ctttattcgg taagacaatc atatggaaaa gaatttacca gatatcttct    5040
tttttccaaa ctgcgttaat gtattctctt acaaatattc acaagatgaa ttcagtaata    5100
tgagtaaaac ggaacgtgat agtttctcat tggcggtgtt tccagttata aaacatagat    5160
ggcataacgc acacgttgta aaacataaag gaatatacaa agttagtaca gaagcacgtg    5220
gaaaaaaagt atctcctcca tcactaggaa aacccgcaca cataaaccta accgcgaagc    5280
aatatatata cagtgaacac acaataagct ttgaatgtta tagttttcta aaatgtataa    5340
caaatacaga aatcaattcg ttcgatgagt atatattaag aggactatta gaagctggta    5400
atagtttaca gatattttcc aattccgtag gtaaacgaac agatactata ggtgtactag    5460
ggaataagta tccatttagc aaaattccat tggcctcatt aactcctaaa gcacaacgag    5520
agatattttc agcgtggatt tctcatagac ctgtagtttt aactggagga actggagtgg    5580
gtaagacgtc acaggtaccc aagttattgc tttggtttaa ttatttattt ggtggattct    5640
ctactctaga taaaatcact gactttcacg aaagaccagt cattctatct cttcctagga    5700
tagctttagt tagattgcat agcaatacca ttttaaaatc attgggattt aaggtactag    5760
atggatctcc tatttcttta cggtacggat ctataccgga agaattaata aacaaacaac    5820
caaaaaaata tggaattgta ttttctaccc ataagttatc tctaacaaaa ctatttagtt    5880
atggcactct tattatagac gaagttcatg agcatgatca aataggagat attattatag    5940
cagtagcgag aaagcatcat acgaaaatag attctatgtt tttaatgact gccacgttag    6000
aggatgacag ggaacggcta aaagtatttt tacctaatcc cgcatttata catattcctg    6060
gagatacact gtttaaaatt agcgaggtat ttattcataa taagataaat ccatcttcca    6120
gaatggcata catagaagaa gaaaagagaa atttagttac tgctatacag atgtatactc    6180
ctcctgatgg atcatccggt atagtctttg tggcatccgt tgcacagtgt cacgaatata    6240
aatcatattt agaaaaaaga ttaccgtatg atatgtatat tattcatggt aaggtcttag    6300
atatagacga aatattagaa aaagtgtatt catcacctaa tgtatcgata attatttcta    6360
ctccttattt ggaatccagc gttactatac gcaatgttac acacatttat gatatgggta    6420
gagttttttgt ccccgctcct tttggaggat cgcaagaatt tatttctaaa tctatgagag    6480
atcaacgaaa aggaagagta ggaagagtta at                                  6512
```